United States Patent
Muehlebach et al.

(10) Patent No.: US 10,292,391 B2
(45) Date of Patent: May 21, 2019

(54) PESTICIDALLY ACTIVE 1,2,4-TRIAZOLE DERIVATIVES WITH SULPHUR CONTAINING SUBSTITUENTS

(71) Applicant: Syngenta Participations AG, Basel (CH)

(72) Inventors: Michel Muehlebach, Stein (CH); Pierre Joseph Marcel Jung, Stein (CH); Andrew Edmunds, Stein (CH); Daniel Emery, Stein (CH); Anke Buchholz, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 15/747,215

(22) PCT Filed: Jul. 18, 2016

(86) PCT No.: PCT/EP2016/067003
§ 371 (c)(1),
(2) Date: Jan. 24, 2018

(87) PCT Pub. No.: WO2017/016910
PCT Pub. Date: Feb. 2, 2017

(65) Prior Publication Data
US 2018/0213781 A1 Aug. 2, 2018

(30) Foreign Application Priority Data

Jul. 24, 2015 (EP) .................................. 15178308
Sep. 21, 2015 (EP) .................................. 15186015
Feb. 8, 2016 (EP) .................................. 16154598

(51) Int. Cl.
| | |
|---|---|
| *A01N 43/653* | (2006.01) |
| *A01N 53/00* | (2006.01) |
| *A01N 55/08* | (2006.01) |
| *C07D 401/14* | (2006.01) |
| *C07F 5/02* | (2006.01) |

(52) U.S. Cl.
CPC ............ *A01N 43/653* (2013.01); *A01N 53/00* (2013.01); *A01N 55/08* (2013.01); *C07D 401/14* (2013.01); *C07F 5/025* (2013.01)

(58) Field of Classification Search
CPC .... C07D 401/14; A01N 43/653; A01N 53/00; A01N 55/08; C07F 5/025
USPC ............................................................ 514/256
See application file for complete search history.

(56) References Cited

FOREIGN PATENT DOCUMENTS

| | | |
|---|---|---|
| EP | 1123287 B1 | 5/2000 |
| WO | 2015144826 A1 | 10/2015 |

OTHER PUBLICATIONS

Extended European Search Report for EP15178308.1, dated Sep. 28, 2015.
International Search Report for PCT/EP2016/067003, dated Sep. 21, 2016.
WrOp for PCT/EP2016/067003, dated Jun. 20, 2017.
IPRP for PCT/EP2016/067003, dated Oct. 30, 2017.

*Primary Examiner* — Kahsay Habte
(74) *Attorney, Agent, or Firm* — Toni-Junell Herbert; Dinsmore & Shohl LLP

(57) ABSTRACT

Compounds of formula (I) wherein the substituents are as defined in claim 1, and the agrochemically acceptable salts salts, stereoisomers, enantiomers, tautomers and N-oxides of those compounds, can be used as insecticides and can be prepared in a manner known per se.

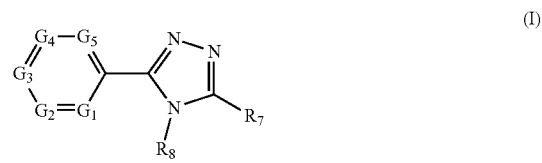

16 Claims, No Drawings

PESTICIDALLY ACTIVE 1,2,4-TRIAZOLE DERIVATIVES WITH SULPHUR CONTAINING SUBSTITUENTS

RELATED APPLICATION INFORMATION

This application is a 371 of International Application No. PCT/EP2016/067003, filed 18 Jul. 2016, which claims priority to EP15178308.1, filed 24 Jul. 2015, EP15186015.2, filed 21 Sep. 2015, and EP16154598.3, filed 08 Feb. 2016, the contents of which are incorporated herein by reference herein.

The present invention relates to pesticidally active, in particular insecticidally active heterocyclic derivatives containing sulphur substituents, to processes for their preparation, to compositions comprising those compounds, and to their use for controlling animal pests, including arthropods and in particular insects or representatives of the order Acarina.

Heterocyclic compounds with pesticidal action are known and described, for example, in WO 2010/125985, WO 2013/018928 and EP 1123287. There have now been found novel pesticidally active heterocyclic triazole derivatives with sulphur containing phenyl and pyridyl substituents.

The present invention accordingly relates to compounds of formula I,

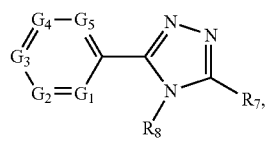

(I)

wherein $G_1$ is nitrogen or $CR_2$;

$G_2$ is nitrogen or $CR_3$;

$G_3$ is nitrogen or $CR_4$;

$G_4$ is nitrogen or $CR_5$;

$G_5$ is nitrogen or $CR_6$, with the proviso that not more than 2 nitrogens as G may follow consecutively;

$R_2$, $R_3$, $R_4$, $R_5$ or $R_6$ are, independently from each other, hydrogen, halogen, $C_1$-$C_4$haloalkyl, $C_1$-$C_4$haloalkyl substituted by one or two hydroxy, $C_1$-$C_4$haloalkyl substituted by one or two methoxy, $C_1$-$C_4$haloalkyl substituted by one or two cyano; or $R_2$, $R_3$, $R_4$, $R_5$ or $R_6$ are, independently from each other, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $SF_5$, phenylcarbonylthio, cyano, mercapto, $C_1$-$C_4$alkoxycarbonyl, $C_1$-$C_4$alkylcarbonyl or —C(O)$C_1$-$C_4$haloalkyl; or $R_2$, $R_3$, $R_4$, $R_5$ or $R_6$ are, independently from each other, $C_3$-$C_6$cycloalkyl which can be mono- or polysubstituted by substituents selected from the group consisting of halogen, cyano and $C_1$-$C_4$alkyl;

or two adjacent $R_i$, wherein $R_i$ is selected from $R_2$, $R_3$, $R_4$, $R_5$ and $R_6$, taken together may form a fragment —OCH$_2$O— or —OCF$_2$O—;

$R_8$ is hydrogen, $C_1$-$C_4$alkyl or $C_1$-$C_4$haloalkyl;

$R_7$ is a radical selected from the group consisting of formula $Q_1$ and $Q_2$

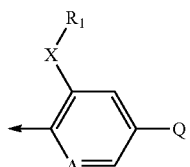

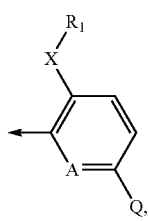

wherein the arrow denotes the point of attachment to the triazole ring;

and wherein A represents CH or N;

Q is phenyl which can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or Q is a five- to ten-membered monocyclic or fused bicyclic ring system linked via a carbon atom to the ring which contains the group A, said ring system can be aromatic, partially saturated or fully saturated and contains 1 to 4 hetero atoms selected from the group consisting of nitrogen, oxygen and sulfur, it not being possible for each ring system to contain more than 2 oxygen atoms and more than 2 sulfur atoms, said five- to ten-membered ring system can be mono- to polysubstituted by substituents independently selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or Q is a five- to six-membered, aromatic, partially saturated or fully saturated ring system linked via a nitrogen atom to the ring which contains the group A, said ring system can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; and said ring system contains 1, 2 or 3 heteroatoms selected from the group consisting of nitrogen, oxygen and sulfur, where said ring system may not contain more than one oxygen atom and not more than one sulfur atom; or Q is $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$haloalkyl, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or Q is $C_2$-$C_6$alkenyl, or $C_2$-$C_6$alkenyl mono- or polysubstituted by substituents selected from the group consisting of halogen, cyano, $C_1$-$C_4$alkyl, $C_1$-$C_4$haloalkyl, $C_1$-$C_4$alkoxy, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$halo-alkylsulfinyl, $C_1$-$C_4$haloalkylsulfonyl and —C(O)$C_1$-$C_4$haloalkyl; or Q is $C_2$-$C_6$alkynyl, or $C_2$-$C_6$alkynyl mono- or polysubstituted by substituents selected from the group consisting of halogen, cyano, $C_1$-$C_4$alkyl, $C_1$-$C_4$haloalkyl, $C_3$-$C_6$cycloalkyl, tri($C_1$-$C_4$alkyl)silyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or Q is $C_1$-$C_6$haloalkylsulfanyl, $C_1$-$C_6$haloalkylsulfinyl, $C_1$-$C_6$haloalkylsulfonyl, $C_1$-$C_6$haloalkoxy, —C(O)$C_1$-$C_4$haloalkyl, $C_1$-$C_6$alkylsulfanyl, $C_1$-$C_6$alkylsulfinyl, or $C_1$-$C_6$alkylsulfonyl;

X is S, SO or $SO_2$; and $R_1$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl; or $R_1$ is $C_3$-$C_6$cycloalkyl mono- or polysubstituted by substituents selected from the group consisting of halogen, cyano and $C_1$-$C_4$alkyl; or $R_1$ is $C_3$-$C_6$cycloalkyl-$C_1$-$C_4$alkyl mono- or polysubstituted by substituents selected from the group consisting of halogen, cyano and $C_1$-$C_4$alkyl; or $R_1$ is $C_2$-$C_6$alkenyl, $C_2$-$C_6$haloalkenyl or $C_2$-$C_6$alkynyl;

and agrochemically acceptable salts, stereoisomers, enantiomers, tautomers and N-oxides of the compounds of formula I.

Compounds of formula I which have at least one basic centre can form, for example, acid addition salts, for example with strong inorganic acids such as mineral acids, for example perchloric acid, sulfuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy.

Alkoxyalkyl groups preferably have a chain length of 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkylsulfanyl is for example methylsulfanyl, ethylsulfanyl, propylsulfanyl, isopropylsulfanyl, butylsulfanyl, pentylsulfanyl, and hexylsulfanyl.

Alkylsulfinyl is for example methylsulfinyl, ethylsulfinyl, propylsulfinyl, isopropylsulfinyl, a butylsulfinyl, pentylsulfinyl, and hexylsulfinyl.

Alkylsulfonyl is for example methylsulfonyl, ethylsulfonyl, propylsulfonyl, isopropylsulfonyl, butylsulfonyl, pentylsulfonyl, and hexylsulfonyl.

The cycloalkyl groups preferably have from 3 to 6 ring carbon atoms, for example cyclopropyl, cyclobutyl, cyclopentyl and cyclohexyl.

Haloalkoxy groups preferably have a chain length of from 1 to 4 carbon atoms. Haloalkoxy is, for example, difluoromethoxy, trifluoromethoxy or 2,2,2-trifluoroethoxy.

Haloalkylsulfanyl groups preferably have a chain length of from 1 to 4 carbon atoms. Haloalkylsulfanyl is, for example, difluoromethylsulfanyl, trifluoromethylsulfanyl or 2,2,2-trifluoroethylsulfanyl. Similar considerations apply to the radicals $C_1$-$C_4$haloalkylsulfinyl and $C_1$-$C_4$haloalkylsulfonyl, which may be, for example, trifluoromethylsulfinyl, trifluoromethylsulfonyl or 2,2,2-trifluoroethylsulfonyl.

According to the present invention, when two adjacent $R_i$, wherein $R_i$ is selected from $R_2$, $R_3$, $R_4$, $R_5$ and $R_6$, taken together form a fragment —$OCH_2O$— or —$OCF_2O$— then an additional five-membered dioxolane or difluoro-dioxolane ring is formed. For example, compounds of the formula I, wherein $G_2$ is $CR_3$, $G_3$ is $CR_4$, and in which $R_3$ and $R_4$ taken together form the fragment —$OCF_2O$—, will have the following structure:

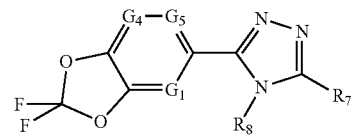

In the context of this invention, examples of a five- to six-membered, aromatic, partially saturated or fully saturated ring system that are linked via a nitrogen atom to the ring which contains the group A, are selected from pyrazole, pyrrole, pyrrolidine, pyrrolidine-2-one, piperidine, morpholine, imidazole, triazole and pyridine-2-one.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, double- or triple-substituted.

Free radicals represents methyl groups.

The compounds of formula I according to the invention also include hydrates which may be formed during the salt formation.

According to the present invention, Q as a five- to ten-membered monocyclic or fused bicyclic ring system that is linked via a carbon atom to the ring which contains the group A, said ring system can be aromatic, partially saturated or fully saturated and contains 1 to 4 hetero atoms selected from the group consisting of nitrogen, oxygen and sulfur, it not being possible for each ring system to contain more than 2 oxygen atoms and more than 2 sulfur atoms, or Q as a three- to ten-membered, monocyclic or fused bicyclic ring system which may be aromatic, partially saturated or fully saturated, is, depending of the number of ring members, preferably selected from the group consisting of the following heterocyclic groups:

pyrrolyl; pyrazolyl; isoxazolyl; furanyl; thienyl; imidazolyl; oxazolyl; thiazolyl; isothiazolyl; triazolyl; oxadiazolyl; thiadiazolyl; tetrazolyl; furyl; pyridyl; pyrimidyl; pyrazinyl; pyridazinyl; triazinyl, pyranyl; quinazolinyl; isoquinolinyl; indolizinyl; isobenzofuranylnaphthyridinyl; quinoxalinyl; cinnolinyl; phthalazinyl; benzothiazolyl; benzoxazolyl; benzotriazolyl; indazolyl; indolyl; (1H-pyrrol-1-yl)-; (1H-pyrrol-2-yl)-; (1H-pyrrol-3-yl)-; (1H-pyrazol-1-yl)-; (1H-pyrazol-3-yl)-; (3H-pyrazol-3-yl)-; (1H-pyrazol-4-yl)-; (3-isoxazolyl)-; (5-isoxazolyl)-; (2-furanyl)-; (3-furanyl)-; (2-thienyl)-; (3-thienyl)-; (1H-imidazol-2-yl)-; (1H-imidazol-4-yl)-; (1H-imidazol-5-yl)-; (2-oxazol-2-yl)-; (oxazol-4-yl)-; (oxazol-5-yl)-; (thiazol-2-yl)-; (thiazol-4-yl)-; (thiazol-5-yl)-; (isothiazol-3-yl)-; (isothiazol-5-yl)-; (1H-1,2,3-triazol-1-yl)-; (1H-1,2,4-triazol-3-yl)-; (4H-1,2,4-triazol-4-yl)-; (1H-1,2,4-triazol-1-yl)-; (1,2,3-oxadiazol-2-yl)-; (1,2,4-oxadiazol-3-yl)-; (1,2,4-oxadiazol-4-yl)-; (1,2,4-oxadiazol-5-yl)-; (1,2,3-thiadiazol-2-yl)-; (1,2,4-thiadiazol-3-yl)-; (1,2,4-thiadiazol-4-yl)-; (1,3,4-thiadiazol-5-yl)-; (1H-tetrazol-1-yl)-; (1H-tetrazol-5-yl)-; (2H-tetrazol-5-yl)-; (2-pyridyl)-; (3-pyridyl)-; (4-pyridyl)-; (2-pyrimidinyl)-; (4-pyrimidinyl)-; (5-pyrimidinyl)-; (2-pyrazinyl)-; (3-pyridazinyl)-; (4-pyridazinyl)-; (1,3,5-triazin-2-yl)-; (1,2,4-triazin-5-yl)-; (1,2,4-triazin-6-yl)-; (1,2,4-triazin-3-yl)-; (furazan-3-yl)-; (2-quinolinyl)-; (3-quinolinyl)-; (4-quinolinyl)-; (5-quinolinyl)-; (6-quinolinyl)-; (3-isoquinolnyl)-; (4-isoquinolnyl)-; (2-quinozolinyl)-; (2-quinoxalinyl)-; (5-quinoxalinyl)-; (pyrido[2,3-b]pyrazin-7-yl)-; (benzoxazol-5-yl)-; (benzothiazol-5-yl)-; (benzo[b]thien-2-yl) and (benzo[1,2,5]oxadiazol-5-yl)-; indolinyl and tetrahydroquinolynyl.

In preferred compounds of formula I, Q is selected from the group consisting of J-0 to J-51 (where the arrow represents the point of attachment of the group J to the ring which contains the group A):

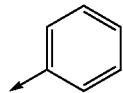

J-0

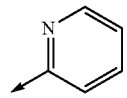

J-1

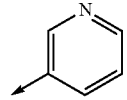

J-2

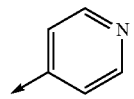

J-3

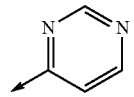

J-4

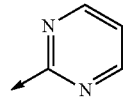

J-5

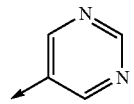

J-6

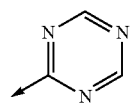

J-7

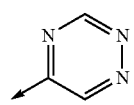

J-8

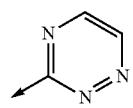

J-9

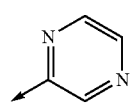

J-10

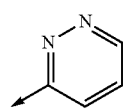

J-11

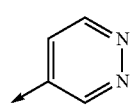

J-12

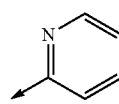

J-13

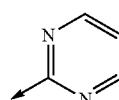

J-14

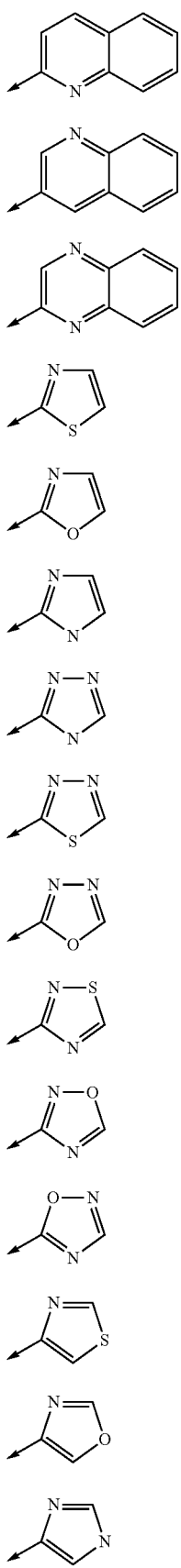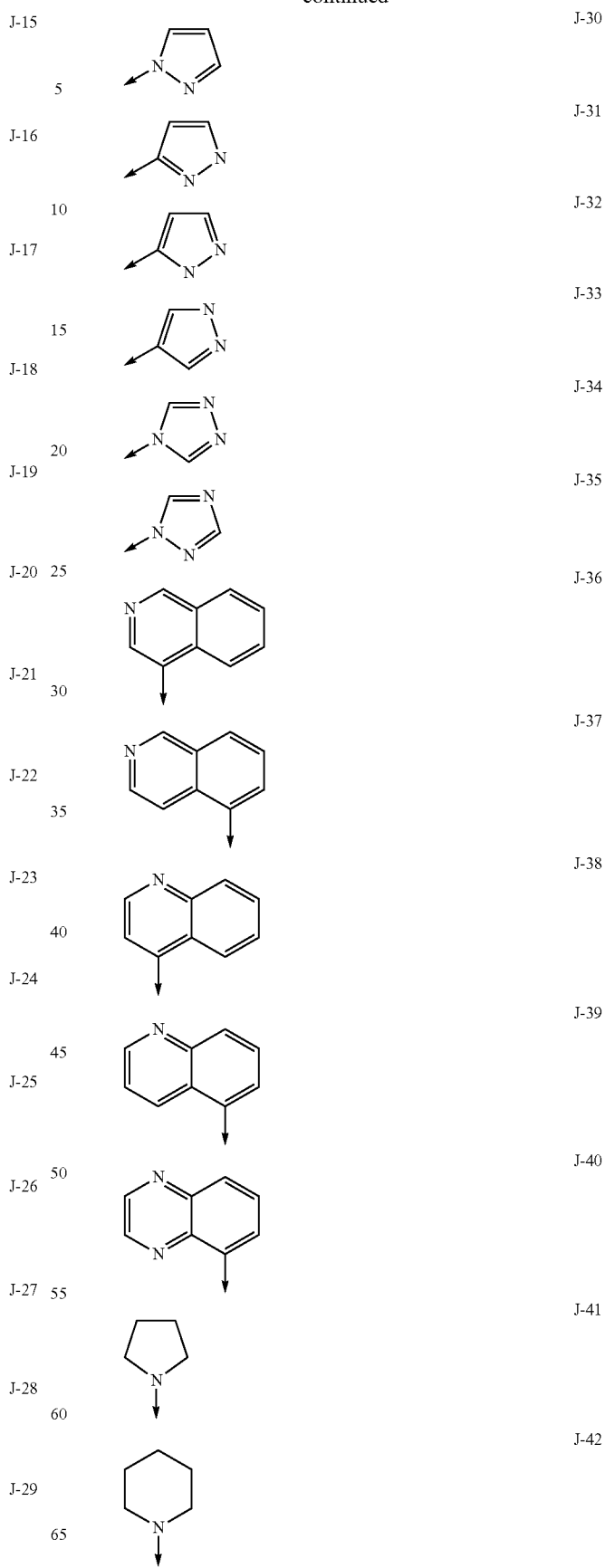

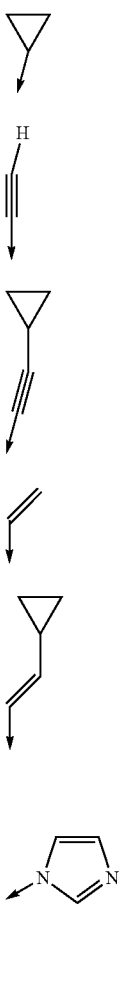

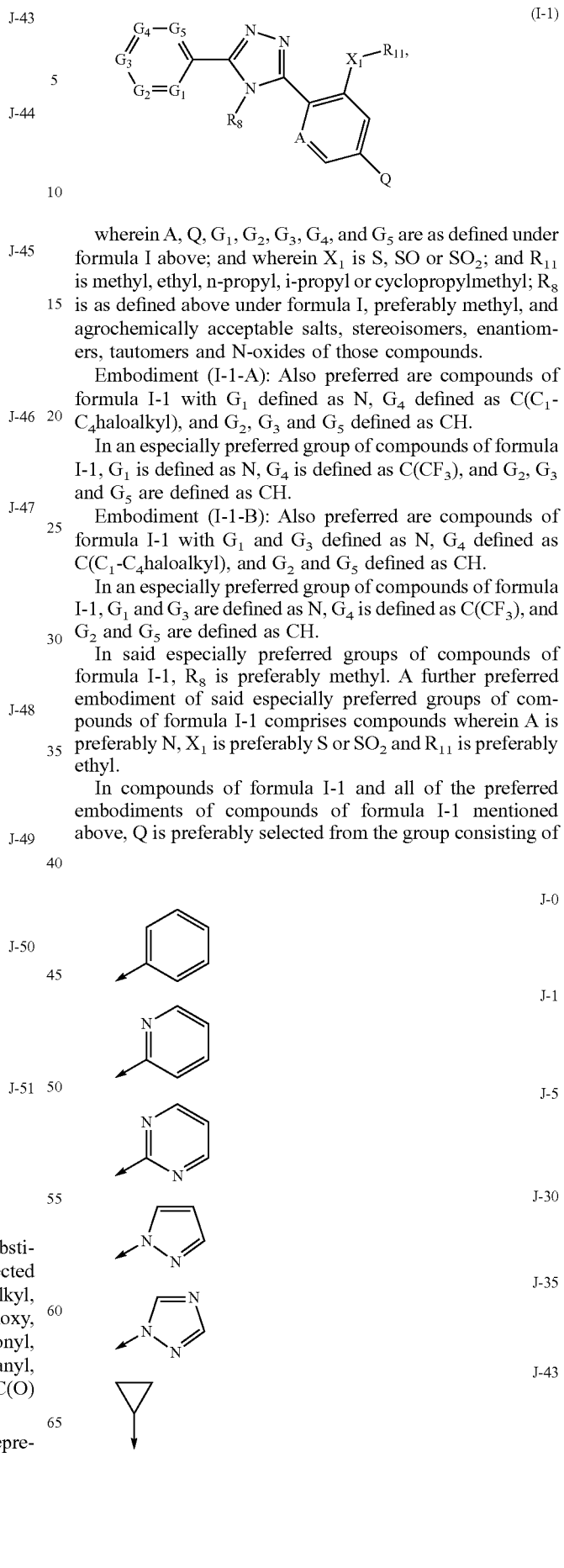

wherein A, Q, $G_1$, $G_2$, $G_3$, $G_4$, and $G_5$ are as defined under formula I above; and wherein $X_1$ is S, SO or $SO_2$; and $R_{11}$ is methyl, ethyl, n-propyl, i-propyl or cyclopropylmethyl; $R_8$ is as defined above under formula I, preferably methyl, and agrochemically acceptable salts, stereoisomers, enantiomers, tautomers and N-oxides of those compounds.

Embodiment (I-1-A): Also preferred are compounds of formula I-1 with $G_1$ defined as N, $G_4$ defined as $C(C_1$-$C_4$haloalkyl), and $G_2$, $G_3$ and $G_5$ defined as CH.

In an especially preferred group of compounds of formula I-1, $G_1$ is defined as N, $G_4$ is defined as $C(CF_3)$, and $G_2$, $G_3$ and $G_5$ are defined as CH.

Embodiment (I-1-B): Also preferred are compounds of formula I-1 with $G_1$ and $G_3$ defined as N, $G_4$ defined as $C(C_1$-$C_4$haloalkyl), and $G_2$ and $G_5$ defined as CH.

In an especially preferred group of compounds of formula I-1, $G_1$ and $G_3$ are defined as N, $G_4$ is defined as $C(CF_3)$, and $G_2$ and $G_5$ are defined as CH.

In said especially preferred groups of compounds of formula I-1, $R_8$ is preferably methyl. A further preferred embodiment of said especially preferred groups of compounds of formula I-1 comprises compounds wherein A is preferably N, $X_1$ is preferably S or $SO_2$ and $R_{11}$ is preferably ethyl.

In compounds of formula I-1 and all of the preferred embodiments of compounds of formula I-1 mentioned above, Q is preferably selected from the group consisting of in particular selected from J-1 to J-48;

wherein each group J-0 to J-48 is mono-, di- or trisubstituted with Rx, wherein each Rx is, independently selected from hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

A preferred group of compounds of formula I is represented by the compounds of formula I-1

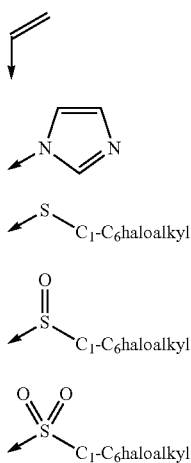

J-46

J-48

J-49

J-50 and

J-51 in particular selected from J-0, J-1, J-5, J-30, J-35, J-43, J-46 and J-48;

wherein each group J-0 to J-48 is mono-, di- or trisubstituted with Rx, wherein each Rx is, independently selected from hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl. Preferably each Rx is, independently selected from hydrogen, halogen, cyano, $C_1$-$C_4$haloalkyl and $C_1$-$C_4$alkoxy, preferably selected from hydrogen, fluorine, chlorine, cyano, trifluoromethyl and ethoxy;

in particular preferably selected from hydrogen, chlorine, cyano, trifluoromethyl and ethoxy; and wherein each $C_1$-$C_6$haloalkyl group in J-49 to J-51 is preferably trifluoromethyl.

Another preferred group of compounds of formula I is represented by the compounds of formula I-2

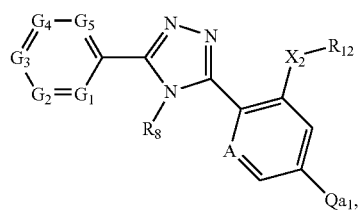

(I-2)

wherein A, $G_1$, $G_2$, $G_3$, $G_4$, and $G_5$ are as defined under formula I above; and wherein $X_2$ is S, SO or $SO_2$; and $R_{12}$ is methyl, ethyl, n-propyl, i-propyl or cyclopropylmethyl; $R_8$ is as defined above under formula I, preferably methyl, and wherein $Qa_1$ is selected from the group consisting of

J-0

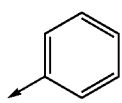

J-1

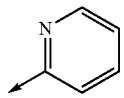

J-5

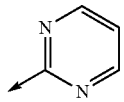

J-30

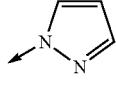

J-35

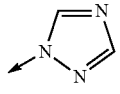

J-43

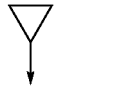

J-46

J-48

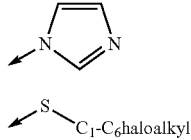

J-49

J-50

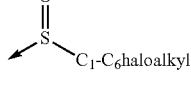

and

J-51

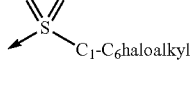

in particular selected from J-0, J-1, J-5, J-30, J-35, J-43, J-46 and J-48;

wherein each group J-0 to J-48 is mono-, di- or trisubstituted with Rx, wherein each Rx is, independently selected from hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl, and agrochemically acceptable salts, stereoisomers, enantiomers, tautomers and N-oxides of those compounds.

Also preferred are compounds of formula I-2, wherein each Rx is, independently selected from hydrogen, halogen, cyano, $C_1$-$C_4$haloalkyl and $C_1$-$C_4$alkoxy.

More preferred compounds of formula I-2 are those, in which each Rx is, independently from each other, selected from hydrogen, fluorine, chlorine, cyano, trifluoromethyl and ethoxy; in particular selected from hydrogen, chlorine, cyano, trifluoromethyl and ethoxy.

A further preferred embodiment of the invention comprises compounds of formula I-2 wherein each $C_1$-$C_6$haloalkyl group in J-49 to J-51 is preferably trifluoromethyl.

In an especially preferred group of compounds of formula I-2, $Qa_1$ is selected from the group consisting of

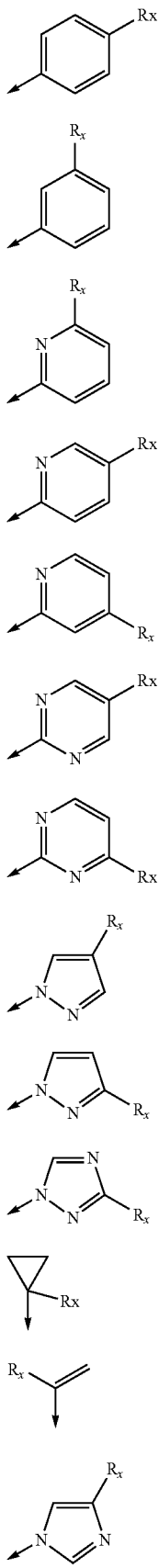

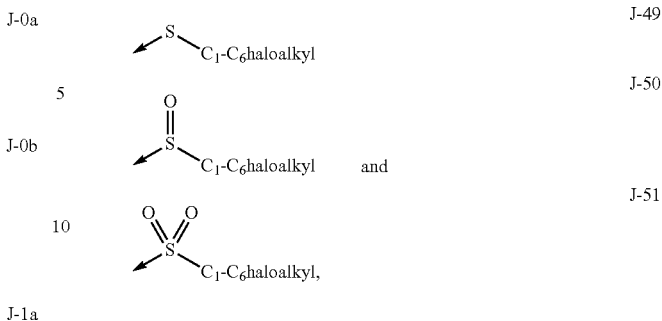

in particular selected from J-0a, J-1a, J-1b, J-1c, J-5a, J-5b, J-30a, J-30b, J-35a, J-43a, J-46a and J-48a;

wherein each Rx is, independently selected from hydrogen, halogen, cyano, $C_1$-$C_4$haloalkyl and $C_1$-$C_4$alkoxy, preferably from hydrogen, fluorine, chlorine, cyano, trifluoromethyl and ethoxy; in particular preferably selected from hydrogen, chlorine, cyano, trifluoromethyl and ethoxy; and wherein each $C_1$-$C_6$haloalkyl group in J-49 to J-51 is preferably trifluoromethyl.

In said especially preferred group of compounds of formula I-2, $R_8$ is preferably methyl. A further preferred embodiment of said especially preferred group of compounds of formula I-2 comprises compounds wherein A is preferably N, $X_2$ is preferably S or $SO_2$ and $R_{12}$ is preferably ethyl.

A further preferred embodiment of the invention comprises compounds of formula I represented by the compounds of formula I-3

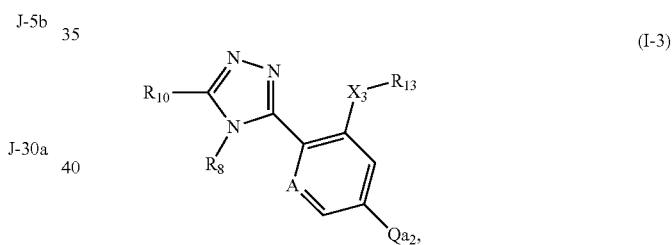

wherein

A is N or CH;

$R_{10}$ is pyridyl mono- or polysubstituted by substituents independently selected from the group consisting of $C_1$-$C_4$haloalkyl, in particular trifluoromethyl; or $R_{10}$ is pyrimidyl mono- or polysubstituted by substituents independently selected from the group consisting of $C_1$-$C_4$haloalkyl, in particular trifluoromethyl;

$X_3$ is S, SO or $SO_2$, in particular S or $SO_2$;

$Qa_2$ is selected from the group consisting of

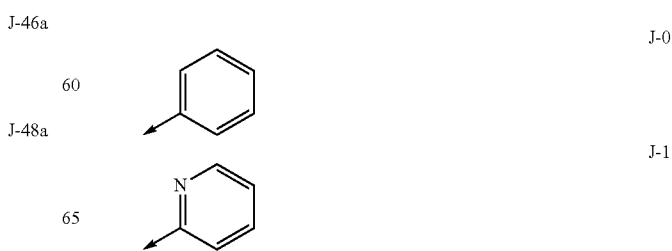

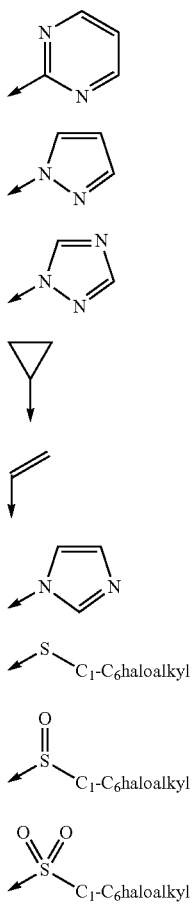
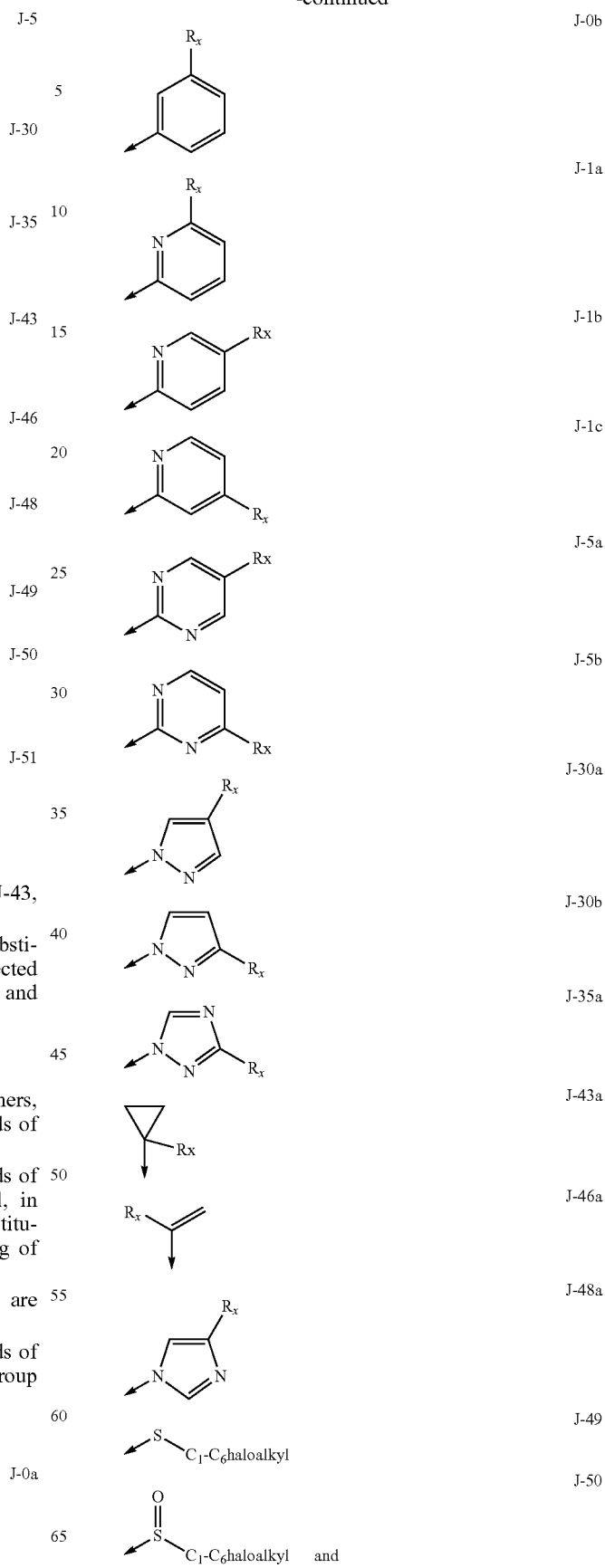

in particular selected from J-0, J-1, J-5, J-30, J-35, J-43, J-46 and J-48;

wherein each group J-0 to J-48 is mono-, di- or trisubstituted with Rx, wherein each Rx is, independently selected from hydrogen, halogen, cyano, $C_1$-$C_4$haloalkyl and $C_1$-$C_4$alkoxy;

$R_{13}$ is $C_1$-$C_4$alkyl, in particular methyl or ethyl;

$R_8$ is $C_1$-$C_4$alkyl, in particular methyl or ethyl;

and agrochemically acceptable salts, stereoisomers, enantiomers, tautomers and N-oxides of the compounds of formula I-3.

In said preferred embodiment comprising compounds of formula I-3, $R_{10}$ is preferably pyridyl or pyrimidyl, in particular preferably pyridyl, monosubstituted by substituents independently selected from the group consisting of $C_1$-$C_4$haloalkyl.

Especially preferred substituents on the ring $R_{10}$ are selected from trifluoromethyl.

In said preferred embodiment comprising compounds of formula I-3, $Qa_2$ is preferably selected from the group consisting of -continued

J-51

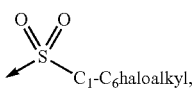

in particular selected from J-0a, J-1a, J-1b, J-1c, J-5a, J-5b, J-30a, J-30b, J-35a, J-43a, J-46a and J-48a;

wherein each Rx is, independently selected from hydrogen, halogen, cyano, $C_1$-$C_4$haloalkyl and $C_1$-$C_4$alkoxy, preferably from hydrogen, fluorine, chlorine, cyano, trifluoromethyl and ethoxy; in particular selected from hydrogen, chlorine, cyano, trifluoromethyl and ethoxy; and wherein each $C_1$-$C_6$haloalkyl group in J-49 to J-51 is preferably trifluoromethyl.

An especially preferred embodiment of the invention comprises compounds of formula I represented by the compounds of formula I-4

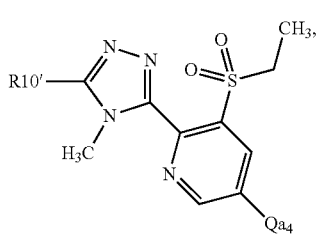

(I-4)

wherein
$R_{10}$' is pyridyl monosubstituted by $C_1$-$C_4$haloalkyl; or
$R_{10}$' is pyrimidyl monosubstituted by $C_1$-$C_4$haloalkyl;
preferably $R_{10}$' is pyridyl monosubstituted by $C_1$-$C_4$haloalkyl;
and
$Qa_4$ is selected from the group consisting of

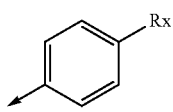

J-0a

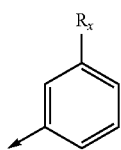

J-0b

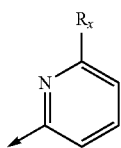

J-1a

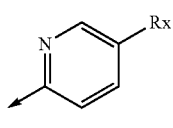

J-1b

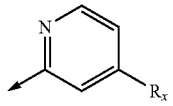

J-1c

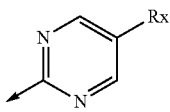

J-5a

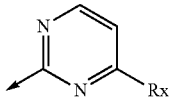

J-5b

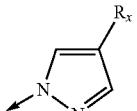

J-30a

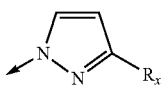

J-30b

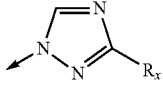

J-35a

J-43a

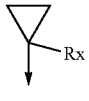

J-46a

J-48a

J-49

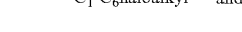

J-50 and

J-51

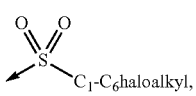

in particular selected from J-0a, J-1a, J-1b, J-1c, J-5a, J-5b, J-30a, J-30b, J-35a, J-43a, J-46a and J-48a;

wherein each Rx is, independently selected from hydrogen, halogen, cyano, $C_1$-$C_4$haloalkyl and $C_1$-$C_4$alkoxy;

and agrochemically acceptable salts, stereoisomers, enantiomers, tautomers and N-oxides of the compounds of formula I-4.

An even further especially preferred embodiment of the invention comprises compounds of formula I represented by the compounds of formula I-5

(I-5)

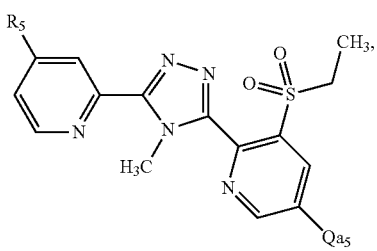

wherein $R_5$ is independently selected from the group consisting of $C_1$-$C_4$haloalkyl; and $Qa_5$ is selected from the group consisting of

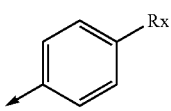 J-0a

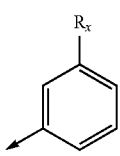 J-0b

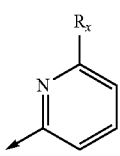 J-1a

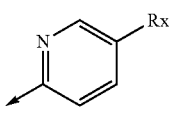 J-1b

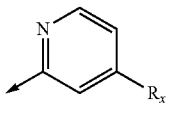 J-1c

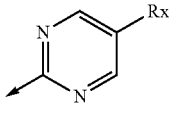 J-5a

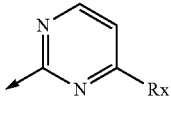 J-5b

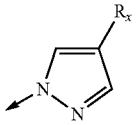 J-30a

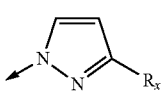 J-30b

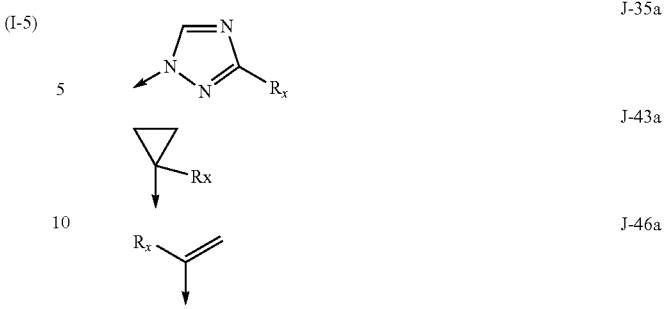

J-35a

J-43a

J-46a

J-48a

J-49

J-50

J-51

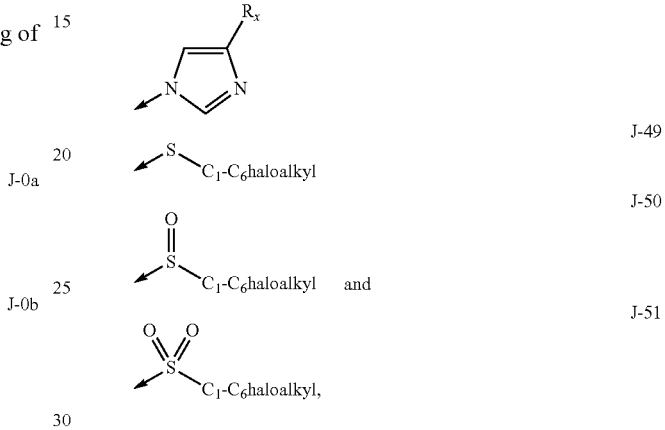

in particular selected from J-0a, J-1a, J-1b, J-1c, J-5a, J-5b, J-30a, J-30b, J-35a, J-43a, J-46a and J-48a;

wherein each Rx is, independently selected from hydrogen, halogen, cyano, $C_1$-$C_4$haloalkyl and $C_1$-$C_4$alkoxy;

and agrochemically acceptable salts, stereoisomers, enantiomers, tautomers and N-oxides of the compounds of formula I-5.

Another even further especially preferred embodiment of the invention comprises compounds of formula I represented by the compounds of formula I-6

(I-6)

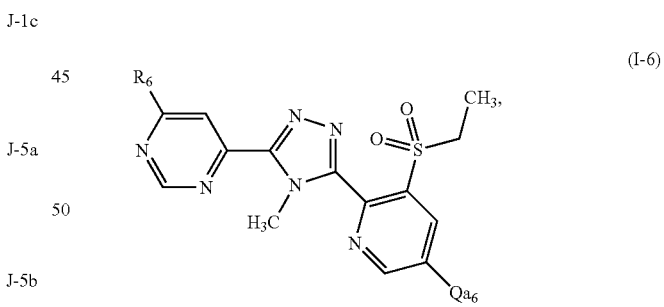

wherein $R_6$ is independently selected from the group consisting of $C_1$-$C_4$haloalkyl; and $Qa_6$ is selected from the group consisting of

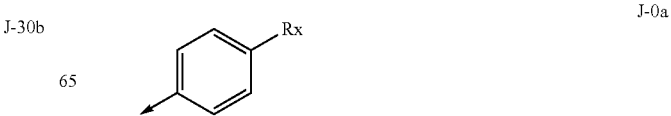 J-0a

-continued

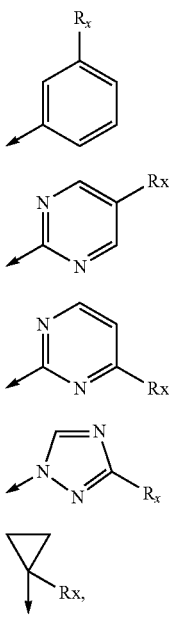

J-0b

J-5a

J-5b

J-35a

J-43a wherein each Rx is, independently selected from hydrogen, halogen and cyano;

and agrochemically acceptable salts, stereoisomers, enantiomers, tautomers and N-oxides of the compounds of formula I-6.

Another preferred group of compounds of formula I is represented by the compounds of formula I-1p

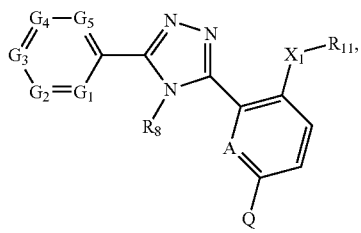

(I-1p)

wherein A, Q, $G_1$, $G_2$, $G_3$, $G_4$, and $G_5$ are as defined under formula I above; preferably Q is as defined for $Qa_5$ in formula I-5 above; and wherein $X_1$ is S, SO or $SO_2$; and $R_{11}$ is methyl, ethyl, n-propyl, propyl or cyclopropylmethyl; $R_8$ is as defined above under formula I, preferably methyl, and agrochemically acceptable salts, stereoisomers, enantiomers, tautomers and N-oxides of those compounds.

Embodiment (I-1p-A): Also preferred are compounds of formula I-1p with $G_1$ defined as N, $G_4$ defined as $C(C_1$-$C_4$haloalkyl), and $G_2$, $G_3$ and $G_5$ defined as CH.

In an especially preferred group of compounds of formula I-1p, $G_1$ is defined as N, $G_4$ is defined as $C(CF_3)$, and $G_2$, $G_3$ and $G_5$ are defined as CH.

Embodiment (I-1p-B): Also preferred are compounds of formula I-1p with $G_1$ and $G_3$ defined as N, $G_4$ defined as $C(C_1$-$C_4$haloalkyl), and $G_2$ and $G_5$ defined as CH.

In an especially preferred group of compounds of formula I-1p, $G_1$ and $G_3$ are defined as N, $G_4$ is defined as $C(CF_3)$, and $G_2$ and $G_5$ are defined as CH.

In said especially preferred groups of compounds of formula I-1p, $R_8$ is preferably methyl. A further preferred embodiment of said especially preferred groups of compounds of formula I-1p comprises compounds wherein A is preferably N, $X_1$ is preferably S or $SO_2$ and $R_{11}$ is preferably ethyl.

In compounds of formula I-1p and all of the preferred embodiments of compounds of formula I-1p mentioned above, Q is preferably selected from the group consisting of

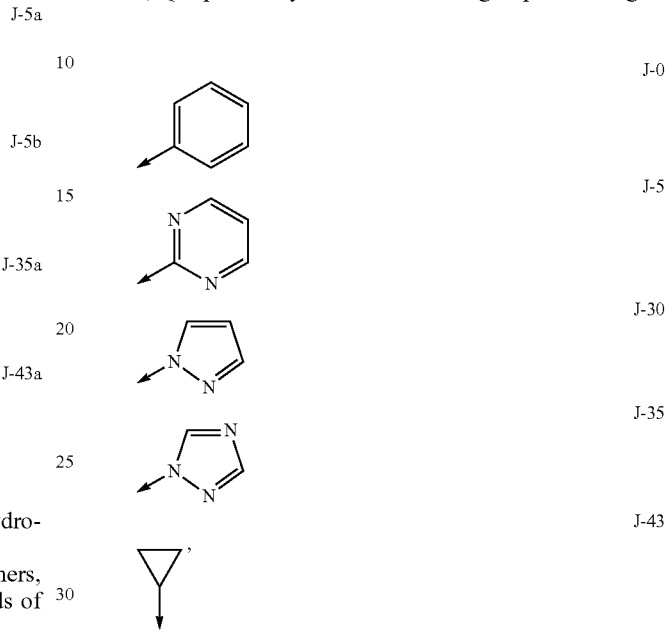

J-0

J-5

J-30

J-35

J-43 in particular selected from J-0;

wherein each group J-0 to J-43 is mono-, di- or trisubstituted with Rx, wherein each Rx is, independently selected from hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

Preferably each Rx is, independently selected from hydrogen, halogen, cyano and $C_1$-$C_4$haloalkyl, in particular selected from hydrogen and $C_1$-$C_4$haloalkyl; more preferably each Rx is, independently selected from hydrogen, fluorine, chlorine, cyano and trifluoromethyl, in particular selected from hydrogen and trifluoromethyl.

Another preferred group of compounds of formula I is represented by the compounds of formula I-2p

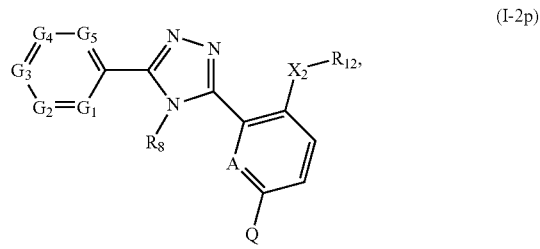

(I-2p)

wherein A, Q, $G_1$, $G_2$, $G_3$, $G_4$, and $G_5$ are as defined under formula I above; preferably Q is as defined for $Qa_5$ in formula I-5 above; and wherein $X_2$ is S, SO or $SO_2$; and $R_{12}$ is methyl, ethyl, n-propyl, propyl or cyclopropylmethyl; $R_8$ is as defined above under formula I, preferably methyl, and wherein Q is selected from the group consisting of

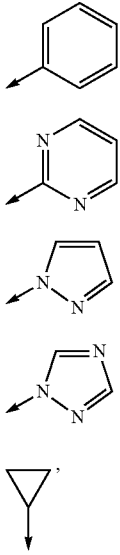

J-0

J-5

J-30

J-35

J-43 in particular selected from J-0;

wherein each group J-0 to J-43 is mono-, di- or trisubstituted with Rx, wherein each Rx is, independently selected from hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl, and agrochemically acceptable salts, stereoisomers, enantiomers, tautomers and N-oxides of those compounds.

Also preferred are compounds of formula I-2p, wherein each Rx is, independently selected from hydrogen, halogen, cyano and $C_1$-$C_4$haloalkyl, in particular selected from hydrogen and $C_1$-$C_4$haloalkyl.

More preferred compounds of formula I-2p are those, in which each Rx is, independently from each other, selected from hydrogen, fluorine, chlorine, cyano and trifluoromethyl, in particular selected from hydrogen and trifluoromethyl.

In an especially preferred group of compounds of formula I-2p, Q is selected from the group consisting of

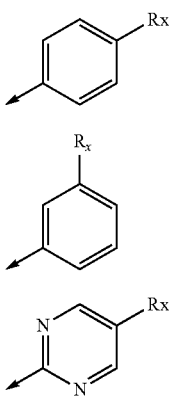

J-0a

J-0b

J-5a

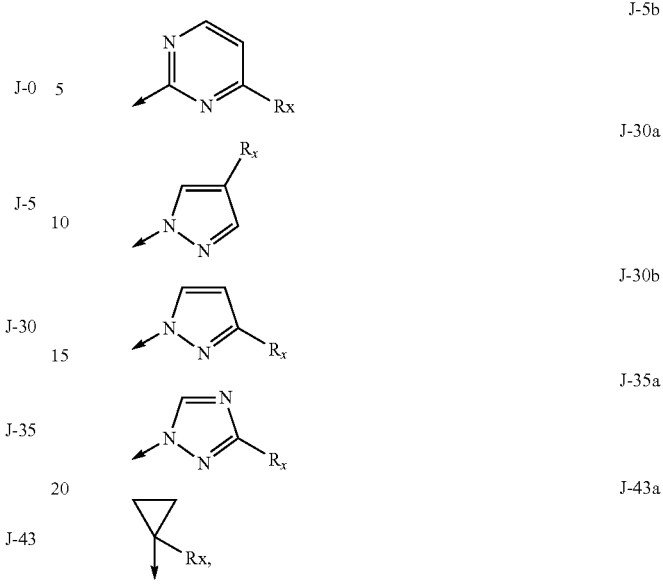

J-5b

J-30a

J-30b

J-35a

J-43a in particular selected from J-0a;

wherein each Rx is, independently selected from hydrogen, halogen, cyano and $C_1$-$C_4$haloalkyl, in particular selected from hydrogen and $C_1$-$C_4$haloalkyl; more preferably each Rx is, independently selected from hydrogen, fluorine, chlorine, cyano and trifluoromethyl, in particular selected from hydrogen and trifluoromethyl.

In said especially preferred group of compounds of formula I-2p, $R_8$ is preferably methyl. A further preferred embodiment of said especially preferred group of compounds of formula I-2p comprises compounds wherein A is preferably N, $X_2$ is preferably S or $SO_2$ and $R_{12}$ is preferably ethyl.

A further preferred embodiment of the invention comprises compounds of formula I represented by the compounds of formula I-3p

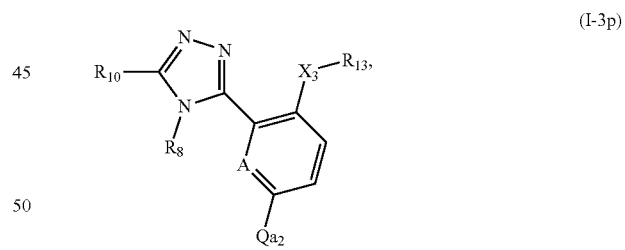

(I-3p)

wherein
A is N or CH;
$R_{10}$ is pyridyl or pyrimidyl mono- or polysubstituted by substituents independently selected from the group consisting of $C_1$-$C_4$haloalkyl, in particular trifluoromethyl;
$X_3$ is S, SO or $SO_2$, in particular S or $SO_2$;
$Qa_2$ is selected from the group consisting of

J-0

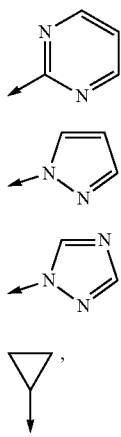

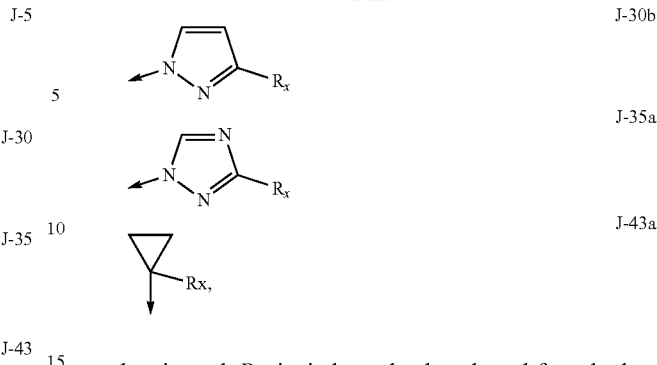

wherein each group J-0 to J-43 is mono-, di- or trisubstituted with Rx, wherein each Rx is, independently selected from hydrogen, halogen, cyano and $C_1$-$C_4$haloalkyl;

$R_{13}$ is $C_1$-$C_4$alkyl, in particular methyl or ethyl;

$R_8$ is $C_1$-$C_4$alkyl, in particular methyl or ethyl;

and agrochemically acceptable salts, stereoisomers, enantiomers, tautomers and N-oxides of the compounds of formula I-3p.

In said preferred embodiment comprising compounds of formula I-3p, $R_{10}$ is preferably pyridyl or pyrimidyl monosubstituted by substituents independently selected from the group consisting of $C_1$-$C_4$haloalkyl.

Especially preferred substituents on the ring $R_{10}$ are selected from trifluoromethyl.

In said preferred embodiment comprising compounds of formula I-3p, $Qa_2$ is preferably selected from the group consisting of

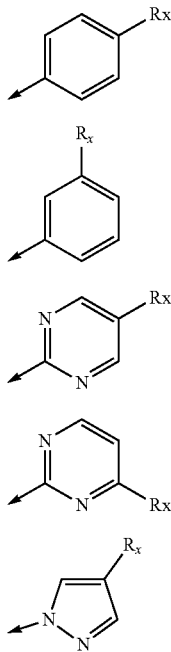

wherein each Rx is, independently selected from hydrogen, halogen, cyano and $C_1$-$C_4$haloalkyl, preferably from hydrogen, fluorine, chlorine, cyano and trifluoromethyl.

An especially preferred embodiment of the invention comprises compounds of formula I represented by the compounds of formula I-4p

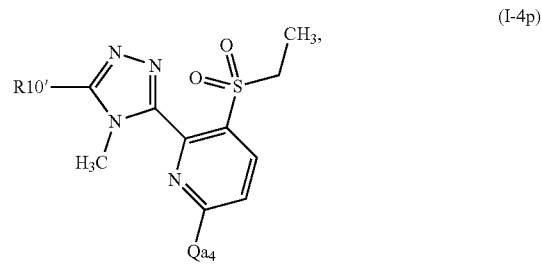

wherein
$R_{10}'$ is pyridyl or pyrimidyl monosubstituted by substituents independently selected from the group consisting of $C_1$-$C_4$haloalkyl; and
$Qa_4$ is selected from the group consisting of

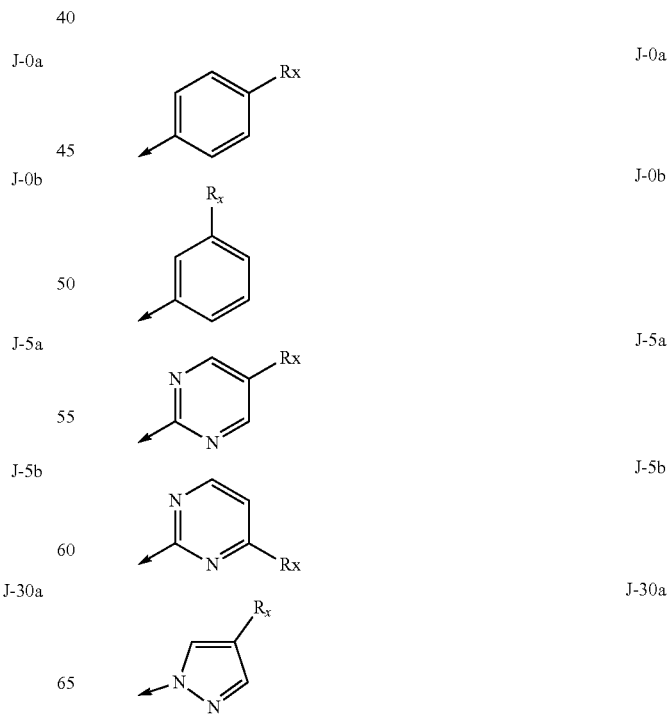

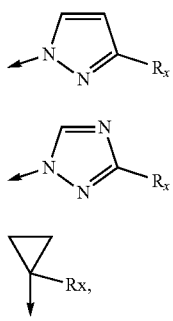

J-30b

J-35a

J-43a wherein each Rx is, independently selected from hydrogen, halogen, cyano and $C_1$-$C_4$haloalkyl;

and agrochemically acceptable salts, stereoisomers, enantiomers, tautomers and N-oxides of the compounds of formula I-4p.

An even further especially preferred embodiment of the invention comprises compounds of formula I represented by the compounds of formula I-5p

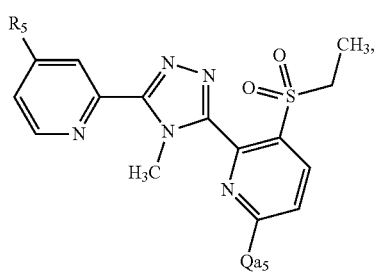

(I-5p)

wherein $R_5$ is independently selected from the group consisting of $C_1$-$C_4$haloalkyl; and $Qa_5$ is selected from the group consisting of

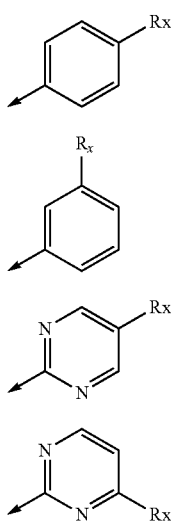

J-0a

J-0b

J-5a

J-5b

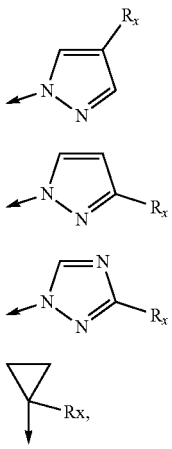

J-30a

J-30b

J-35a

J-43a wherein each Rx is, independently selected from hydrogen, halogen, cyano and $C_1$-$C_4$haloalkyl;

and agrochemically acceptable salts, stereoisomers, enantiomers, tautomers and N-oxides of the compounds of formula I-5p.

Another even further especially preferred embodiment of the invention comprises compounds of formula I represented by the compounds of formula I-6p

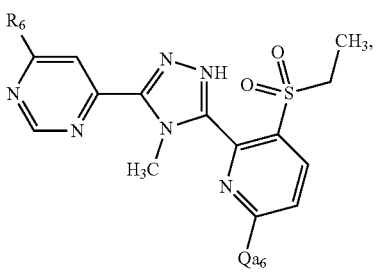

(I-6p)

wherein $R_6$ is independently selected from the group consisting of $C_1$-$C_4$haloalkyl; and $Qa_6$ is selected from the group consisting of J-0a J-0b J-5a -continued

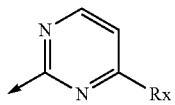
J-5b

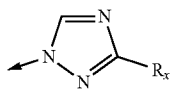
J-35a

J-43a wherein each Rx is, independently selected from hydrogen, halogen, cyano and $C_1$-$C_4$haloalkyl;

and agrochemically acceptable salts, stereoisomers, enantiomers, tautomers and N-oxides of the compounds of formula I-6p.

The process according to the invention for preparing compounds of formula I is carried out in principle by methods known to those skilled in the art. More specifically, the subgroup of compounds of formula I, wherein X is SO (sulfoxide) and/or $SO_2$ (sulfone), may be obtained by means of an oxidation reaction of the corresponding sulfide compounds of formula I, wherein X is S, involving reagents such as, for example, m-chloroperoxybenzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. The amount of the oxidant to be used in the reaction is generally 1 to 3 moles, preferably 1 to 1.2 moles, relative to 1 mole of the sulfide compounds I to produce the sulfoxide compounds I, and preferably 2 to 2.2 moles of oxidant, relative to 1 mole of the sulfide compounds I to produce the sulfone compounds I. Such oxidation reactions are disclosed, for example, in WO 2013/018928.

The subgroup of compounds of formula I, wherein X is S (sulfide) and wherein $R_7$, $R_8$, $G_1$, $G_2$, $G_3$, $G_4$, and $G_5$ are as defined above,

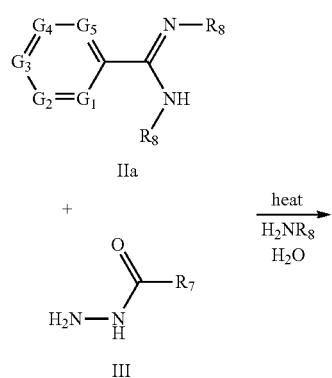

may be prepared by reacting an amidine compound of formula IIa, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above, with a hydrazide compound of formula III, or a salt thereof, wherein $R_7$ is as defined above and wherein X is S (sulfide), optionally in presence of a base such as alkali metal carbonates, for example sodium carbonate or potassium carbonate, in a solvent such as methanol, ethanol, isopropanol, acetonitrile, pyridine, acetic acid, N,N-dimethyl-formamide or N,N-dimethylacetamide, at temperatures between 0 and 200° C., preferably between 50 and 150° C., optionally under microwave irradiation. Such a process may be carried out in analogy to, for example, G. Bonanomi et al., ChemMedChem 2010, 5, 705-715. The compounds of formula IIa may be reacted with any configuration (E or Z, or any mixture thereof) on the carbon-nitrogen double bond.

Alternatively, the subgroup of compounds of formula I, wherein X is S (sulfide) and wherein $R_7$, $R_8$, $G_1$, $G_2$, $G_3$, $G_4$, and $G_5$ are as defined above,

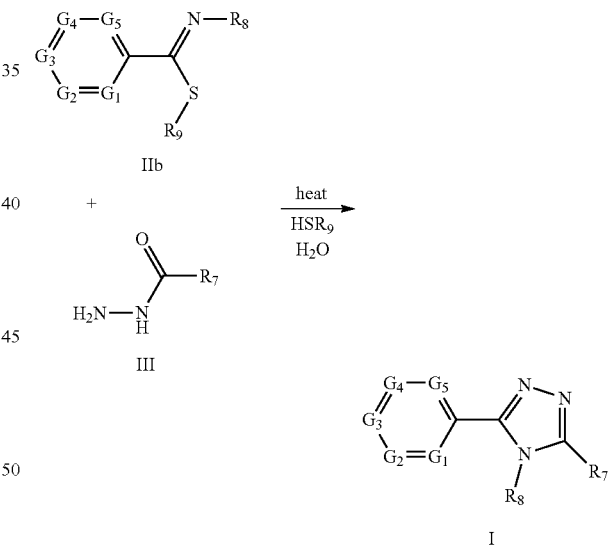

may be prepared by reacting an alkyl carboximidothioate compound of formula IIb, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above, and in which $R_9$ is $C_{1-6}$alkyl, with a hydrazide compound of formula III, or a salt thereof, wherein $R_7$ is as defined above and wherein X is S (sulfide), optionally in presence of a base such as alkali metal carbonates, for example sodium carbonate or potassium carbonate, in a solvent such as methanol, ethanol, isopropanol, acetonitrile, pyridine, acetic acid, N,N-dimethylformamide or N,N-dimethyl-acetamide, at temperatures between 0 and 200° C., preferably between 50 and 180° C., optionally under microwave irradiation. Such a process may be carried out in analogy to, for example, M. H. Klingele et al, Eur. J. Org. Chem. 2004, 3422-3434. The compounds of formula IIb may be reacted with any configuration (E or Z, or any mixture thereof) on the carbon-nitrogen double bond.

Compounds of formula IIa, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above,

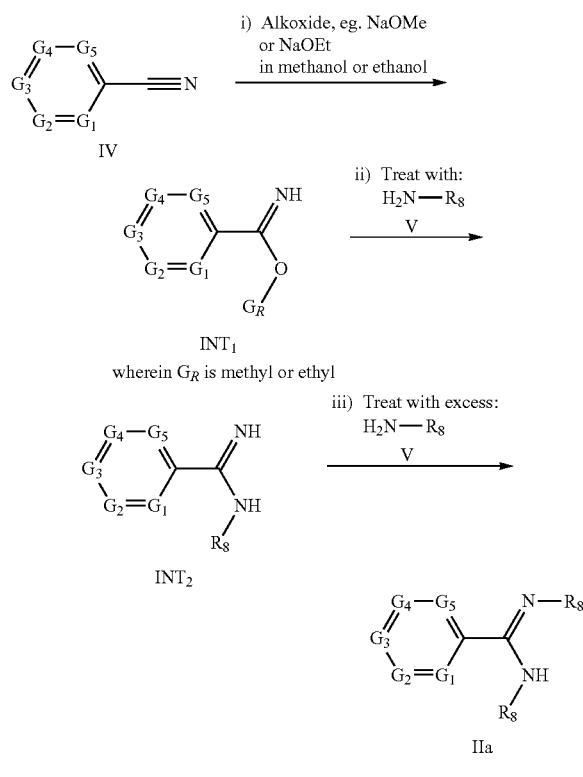

may be prepared by reacting a nitrile compound of formula IV, wherein $G_1$, $G_2$, $G_3$, $G_4$, and $G_5$ are as defined above, sequentially with i) a catalytic amount (preferably 0.01 to 0.5 equivalent) or an equimolar amount of an alkoxide, preferably sodium methoxide NaOMe or sodium ethoxide NaOEt, in an alcoholic solvent, such as methanol or ethanol, at temperatures between 0 and 100° C., to generate an imidate intermediate of the formula $INT_1$ (or a salt and/or a tautomer thereof); followed by ii) treatment with an amine reagent of formula V $$R_8\text{—}NH_2 \quad (V),$$

or a salt thereof (such as a hydrohalide salt, preferably a hydrochloride or a hydrobromide salt, or any other equivalent salt), wherein $R_8$ is as defined above, optionally in the presence of an acid (such as a hydrohalide acid, preferably hydrochloric acid or hydrobromic acid, or any other equivalent acid), at temperatures between 0-180° C., to generate an amidine intermediate of the formula $INT_2$ (or a salt and/or a tautomer thereof); followed by iii) treatment with an excess of the amine reagent of formula V, or a salt thereof (such as a hydrohalide salt, preferably a hydrochloride or a hydrobromide salt, or any other equivalent salt), wherein $R_8$ is as defined above, preferably in the presence of an acid (such as a hydrohalide acid, preferably hydrochloric acid or hydrobromic acid, or any other equivalent acid), at temperatures between 0-180° C., to form the compound of the formula IIa, or a salt and/or a tautomer thereof. The compounds of formula IIa may be isolated with any configuration (E or Z, or any mixture thereof) on the carbon-nitrogen double bond. Steps ii) and iii) may be combined, for example to allow a direct formation of a compound of formula IIa from a compound of formula $INT_1$. Steps ii) and/or iii) may also be performed under microwave irradiation, each optionally also in a pressurized vessel. Compounds of the formula $INT_1$ may alternatively be prepared under conditions and variants of the Pinner reaction known to a person skilled in the art, typically by treating a compound of the formula IV with a hydrohalide acid, preferably hydrochloric acid, in presence of alcoholic reagents such as methanol or ethanol, preferably in an inert solvent such as diethyl ether, tetrahydrofuran or dioxane, at temperatures between −40 and 50° C., preferably between −20 and 20° C. The described process to prepare compounds of the formula IIa from compounds of the formula IV may include isolation and purification of the intermediates $INT_1$ and/or $INT_2$ (which may be isolated as free bases or as salts (e.g. a hydrohalide salt, more specifically a hydrochloride or hydrobromide salt, or any other equivalent salt)), however this process is advantageously conducted as a one-pot preparation. In the particular situation where $R_8$ is methyl or ethyl, the amine reagent of formula V may be engaged in the above reaction as a gas, as a salt (such as a hydrohalide salt, preferably a hydrochloride or a hydrobromide salt, or any other equivalent salt), or as a solution in solvents such as methanol, ethanol, tetrahydrofuran or water.

Compounds of formula IIb, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above, and in which $R_9$ is $C_{1-6}$alkyl,

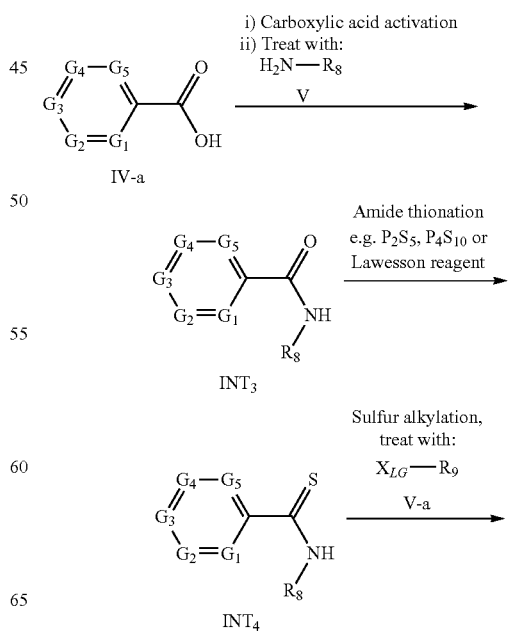

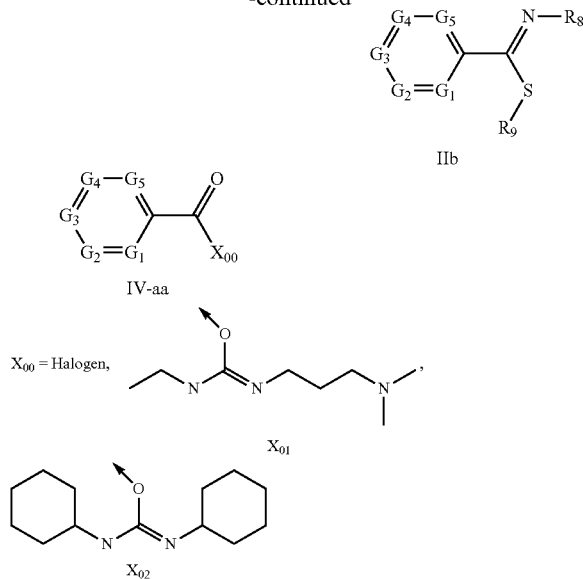

may be prepared by reacting a compound of formula INT$_4$, wherein R$_8$, G$_1$, G$_2$, G$_3$, G$_4$, and G$_5$ are as defined above, with an alkylation reagent of formula V-a, wherein R$_9$ is C$_{1-6}$alkyl, and in which X$_{LG}$ is a leaving group, such as a halogen (especially bromine or iodine), or a leaving group OSO$_2$R$_{38}$, wherein R$_{38}$ is C$_1$-C$_6$alkyl, C$_1$-C$_6$haloalkyl, or phenyl optionally substituted by nitro or C$_1$-C$_3$alkyl (especially a sulfonate such as mesylate, triflate or tosylate) or a sulfate (forming for example the alkylating agent V-a dimethylsulfate, in the particular situation where R$_9$ is methyl), preferably in the presence of a suitable base, such as sodium hydride or sodium, potassium or cesium carbonate, in an inert solvent such as tetrahydrofuran, dioxane, acetonitrile, N,N-dimethylformamide, N,N-dimethylacetamide, N-methyl-2-pyrrolidone or dimethyl sulfoxide. Another advantageous base/solvent combination for this transformation is also, for example, an alkoxide, preferably sodium methoxide NaOMe or sodium ethoxide NaOEt, in an alcoholic solvent, such as methanol or ethanol, at temperatures between 0-100° C., preferably around room temperature. The compounds of formula IIb may be isolated with any configuration (E or Z, or any mixture thereof) on the carbon-nitrogen double bond. Such a process may be carried out in analogy to, for example, M. H. Klingele et al, Eur. J. Org. Chem. 2004, 3422-3434.

Compounds of formula INT$_4$, wherein R$_8$, G$_1$, G$_2$, G$_3$, G$_4$, and G$_5$ are as defined above, may be prepared by reacting a compound of formula INT$_3$, wherein R$_8$, G$_1$, G$_2$, G$_3$, G$_4$, and G$_5$ are as defined above, with a thionation agent, such as phosphorus decasulfide P$_4$S$_{10}$ (also called phosphorus pentasulfide P$_2$S$_5$), or the Lawesson reagent (2,4-bis(4-methoxyphenyl)-1,3,2,4-dithiadiphosphetane-2,4-dithione), in inert solvents such as toluene, xylene, tetrahydrofuran, dioxane or pyridine, at temperatures between 0-200° C., preferably between 50 and 150° C., optionally under microwave irradiation. Such a process may be carried out in analogy to, for example, T. Ozturk et al., Chem. Rev. 2010, 110, 3419-3478.

Compounds of formula INT$_3$, wherein R$_8$, G$_1$, G$_2$, G$_3$, G$_4$, and G$_5$ are as defined above, may be prepared by i) activation of a compound of formula IV-a, wherein G$_1$, G$_2$, G$_3$, G$_4$, and G$_5$ are as defined above, by methods known to those skilled in the art and described in, for example, Tetrahedron, 2005, 61 (46), 10827-10852, to form an activated species IV-aa, wherein G$_1$, G$_2$, G$_3$, G$_4$, and G$_5$ are as defined above and wherein X$_{00}$ is halogen, preferably chlorine. For example, compounds IV-aa where X$_{00}$ is halogen, preferably chlorine, are formed by treatment of IV-a with, for example, oxallyl chloride (COCl)$_2$ or thionyl chloride SOCl$_2$ in the presence of catalytic quantities of N,N-dimethylformamide DMF in inert solvents such as methylene chloride CH$_2$Cl$_2$ or tetrahydrofuran THF at temperatures between 20 to 100° C., preferably 25° C. Alternatively, treatment of compounds of formula IV-a with, for example, 1-ethyl-3-(3-dimethylaminopropyl)carbodiimide EDC or dicyclohexyl carbodiimide DCC will generate an activated species IV-aa, wherein X$_{00}$ is X$_{01}$ or X$_{02}$ respectively, in an inert solvent, such as pyridine or tetrahydrofuran THF, optionally in the presence of a base, such as triethylamine, at temperatures between 50-180° C.; followed by ii) treatment of the activated species IV-aa with an amine reagent of formula V $$R_8-NH_2 \quad (V),$$

or a salt thereof (such as a hydrohalide salt, preferably a hydrochloride or a hydrobromide salt, or any other equivalent salt), wherein R$_8$ is as defined above, optionally in the presence of a base, such as triethylamine or pyridine, in an inert solvents such as dichloromethane, tetrahydrofuran, dioxane or toluene, at temperatures between 0 and 50° C., to form the compounds of formula INT$_3$. Certain bases, such as pyridine and triethylamine, may be employed successfully as both base and solvent.

Compounds of formula IV and compounds of formula IV-a, wherein G$_1$, G$_2$, G$_3$, G$_4$, and G$_5$ are as defined above, are known compounds or can be prepared by known methods, described in the literature.

Compounds of the formula III, or a salt thereof, wherein R$_7$ is as defined above,

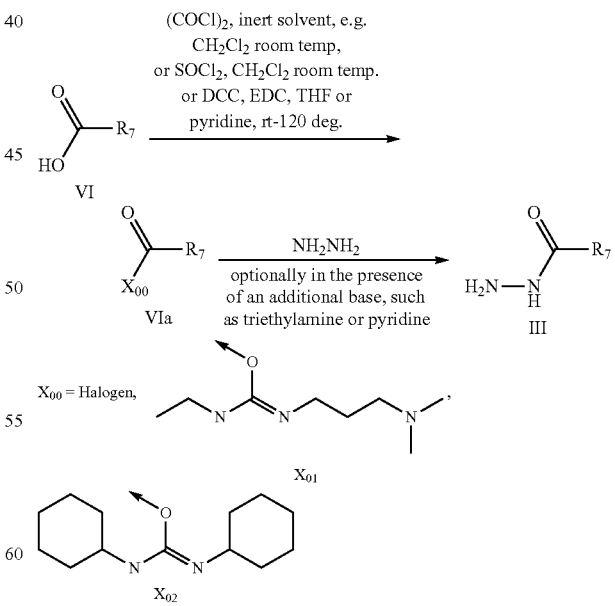

may be prepared by i) activation of compound of formula VI, wherein R$_7$ is as defined above, by methods known to those skilled in the art and described in, for example, Tetrahedron, 2005, 61 (46), 10827-10852, to form an activated species VIa, wherein $R_7$ is as defined above and wherein $X_{00}$ is halogen, preferably chlorine. For example, compounds VIa where $X_{00}$ is halogen, preferably chlorine, are formed by treatment of VI with, for example, oxallyl chloride $(COCl)_2$ or thionyl chloride $SOCl_2$ in the presence of catalytic quantities of N,N-dimethylformamide DMF in inert solvents such as methylene chloride $CH_2Cl_2$ or tetrahydrofuran THF at temperatures between 20 to 100° C., preferably 25° C. Alternatively, treatment of compounds of formula VI with, for example, 1-ethyl-3-(3-dimethylaminopropyl)carbodiimide EDC or dicyclohexyl carbodiimide DCC will generate an activated species VIa, wherein $X_{00}$ is $X_{01}$ or $X_{02}$ respectively, in an inert solvent, such as pyridine or tetrahydrofuran THF, optionally in the presence of a base, such as triethylamine, at temperatures between 50-180° C.; followed by ii) Treatment of the activated species VIa with hydrazine $NH_2NH_2$ (or a salt thereof), possibly in form of a hydrate, preferably hydrazine monohydrate, optionally in the presence of a base, such as triethylamine or pyridine, in an inert solvents such as dichloromethane, tetrahydrofuran, dioxane or toluene, at temperatures between 0 and 50° C., to form the compounds of formula III.

Alternatively, compounds of the formula III, or a salt thereof, wherein $R_7$ is as defined above, may be prepared by the direct action of hydrazine (or a salt thereof), possibly in form of a hydrate, preferably hydrazine monohydrate, on an ester derivative VIb (VIb)

of the compound of formula VI, wherein $R_7$ is as defined above and wherein $R_{00}$ is $C_1$-$C_4$alkyl, preferably methyl or ethyl, at temperatures between 20 and 150° C. This reaction is preferably performed in an alcoholic solvent, such as methanol or ethanol. Such a process description may be found, for example, in M. H. Klingele et al, Eur. J. Org. Chem. 2004, 3422-3434.

Compounds of formula VI and VIb, wherein $R_7$ is as defined above, are known compounds or can be prepared by known methods (see in particular, preparation of useful building blocks of formula XIX described below), described in the literature. In particular, ester compounds of formula VIb, wherein $R_7$ is as defined above and wherein $R_{00}$ is $C_1$-$C_4$alkyl, may be prepared from the corresponding carboxylic acid compounds of formula VI, wherein $R_7$ is as defined above, by reaction with an alcohol of formula $R_{00}OH$ (XII), wherein $R_{00}$ is $C_1$-$C_4$alkyl, optionally in the presence of an acid (such as sulfuric acid), or alternatively optionally in presence of an activating agent, such as for example oxalyl chloride $(COCl)_2$. Such esterification methods are well known to a person skilled in the art.

Compounds of formula I, wherein $R_7$, $R_8$, $G_1$, $G_2$, $G_3$, $G_4$, and $G_5$ are as defined in formula I and wherein X is S (sulfide),

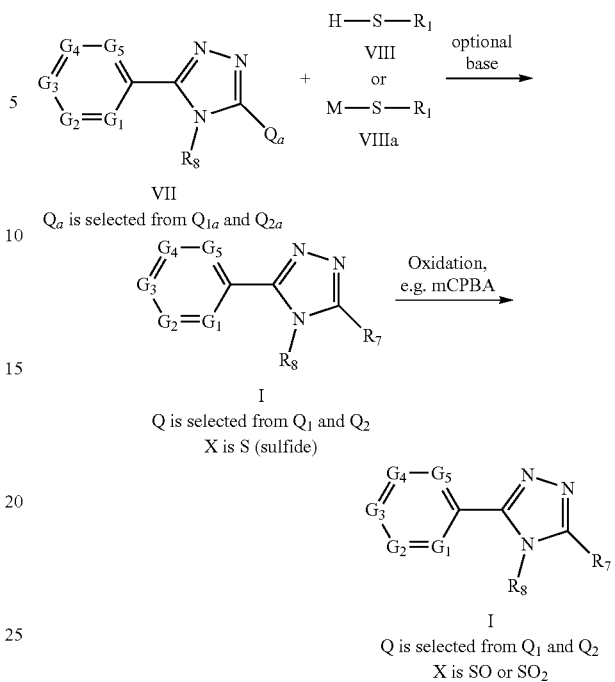

can also be prepared by reacting a compound of formula VII, wherein $R_8$, $G_1$, $G_2$, $G_3$, $G_4$, and $G_5$ are as described in formula I and wherein $Q_a$ is a radical selected from the group consisting of formula $Q_{1a}$ to $Q_{2a}$:

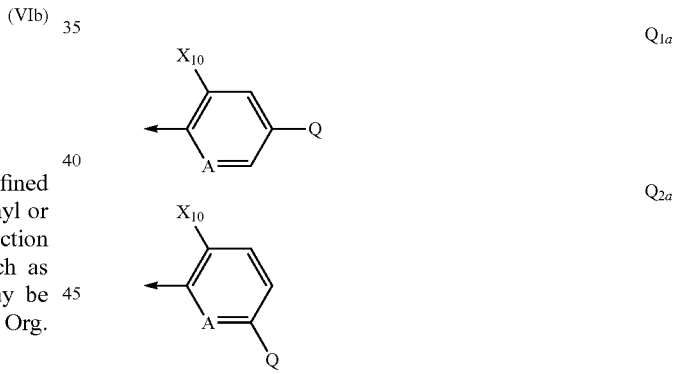

wherein A is as defined in formula I, and wherein $X_{10}$ is a halogen (preferably fluorine, chlorine or bromine), with a compound of formula VIII $R_1$—SH    (VIII), or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Examples of salts of the compound of formula VIII include compounds of the formula VIIIa $$R_1\text{—S—M} \qquad \text{(VIIIa)}$$

wherein $R_1$ is as defined above and wherein M is, for example, sodium or potassium.

Compounds of formula VII, wherein $R_8$, $G_1$, $G_2$, $G_3$, $G_4$, and $G_5$ are as defined above, and wherein $Q_a$ is a radical selected from the group consisting of formula $Q_{1a}$ to $Q_{2a}$ described above,

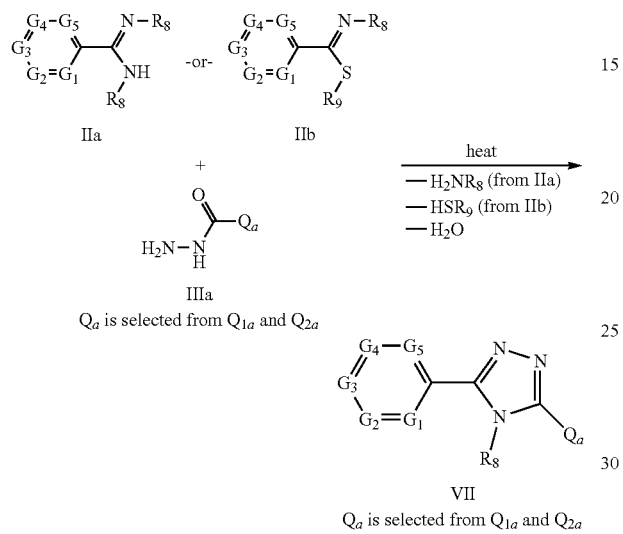

may be prepared by reacting an amidine compound of formula IIa, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above;

or alternatively, by reacting an alkyl carboximidothioate compound of formula IIb, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above, and in which $R_9$ is $C_{1-6}$alkyl; with a hydrazide compound of formula IIIa, or a salt thereof, wherein $Q_a$ is a radical selected from the group consisting of formula $Q_{1a}$ to $Q_{2a}$ described above, optionally in presence of a base such as alkali metal carbonates, for example sodium carbonate or potassium carbonate, in a solvent such as methanol, ethanol, isopropanol, acetonitrile, pyridine, acetic acid, N,N-dimethylformamide or N,N-dimethylacetamide, at temperatures between 0 and 200° C., preferably between 50 and 180° C., optionally under microwave irradiation. The compounds of formula IIa or IIb may be reacted with any configuration (E or Z, or any mixture thereof) on the carbon-nitrogen double bond.

Compounds of formula IIIa, or a salt thereof, wherein $Q_a$ is as defined above, may be prepared in analogy to processes described above in the context of the preparation of compounds of the formula III as described in scheme 1.

Scheme 1:

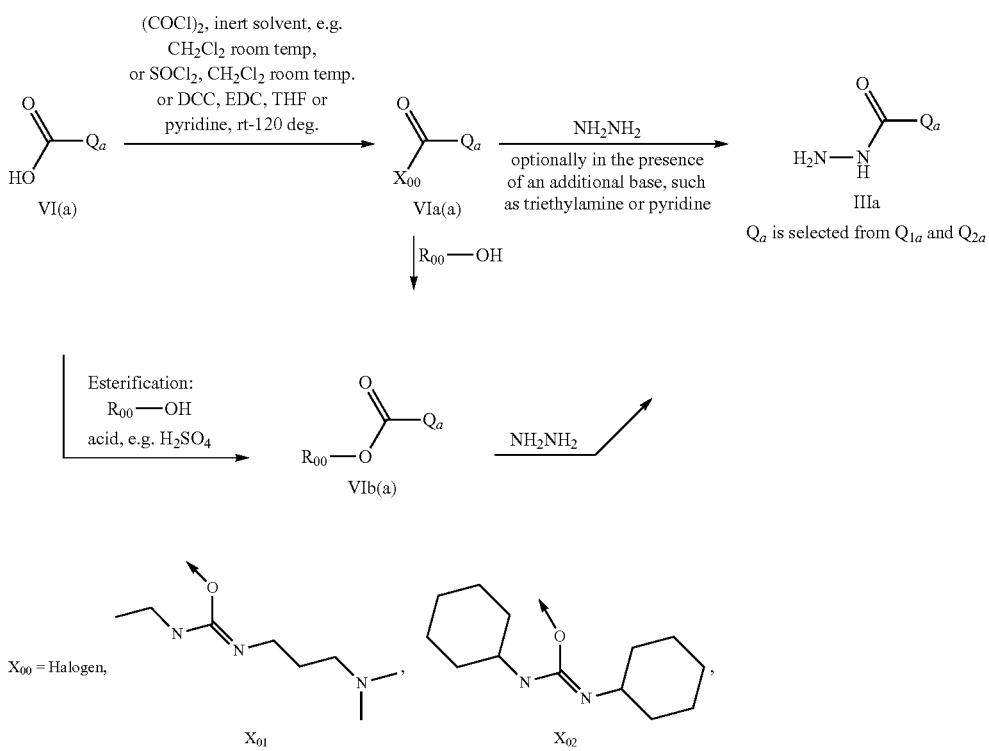

Compounds of formula VI(a) and VIb(a), wherein $Q_a$ and $R_{00}$ are as defined above, are known compounds or can be prepared by known methods, described in the literature.

The subgroup of compounds of formula I, wherein $R_8$, $G_1$, $G_2$, $G_3$, $G_4$, and $G_5$ are as defined above and wherein $R_7$ is defined as $Q_1$, in which A, Q, X and $R_1$ are as defined above, may be defined as compounds of formula I-$Q_1$. Compounds of formula I-$Q_1$, wherein X is SO or $SO_2$, Scheme 2:

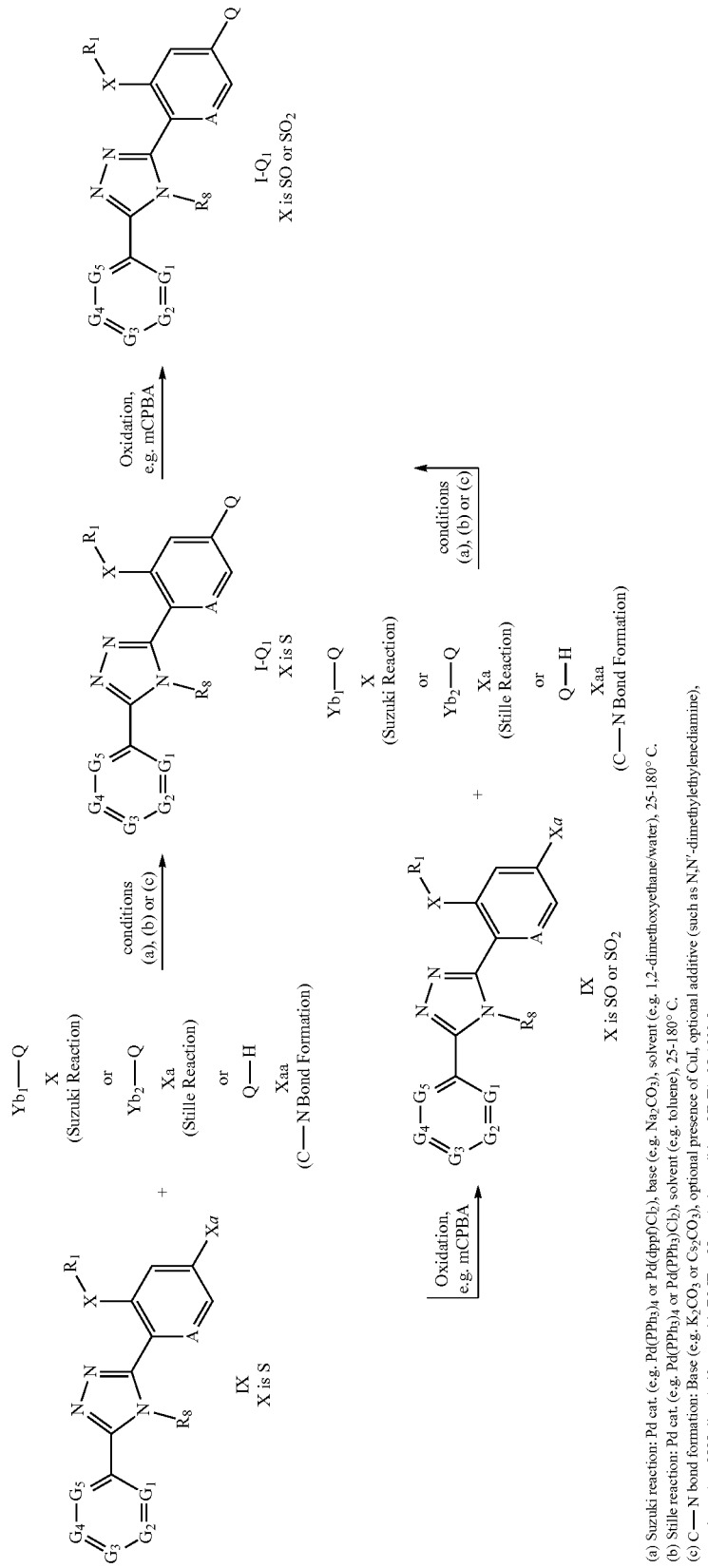

(a) Suzuki reaction: Pd cat. (e.g. Pd(PPh₃)₄ or Pd(dppf)Cl₂), base (e.g. Na₂CO₃), solvent (e.g. 1,2-dimethoxyethane/water), 25-180° C.
(b) Stille reaction: Pd cat. (e.g. Pd(PPh₃)₄ or Pd(PPh₃)₂Cl₂), solvent (e.g. toluene), 25-180° C.
(c) C—N bond formation: Base (e.g. K₂CO₃ or Cs₂CO₃), optional presence of CuI, optional additive (such as N,N'-dimethylethylenediamine), solvent (e.g. N,N-dimethylformamide DMF or N-methylpyrrolidone NMP), 25-180° C.

may be prepared by a Suzuki reaction (scheme 2), which involves for example, reacting compounds of formula IX, wherein A, $R_1$, $R_8$, $G_1$, $G_2$, $G_3$, $G_4$, and $G_5$ are as defined above, and in which X is SO or $SO_2$, and wherein Xa is a leaving group like, for example, chlorine, bromine or iodine (preferably bromine), or an aryl- or alkylsulfonate such as trifluoromethanesulfonate, with compounds of formula X, wherein Q is as defined above, and wherein $Y_{b1}$ can be a boron-derived functional group, such as for example $B(OH)_2$ or $B(OR_{b1})_2$ wherein $R_{b1}$ can be a $C_1$-$C_4$alkyl group or the two groups $OR_{b1}$ can form together with the boron atom a five membered ring, as for example a pinacol boronic ester. The reaction may be catalyzed by a palladium based catalyst, for example tetrakis(triphenylphosphine)-palladium(0), (1,1'bis(diphenylphosphino)ferrocene)dichloro-palladium-dichloromethane (1:1 complex) or chloro(2-dicyclohexylphosphino-2',4',6'-triisopropyl-1,1'-biphenyl)[2-(2'-amino-1,1'-biphenyl)] palladium(II) (XPhos palladacycle), in presence of a base, like sodium carbonate, tripotassium phosphate or cesium fluoride, in a solvent or a solvent mixture, like, for example dioxane, acetonitrile, N,N-dimethyl-formamide, a mixture of 1,2-dimethoxyethane and water or of dioxane/water, or of toluene/water, preferably under inert atmosphere. The reaction temperature can preferentially range from room temperature to the boiling point of the reaction mixture, or the reaction may be performed under microwave irradiation. Such Suzuki reactions are well known to those skilled in the art and have been reviewed, for example, in *J. Orgmet. Chem.* 576, 1999, 147-168.

Alternatively compounds of formula I-$Q_1$, wherein X is SO or $SO_2$, may be prepared by a Stille reaction between compounds of formula Xa, wherein Q is as defined above, and wherein $Y_{b2}$ is a trialkyl tin derivative, preferably tri-n-butyl tin or tri-methyl-tin, and compounds of formula IX, wherein A, $R_1$, $R_8$, $G_1$, $G_2$, $G_3$, $G_4$, and $G_5$ are as defined above, and in which X is SO or $SO_2$, and wherein Xa is a leaving group like, for example, chlorine, bromine or iodine (preferably bromine), or an aryl- or alkylsulfonate such as trifluoromethanesulfonate. Such Stille reactions are usually carried out in the presence of a palladium catalyst, for example tetrakis(triphenylphosphine)palladium(0), or bis (triphenylphosphine) palladium(II) dichloride, in an inert solvent such as N,N-dimethylformamide, acetonitrile, toluene or dioxane, optionally in the presence of an additive, such as cesium fluoride, or lithium chloride, and optionally in the presence of a further catalyst, for example copper(I) iodide. Such Stille couplings are also well known to those skilled in the art, and have been described in for example *J. Org. Chem.*, 2005, 70, 8601-8604, *J. Org. Chem.*, 2009, 74, 5599-5602, and *Angew. Chem. Int. Ed.*, 2004, 43, 1132-1136.

When Q is a five- to six-membered, aromatic, partially saturated or fully saturated ring system linked via a nitrogen atom to the ring which contains the group A, then compounds of formula I-$Q_1$, wherein X is SO or $SO_2$, may be prepared from compounds of formula IX, wherein A, $R_1$, $R_8$, $G_1$, $G_2$, $G_3$, $G_4$, and $G_5$ are as defined above, and in which X is SO or $SO_2$, and wherein Xa is a leaving group like, for example, chlorine, bromine or iodine (preferably bromine), or an aryl- or alkylsulfonate such as trifluoromethanesulfonate, by reaction with a heterocycle Q-H (which contains an appropriate NH functionality) Xaa, wherein Q is as defined above, in the presence of a base, such as potassium carbonate $K_2CO_3$ or cesium carbonate $Cs_2CO_3$, optionally in the presence of a copper catalyst, for example copper(I) iodide, with or without an additive such as L-proline, N,N'-dimethylcyclohexane-1,2-diamine or N,N'-dimethyl-ethylene-diamine, in an inert solvent such as N-methylpyrrolidone NMP or N,N-dimethylformamide DMF at temperatures between 30-150° C., optionally under microwave irradiation. Such a reaction (C—N Bond Formation) is illustrated below (scheme 3) for the heterocycle Q-H J-30b, wherein J30b and Rx are as defined above, Scheme 3:

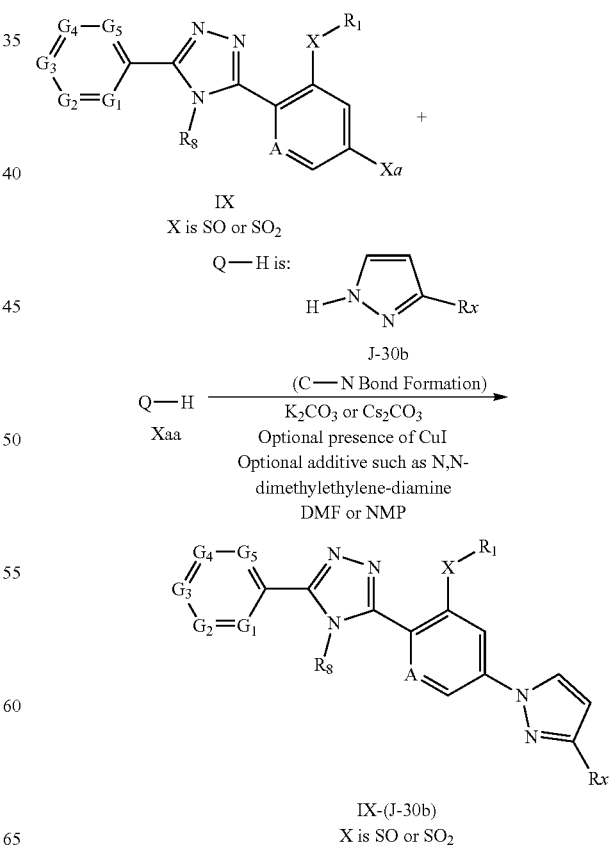

to give compounds of formula IX-(J-30b), a particular sub-group of compounds of formula IX, wherein A, $R_1$, $R_8$, $G_1$, $G_2$, $G_3$, $G_4$, and $G_5$ and Rx are as previously defined.

Oxidation of compounds of formula IX, wherein A, $R_1$, $R_8$, $G_1$, $G_2$, $G_3$, $G_4$, and $G_5$ are as defined above, and in which X is S (sulfide), and wherein Xa is a leaving group like, for example, chlorine, bromine or iodine (preferably bromine), or an aryl- or alkylsulfonate such as trifluoromethanesulfonate, with a suitable oxidizing agent, into compounds of formula IX, wherein X is SO or $SO_2$ may be achieved under conditions already described above.

A large number of compounds of the formula X, Xa and Xaa are commercially available or can be prepared by those skilled in the art.

Alternatively, compounds of formula I-$Q_1$, wherein X is SO or $SO_2$, may be prepared from compounds of formula IX, wherein X is S (sulfide) by involving the same chemistry as described above, but by changing the order of the steps (i.e. by running the sequence IX (X is S) to I-$Q_1$ (X is S) via Suzuki, Stille or C—N bond formation, followed by an oxidation step to form I-$Q_1$ (X is SO or $SO_2$).

In the particular situation within scheme 2 when Q is an optionally substituted triazole linked via a nitrogen atom to the ring which contains the group A, then compounds of formula I-$Q_1$, wherein X is SO or $SO_2$, may be prepared from compounds of formula IX, wherein A, $R_1$, $R_8$, $G_1$, $G_2$, $G_3$, $G_4$, and $G_5$ are as defined above, and in which X is S, SO or $SO_2$, and wherein Xa is a leaving group like, for example, chlorine, bromine or iodine (preferably bromine), or an aryl- or alkylsulfonate such as trifluoromethanesulfonate, by reaction with an optionally substituted triazole Q-H (which contains an appropriate NH functionality) Xaa, wherein Q is N-linked triazolyl, in solvents such as alcohols (eg. methanol, ethanol, isopropanol, or higher boiling linear or branched alcohols), pyridine or acetic acid, optionally in the presence of an additional base, such as potassium carbonate $K_2CO_3$ or cesium carbonate $Cs_2CO_3$, optionally in the presence of a copper catalyst, for example copper(I) iodide, at temperatures between 30-180° C., optionally under microwave irradiation.

Compounds of formula IX, wherein A, $R_1$, $R_8$, $G_1$, $G_2$, $G_3$, $G_4$, and $G_5$ are as defined above, and in which X is S (sulfide), and wherein Xa is a leaving group like, for example, chlorine, bromine or iodine (preferably bromine), or an aryl- or alkylsulfonate such as trifluoromethanesulfonate,

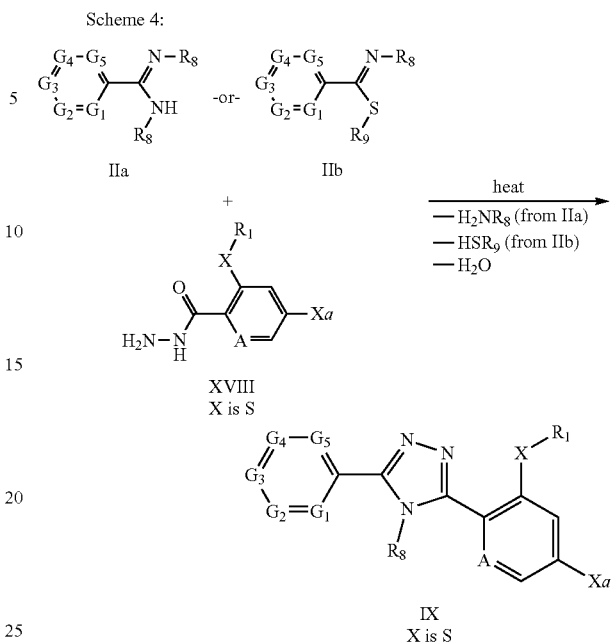

may be prepared (scheme 4) by reacting an amidine compound of formula IIa, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above;

or alternatively, by reacting an alkyl carboximidothioate compound of formula IIb, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above, and in which $R_9$ is $C_{1-6}$alkyl; with a hydrazide compound of formula XVIII, or a salt thereof, wherein A and $R_1$ are as defined above, and in which X is S (sulfide), and wherein Xa is a leaving group like, for example, chlorine, bromine or iodine (preferably bromine), or an aryl- or alkylsulfonate such as trifluoromethanesulfonate, optionally in presence of a base such as alkali metal carbonates, for example sodium carbonate or potassium carbonate, in a solvent such as methanol, ethanol, isopropanol, acetonitrile, pyridine, acetic acid, N,N-dimethylformamide or N,N-dimethylacetamide, at temperatures between 0 and 200° C., preferably between 50 and 180° C., optionally under microwave irradiation. The compounds of formula IIa or IIb may be reacted with any configuration (E or Z, or any mixture thereof) on the carbon-nitrogen double bond.

Compounds of formula XVIII, or a salt thereof, wherein A and $R_1$ are as defined above, and in which X is S (sulfide), and wherein Xa is a leaving group like, for example, chlorine, bromine or iodine (preferably bromine), or an aryl- or alkylsulfonate such as trifluoromethanesulfonate, Scheme 5:

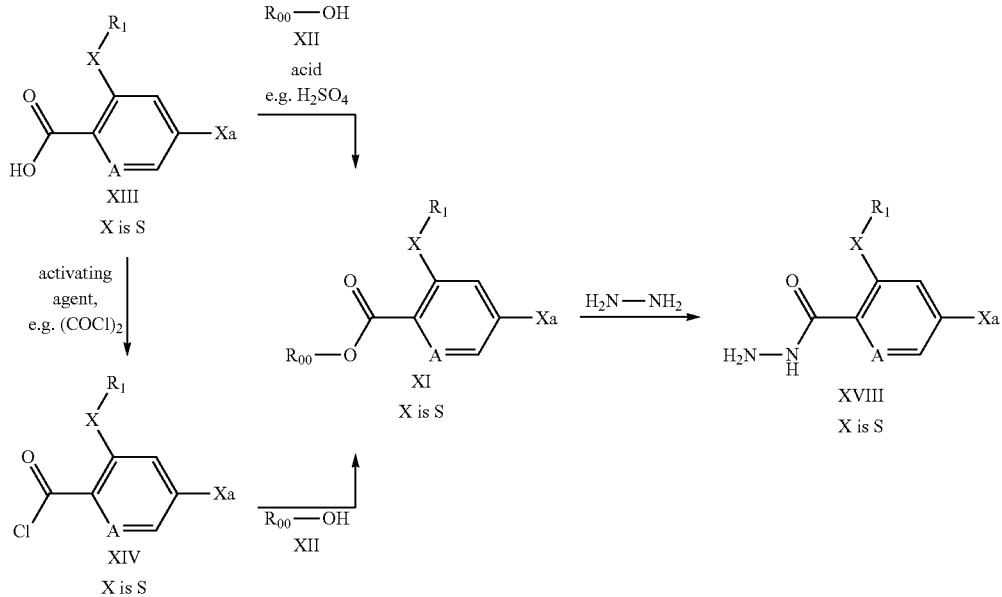

may be prepared (scheme 5) in analogy to processes described above (see for example preparation of compounds of the formula III, or scheme 1) from compounds of the formula XIII, via compounds of the formula XI, wherein A and $R_1$ are as defined above, and in which X is S (sulfide), and wherein Xa is a leaving group like, for example, chlorine, bromine or iodine (preferably bromine), or an aryl- or alkylsulfonate such as trifluoromethanesulfonate, and wherein $R_{00}$ is $C_1$-$C_4$alkyl, preferably methyl or ethyl.

Compounds of formula XIII, wherein A and $R_1$ are as defined above, and in which X is S (sulfide), and wherein Xa is a leaving group like, for example, chlorine, bromine or iodine (preferably bromine), or an aryl- or alkylsulfonate such as trifluoromethanesulfonate, Scheme 6:

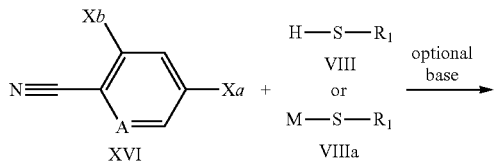

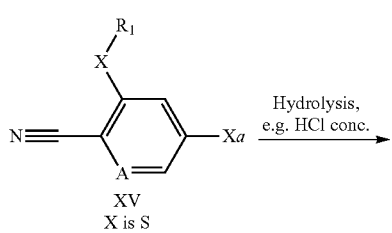

-continued

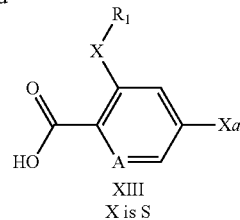

may be prepared (scheme 6) by hydrolysing compounds of formula XV, wherein X is S, and wherein A, $R_1$ and Xa are as defined above, for example through heating in concentrated acid, such as concentrated hydrochloric acid HCl conc., optionally in the presence of an inert solvent, such as ethers (for example tetrahydrofuran, ethylene glycol dimethyl ether, or 1,4-dioxane). Such hydrolysis conditions, and variants thereof, are known to a person skilled in the art.

Compounds of formula XV, wherein X is S, and wherein A, $R_1$ and Xa are as defined above, may be prepared by reacting compounds of formula XVI, wherein A and Xa are as defined above, and in which Xb is a leaving group such as, for example, a halogen (preferably fluorine, chlorine or bromine) or nitro, with a compound of formula VIII, or a salt thereof VIIIa, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, optionally in the presence of a catalytic amount of an additive, such as an ammonium salt (for example tetrabutylammonium bromide TBAB), in an inert solvent at temperatures preferably between 25-120° C. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile, polar aprotic solvents such as N,N-dimethylformamide, N,N-dimethylacetamide, N-methyl-2-pyrrolidone or dimethyl sulfoxide, or water. Examples of salts of the compound of formula VIII include compounds of the formula VIIIa

wherein $R_1$ is as defined above and wherein M is, for example, sodium or potassium.

Compounds of formula I-$Q_1$, wherein X is S, SO or $SO_2$,

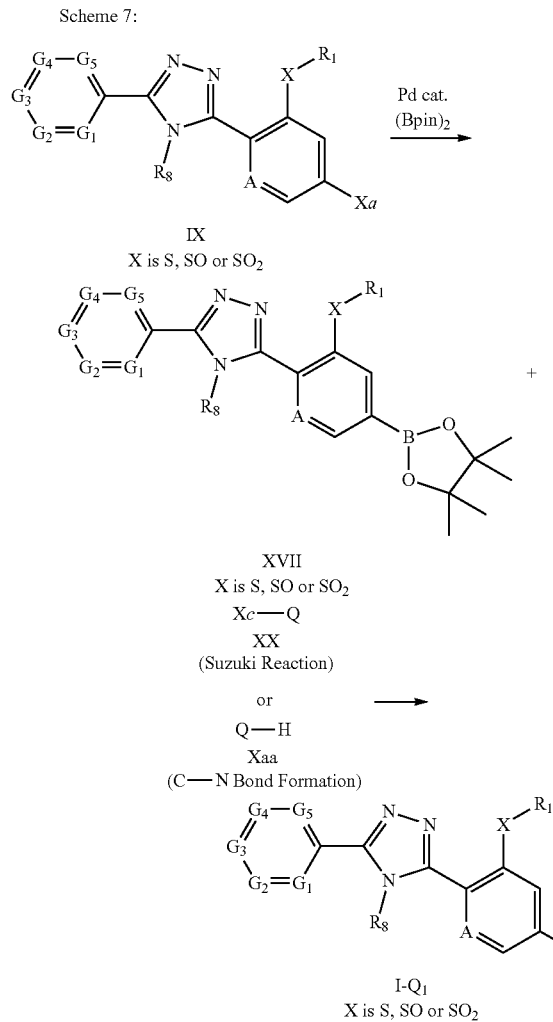

may alternatively be prepared by a Suzuki reaction (scheme 7), which involves for example, reacting compounds of formula XVII (or analogous boronic acids and esters of the formula XVII-Int), wherein A, $R_1$, $R_8$, $G_1$, $G_2$, $G_3$, $G_4$, and $G_5$ are as defined above, and in which X is S, SO or $SO_2$, with compounds of formula XX, wherein Q is as defined above, and wherein Xc is a leaving group like, for example, chlorine, bromine or iodine (preferably bromine), or an aryl- or alkylsulfonate such as trifluoromethanesulfonate. The reaction may be catalyzed by a palladium based catalyst, for example tetrakis(triphenylphosphine)-palladium(0), (1,1'bis(diphenylphosphino)ferrocene) dichloropalladium-dichloromethane (1:1 complex) or chloro(2-dicyclohexylphosphino-2',4',6'-triisopropyl-1,1'-biphenyl)[2-(2'-amino-1,1'-biphenyl)]palladium(II) (XPhos palladacycle), in presence of a base, like sodium carbonate, tripotassium phosphate or cesium fluoride, in a solvent or a solvent mixture, like, for example dioxane, acetonitrile, N,N-dimethylformamide, a mixture of 1,2-dimethoxy-ethane and water or of dioxane/water, or of toluene/water, preferably under inert atmosphere. The reaction temperature can preferentially range from room temperature to the boiling point of the reaction mixture, or the reaction may be performed under microwave irradiation. Such Suzuki reactions are well known to those skilled in the art and have been reviewed, for example, in *J. Orgmet. Chem.* 576, 1999, 147-168.

When Q is a five- to six-membered, aromatic, partially saturated or fully saturated ring system linked via a nitrogen atom to the ring which contains the group A, then compounds of formula I-$Q_1$, wherein X is S, SO or $SO_2$, may be prepared from compounds of formula XVII, wherein A, $R_1$, $R_8$, $G_1$, $G_2$, $G_3$, $G_4$, and $G_5$ are as defined above, and in which X is S, SO or $SO_2$, by reaction with a heterocycle Q-H (which contains an appropriate NH functionality) Xaa, wherein Q is as defined above. The reaction, also known as Chan-Lam coupling (P. Y. S. Lam, C. G. Clark, S. Saubern, J. Adams, M. P. Winters, D. M. T. Chan, A. Combs, Tetrahedron Lett. 1998, 39, 2941), is commonly performed with one to two equivalents of a base, like pyridine or triethylamine, in presence of one to two equivalents of a copper derivative, like for example copper (II) acetate and under an oxygen-containing atmosphere. The reaction can be run in an inert solvent, like dichloromethane, dioxane or dimethylformamide, usually at or around room temperature.

Compounds of formula XVII, wherein A, $R_1$, $R_8$, $G_1$, $G_2$, $G_3$, $G_4$, and $G_5$ are as defined above, and in which X is S, SO or $SO_2$, may be prepared by reacting compounds of formula IX, wherein A, $R_1$, $R_8$, $G_1$, $G_2$, $G_3$, $G_4$, and $G_5$ are as defined above, and in which X is S, SO or $SO_2$, and wherein Xa is a leaving group like, for example, chlorine, bromine or iodine (preferably bromine), or an aryl- or alkylsulfonate such as trifluoromethanesulfonate, with bispinacol diborane (Bpin)$_2$ under palladium catalysis. Such an introduction of a pinacolborate functional group can be performed in an aprotic solvent, such as dioxane, in presence of a base, preferably a weak base, such as potassium acetate KOAc. [1,1'-Bis(diphenylphosphino)ferrocene]dichloropalladium(II), also known as palladium dppf dichloride or Pd(dppf)Cl$_2$, is a common catalyst for this type of reaction. The temperature of the reaction is preferably performed between 0° C. and the boiling point of the reaction mixture, or the reaction may be performed under microwave irradiation.

The compounds of formula XVII-Int

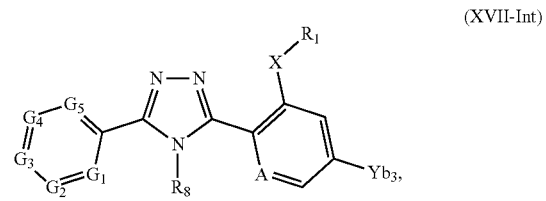

wherein $R_1$, $R_8$, $G_1$, $G_2$, $G_3$, $G_4$, $G_5$, X and A are as defined under formula I above, and Yb$_3$ is —B(OH)$_2$, —B(OR$_{b2}$)$_2$, in which R$_{b2}$ is a $C_1$-$C_6$alkyl or Yb$_3$ is

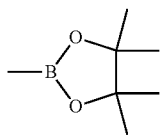

(a 4,4,5,5-tetramethyl-1,3,2-dioxaborolane group), are novel, especially developed for the preparation of the compounds of formula I according to the invention and therefore represent a further object of the invention. The preferences and preferred embodiments of the substituents of the compounds of formula I are also valid for the compounds of formula XVII-Int.

The subgroup of compounds of formula VIb(a), wherein $R_{00}$ are is as defined above and wherein $Q_a$ is defined as $Q_{1a}$, in which A, Q and $X_{10}$ are as defined above, may be defined as compounds of formula XXI. Compounds of formula XXI, Scheme 8:

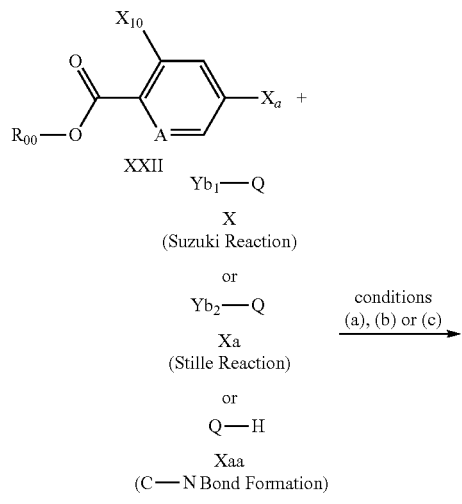

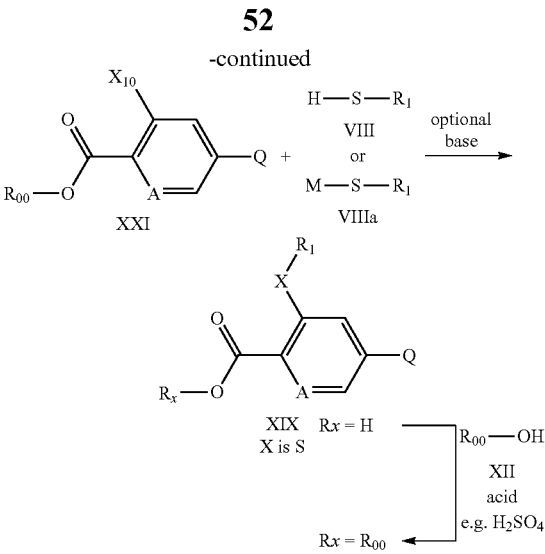

(a) Suzuki reaction: Pd cat. (e.g. Pd(PPh$_3$)$_4$ or Pd(dppf)Cl$_2$), base (e.g. Na$_2$CO$_3$), solvent (e.g. 1,2-dimethoxyethane/water), 25-180° C.
(b) Stille reaction: Pd cat. (e.g. Pd(PPh$_3$)$_4$ or Pd(PPh$_3$)Cl$_2$), solvent (e.g. toluene), 25-180° C.
(c) C—N bond formation: Base (e.g. K$_2$CO$_3$ or Cs$_2$CO$_3$), optional presence of CuI, optional additive (such as N,N'-dimethylethylenediamine), solvent (e.g. N,N-dimethylformamide DMF or N-methylpyrrolidone NMP), 25-180° C.

may serve to prepare useful building blocks of formula XIX (scheme 8), wherein A, Q, $R_1$ and $R_{00}$ are as defined above, and in which X is S (sulfide), by utilizing reagent VIII or VIIIa under reaction conditions that have been already described above.

Compounds of formula XXI, wherein A, Q, $X_{10}$ and $R_{00}$ are as defined above, may themselves be prepared from readily available compounds of formula XXII, wherein A, Xa, $X_{10}$ and $R_{00}$ are as defined above, involving reagents X, Xa or Xaa under reaction conditions that have been already described above.

Compounds of formula VII, wherein Qa is Qa$_1$, and in which A, Q and $X_{10}$ are as defined above, and wherein $R_8$, $G_1$, $G_2$, $G_3$, $G_4$, and $G_5$ are as defined above, Scheme 9:

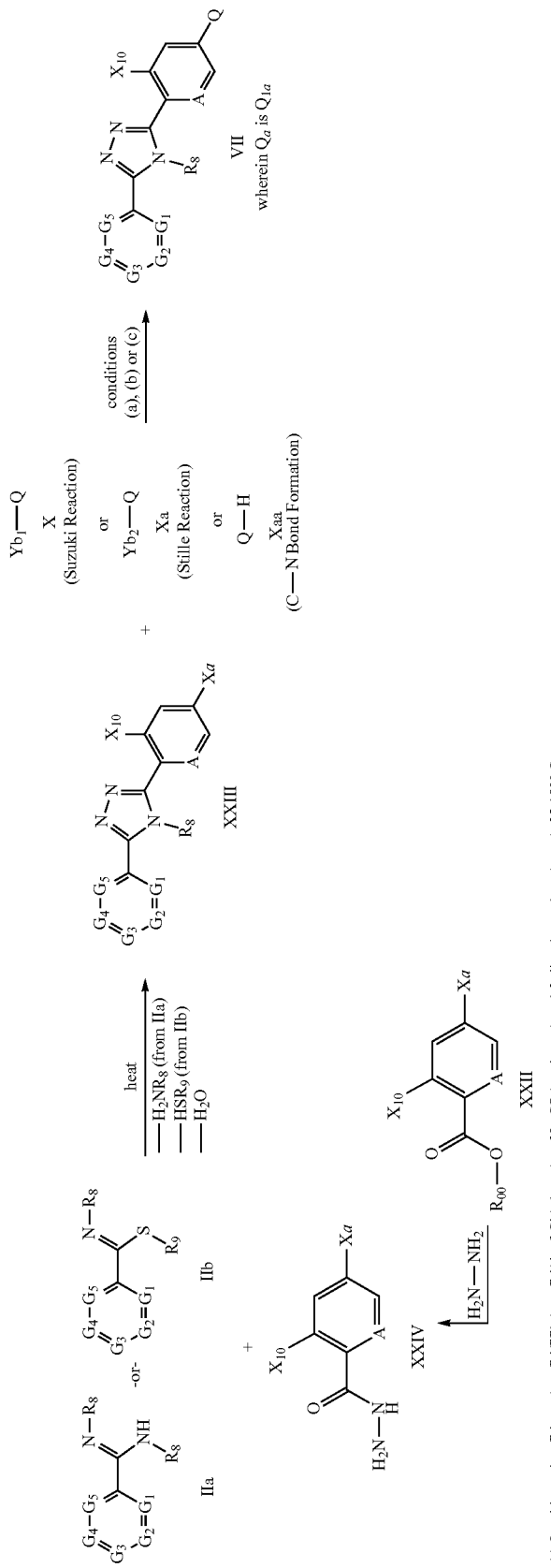

(a) Suzuki reaction: Pd cat. (e.g. Pd(PPh₃)₄ or Pd(dppf)Cl₂), base (e.g. Na₂CO₃), solvent (e.g. 1,2-dimethoxyethane/water), 25-180° C.
(b) Stille reaction: Pd cat. (e.g. Pd(PPh₃)₄ or Pd(PPh₃)₂Cl₂), solvent (e.g. toluene), 25-180° C.
(c) C—N bond formation: Base (e.g. K₂CO₃ or Cs₂CO₃), optional presence of CuI, optional additive (such as N,N′-dimethylethylenediamine), solvent (e.g. N,N-dimethylformamide DMF or N-methylpyrrolidone NMP), 25-180° C.

may alternatively be prepared (scheme 9) from compounds of formula XXIII, wherein Xa is as defined above, and in which A and $X_{10}$ are as defined above, and wherein $R_8$, $G_1$, $G_2$, $G_3$, $G_4$, and $G_5$ are as defined above, involving reagents X, Xa or Xaa under reaction conditions that have been already described above.

Compounds of formula XXIII, wherein A, Xa and $X_{10}$ are as defined above, and wherein $R_8$, $G_1$, $G_2$, $G_3$, $G_4$, and $G_5$ are as defined above, may be prepared by reacting an amidine compound of formula IIa, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above;

or alternatively, by reacting an alkyl carboximidothioate compound of formula IIb, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above, and in which $R_9$ is $C_{1-6}$alkyl;

with a hydrazide compound of formula XXIV, or a salt thereof, wherein A, Xa and $X_{10}$ are as defined above, optionally in presence of a base such as alkali metal carbonates, for example sodium carbonate or potassium carbonate, in a solvent such as methanol, ethanol, isopropanol, acetonitrile, pyridine, acetic acid, N,N-dimethylformamide or N,N-dimethylacetamide, at temperatures between 0 and 200° C., preferably between 50 and 180° C., optionally under microwave irradiation. The compounds of formula IIa or IIb may be reacted with any configuration (E or Z, or any mixture thereof) on the carbon-nitrogen double bond.

Compounds of formula XXIV, or a salt thereof, wherein A, Xa and $X_{10}$ are as defined above, may be prepared by reacting a readily available compounds of formula XXII, wherein A, Xa, $X_{10}$ and $R_{00}$ are as defined above, with hydrazine (or a salt thereof), possibly in form of a hydrate, preferably hydrazine monohydrate, under conditions that have been already described above.

The subgroup of compounds of formula I, wherein $R_8$, $G_1$, $G_2$, $G_3$, $G_4$, and $G_5$ are as defined above and wherein $R_7$ is defined as $Q_2$, in which A, Q, X and $R_1$ are as defined above, may be defined as compounds of formula I-$Q_2$ (scheme 10).

Scheme 10:

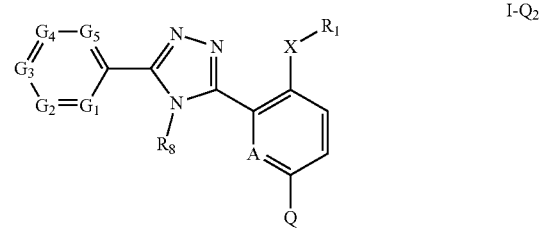

The chemistry described previously in schemes 2 to 9 to access compounds of formula I-$Q_1$, as well as relevant intermediates (see text, descriptions and preparation methods associated to schemes 2 to 9), may be applied analogously for the preparation of compounds of formula I-$Q_2$, possibly by changing the order of certain steps in a sequence and by slightly adapting reaction conditions in a manner known to a person skilled in the art. Such a transposition is illustrated in scheme 10a for the preparation of compounds of formula I-$Q_2$ from intermediate XXII-p, wherein all substituent definitions mentioned previously are also valid for the compounds shown.

Scheme 10a:

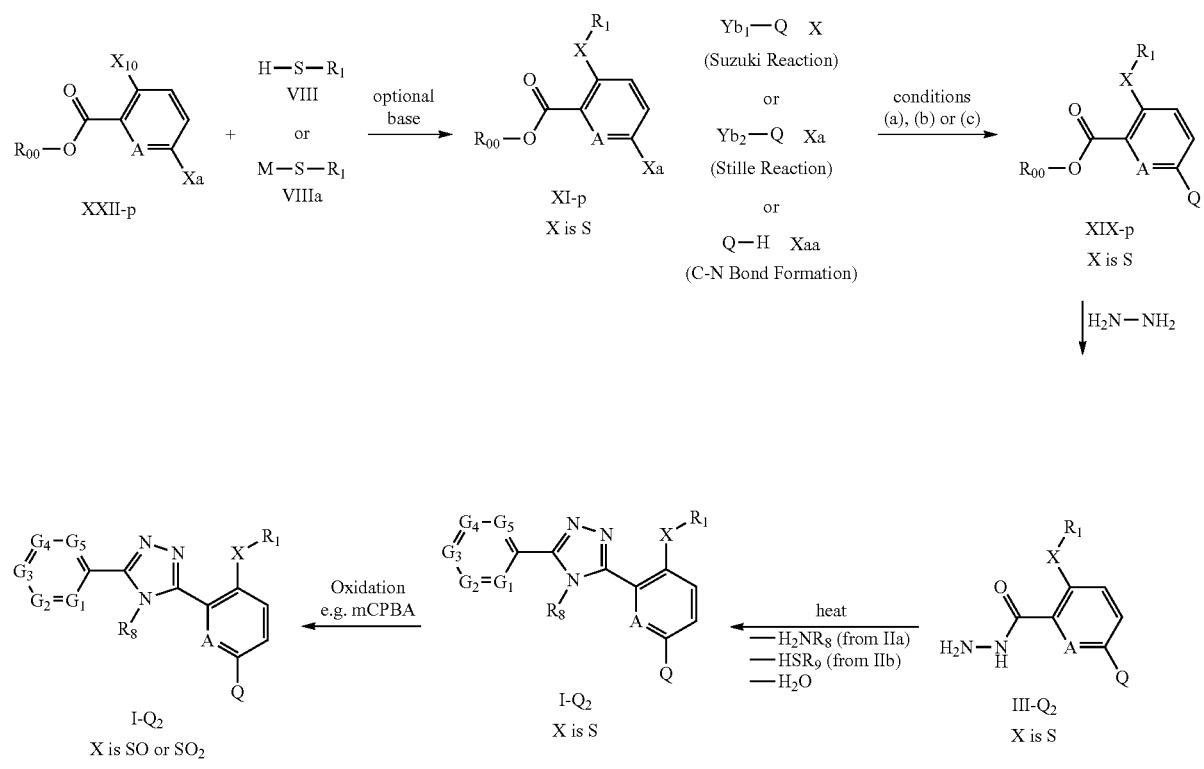

-continued

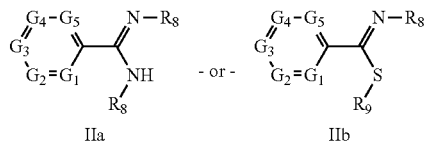
IIa -or- IIb (a) Suzuki reaction: Pd cat. (e.g. Pd(PPh₃)₄ or Pd(dppf)Cl₂), base (e.g. Na₂CO₃), solvent (e.g. 1,2-dimethoxyethane/water), 25-180° C.
(b) Stille reaction: Pd cat. (e.g. Pd(PPh₃)₄ or Pd(PPh₃)Cl₂), solvent (e.g. toluene), 25-180° C.
(c) C-N bond formation: Base (e.g. K₂CO₃ or Cs₂CO₃), optional presence of CuI, optional additive (such as N,N′-dimethylethylenediamine), solvent (e.g. N,N-dimethylformamide DMF or N-methylpyrrolidone NMP), 25-180° C.

Another such transposition is illustrated in scheme 10b, wherein all substituent definitions mentioned previously are also valid for the compounds shown.

Scheme 10b:

(a) Suzuki reaction: Pd cat. (e.g. Pd(PPh₃)₄ or Pd(dppf)Cl₂), base (e.g. Na₂CO₃), solvent (e.g. 1,2-dimethoxyethane/water), 25-180° C.
(b) Stille reaction: Pd cat. (e.g. Pd(PPh₃)₄ or Pd(PPh₃)Cl₂), solvent (e.g. toluene), 25-180° C.
(c) C—N bond formation: Base (e.g. K₂CO₃ or Cs₂CO₃), optional presence of CuI, optional additive (such as N,N′-dimethylethylenediamine), solvent (e.g. N,N-dimethylformamide DMF or N-methylpyrrolidone NMP), 25-180° C.

Compounds of formula I wherein Q is $C_3$-$C_6$cycloalkyl, mono- or polysubstituted by substituents selected from the group consisting of halogen, cyano, $C_1$-$C_4$haloalkyl, and phenyl, may be prepared by methods described above. For the special case of compounds of formula I wherein Q is $C_3$-$C_6$cycloalkyl substituted by cyano (e.g. compounds Iaa) and $C_1$-$C_4$haloalkyl (e.g. compounds Iad), the compounds can be prepared by the methods shown in scheme 11.

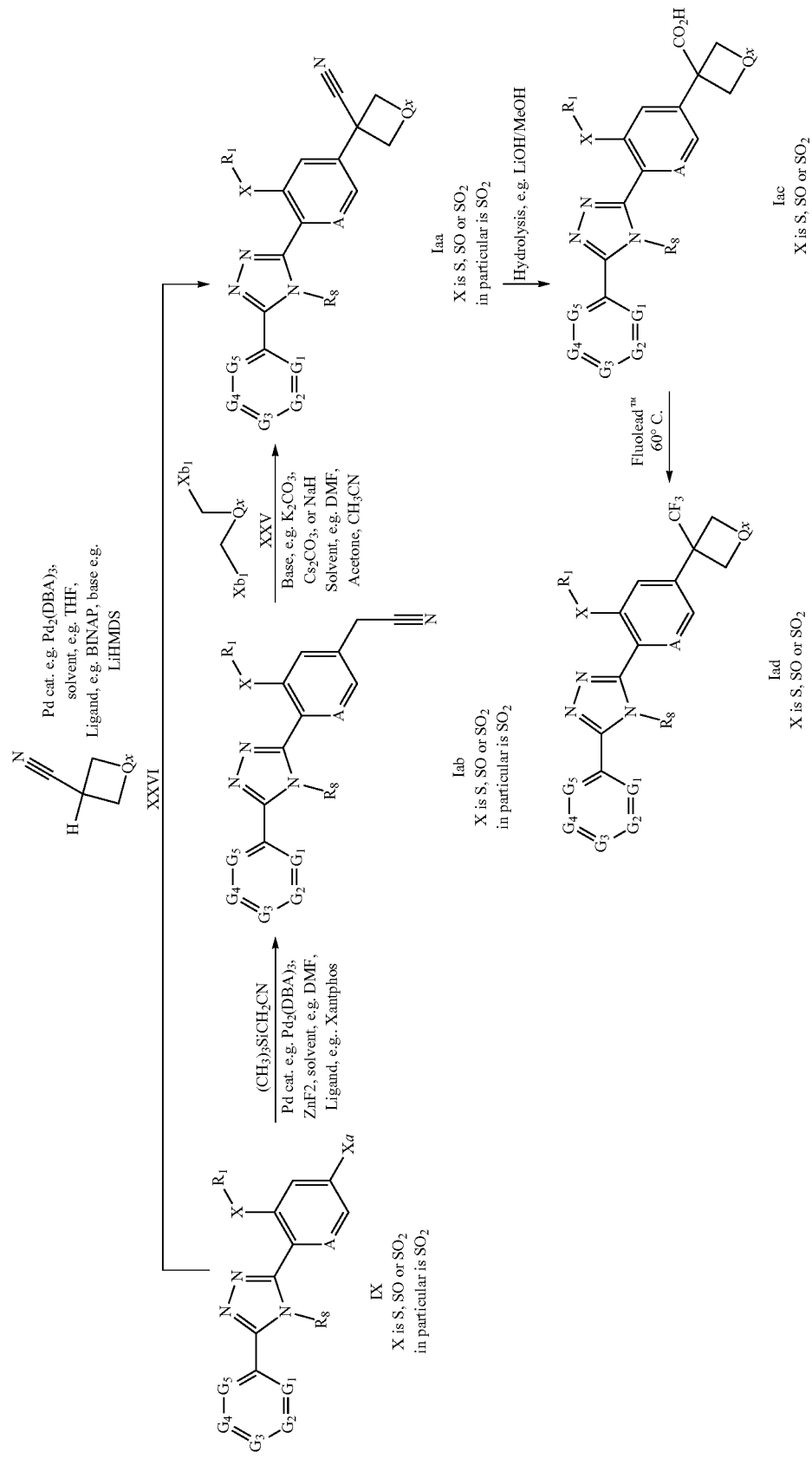

As shown in scheme 11, treatment of compounds of formula IX, wherein X is S, SO or $SO_2$ (in particular $SO_2$), and in which A, $R_1$, $R_8$, $G_1$, $G_2$, $G_3$, $G_4$, and $G_5$ are as defined above and wherein Xa is preferably halogen (even more preferably chlorine, bromine or iodine), with trimethylsilyl-acetonitrile TMSCN, in the presence of zinc(II)fluoride $ZnF_2$, and a palladium(0) catalyst such as tris(dibenzylideneacetone)dipalladium(0)-chloroform adduct $(Pd_2(dba)_3)$, with a ligand, for example Xantphos, in an inert solvent, such as N,N-dimethylformamide DMF at temperatures between 100-180° C., optionally under microwave heating, leads to compounds of formula Iab, wherein X is S, SO or $SO_2$ (in particular $SO_2$). Such chemistry has been described in the literature, e.g. in *Org. Lett.* 16(24), 6314-6317, 2014. Compounds of formula Iab can be treated with compounds of formula XXV, wherein Qx is a direct bond or is $(CH_2)_n$ and n is 1, 2 or 3, and in which $Xb_1$ is a leaving group such as a halogen (preferably chlorine, bromine or iodine), in the presence of a base such as sodium hydride, potassium carbonate $K_2CO_3$, or cesium carbonate $Cs_2CO_3$, in an inert solvent such as N,N-dimethyl-formamide DMF, acetone, or acetonitrile, at temperatures between 0-120° C., to give compounds of formula Iaa, wherein X is S, SO or $SO_2$ (in particular $SO_2$), and wherein A, $R_1$, $R_8$, $G_1$, $G_2$, $G_3$, $G_4$, and $G_5$ are as defined above and in which Qx is a direct bond or is $(CH_2)_n$ and n is 1, 2 or 3. Alternatively, compounds of formula Iaa can be prepared directly from compounds of formula IX by treatment with compounds of formula XXVI, wherein Qx is as described in XXV, in presence of a catalyst such as $Pd_2(dba)_3$, with a ligand, such as BINAP, a strong base such as lithium hexamethyldisilazane LiHMDS, in an inert solvent such as tetrahydrofuran THF, at temperatures between 30-80° C. Such chemistry has been described in, for example, *J. Am. Chem. Soc.* 127(45), 15824-15832, 2005.

Compounds of the formula Iaa may further be utilized for the preparation of compounds of formula Iad (scheme 11). Indeed, compounds of formula Iaa, wherein X is S, SO or $SO_2$, and wherein A, $R_1$, $R_8$, $G_1$, $G_2$, $G_3$, $G_4$, and $G_5$ are as defined above and in which Qx is a direct bond or is $(CH_2)_n$ and n is 1, 2 or 3, may be hydrolyzed, under conditions known to a person skilled in the art (aqueous basic or acidic conditions, see e.g. scheme 6), to compounds of formula Iac, wherein X is S, SO or $SO_2$, and wherein A, $R_1$, $R_8$, $G_1$, $G_2$, $G_3$, $G_4$, and $G_5$ are as defined above and in which Qx is a direct bond or is $(CH_2)_n$ and n is 1, 2 or 3. Treatment of compounds of formula Iac with reagents such as sulfur tetrafluoride $SF_4$ or Fluolead (4-tert-butyl-2,6-dimethyl phenylsulfur trifluoride), optionally in the presence of hydrogen fluoride HF, at temperatures between 20-100° C., leads to compounds of formula Iad, wherein X is S, SO or $SO_2$, and wherein A, $R_1$, $R_8$, $G_1$, $G_2$, $G_3$, $G_4$, and $G_5$ are as defined above and in which Qx is a direct bond or is $(CH_2)_n$ and n is 1, 2 or 3.

The compounds of formula (Iab)

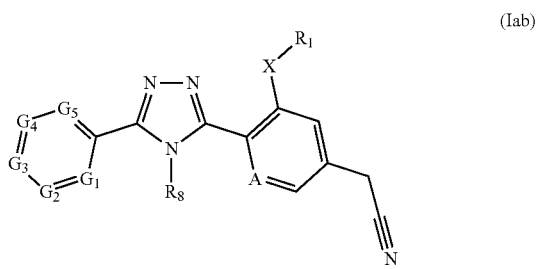

(Iab)

wherein $R_1$, $R_8$, $G_1$, $G_2$, $G_3$, $G_4$, $G_5$, X and A are as defined under formula I above, are novel, especially developed for the preparation of the compounds of formula I according to the invention and therefore represent a further object of the invention. The preferences and preferred embodiments of the substituents of the compounds of formula I are also valid for the compounds of formula (Iab).

Compounds of formula I wherein Q is $C_1$-$C_6$haloalkylsulfanyl (e.g. compounds Iae and/or Iaf), $C_1$-$C_6$haloalkylsulfinyl and $C_1$-$C_6$haloalkylsulfonyl can be prepared by the methods shown in schemes 12 and 13.

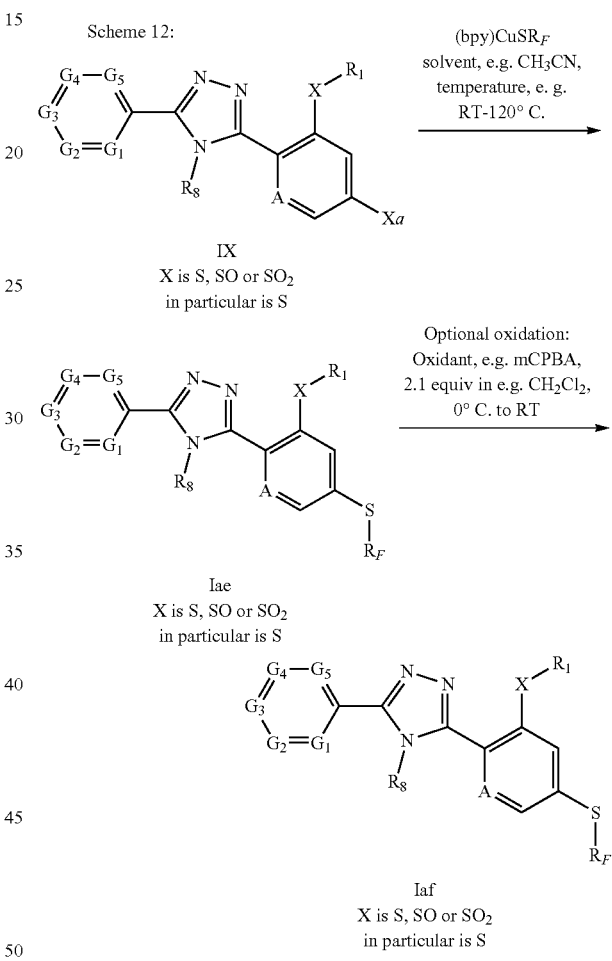

Scheme 12:

IX
X is S, SO or $SO_2$
in particular is S (bpy)CuSR$_F$
solvent, e.g. $CH_3CN$,
temperature, e. g.
RT-120° C.

Optional oxidation:
Oxidant, e.g. mCPBA,
2.1 equiv in e.g. $CH_2Cl_2$,
0° C. to RT Iae
X is S, SO or $SO_2$
in particular is S Iaf
X is S, SO or $SO_2$
in particular is S As shown in scheme 12, treatment of compounds of formula IX, wherein X is S, SO or $SO_2$ (in particular S), and in which A, $R_1$, $R_8$, $G_1$, $G_2$, $G_3$, $G_4$, and $G_5$ are as defined above and wherein Xa is preferably halogen (even more preferably chlorine, bromine or iodine), with a bipyridine copper reagent (bpy)CuSR$_F$, wherein R$_F$ is $C_1$-$C_6$haloalkyl, and in which bpy is bipyridyl, in an inert solvent such as acetonitrile, at temperatures between room temperature and 120° C., optionally under microwave heating, leads to compounds of formula Iae, wherein X is S, SO or $SO_2$ (in particular S), and in which A, $R_1$, $R_8$, $G_1$, $G_2$, $G_3$, $G_4$, and $G_5$ are as defined above and wherein R$_F$ is $C_1$-$C_6$haloalkyl. Such chemistry is known and has been described in the literature, for example, in Angew. Chem. Int. Ed. 2013, 52, 1548-1552. A preferred reagent for this transformation is (bpy)CuSCF₃ (CAS 1413732-47-4) for the particular preparation of compounds of formula Iae and Iaf, wherein $R_F$ is trifluoromethyl.

Compounds of formula Iae, wherein X is S or SO, can be further oxidized to, for example, compounds of formula Iaf, wherein X is SO or $SO_2$ (in particular $SO_2$), and in which A, $R_1$, $R_8$, $G_1$, $G_2$, $G_3$, $G_4$, and $G_5$ are as defined above and wherein $R_F$ is $C_1$-$C_6$haloalkyl, by methods known to those skilled in the art and described herein above.

Further adjustment of the oxidation state at sulfur centres can be accomplished as shown in scheme 13 by methods known to those skilled in the art. Thus, the compound of formula Iae, wherein X is S, can be oxidized to a compound of formula Iaf, wherein X is SO, by treating for example with sodium periodate or m-chloroperbenzoic acid, in an inert solvent such as dichloromethane and chloroform, alcohols such as methanol and ethanol, acetic acid, water, and mixtures thereof. The amount of the oxidant to be used in the reaction is generally 1 to 3 moles, preferably 1 to 1.1 moles, relative to 1 mole of the present compound Iae. The reaction temperature of the reaction is generally within a range of 0° C. to room temperature.

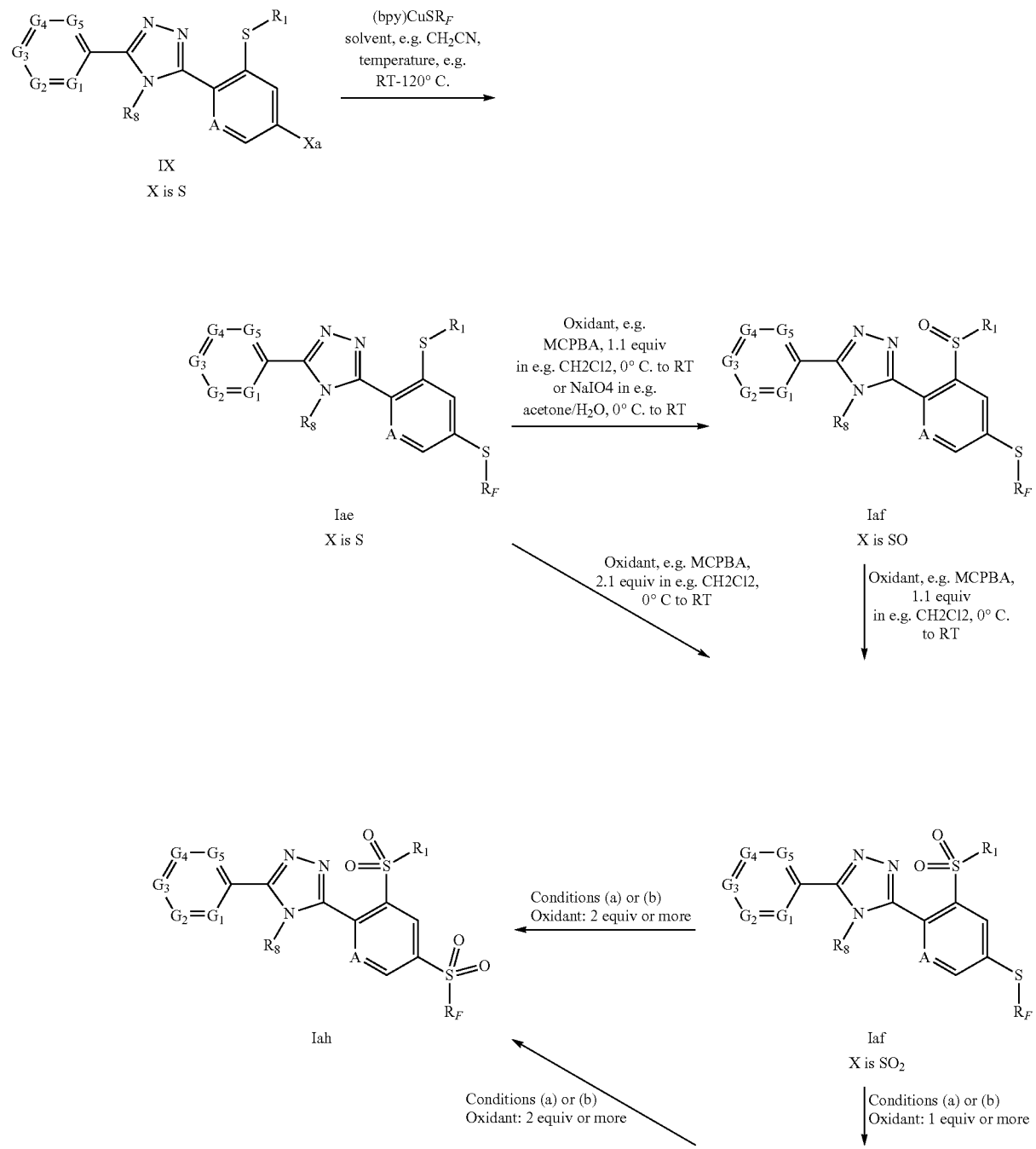

-continued

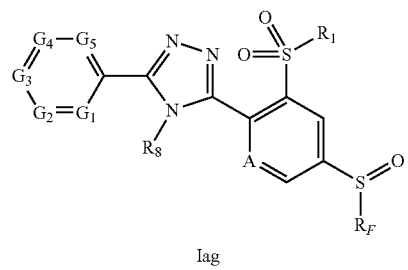

Iag

Conditions:
(a) catalyst, e.g Na$_2$WO$_4$·2H$_2$O,
    Oxidant e.g. H$_2$O$_2$
    solvent e.g. CH$_2$CN
    RT-100° C.

- or -

(b) Oxidant e.g. MCPBA,
    solvent e.g. CH$_2$Cl$_2$ or chloroform
    0° C. to 100° C.

The compound represented by the formula Iaf, wherein X is SO$_2$ can be produced by reacting the compound of formula Iae, wherein X is S, in the presence of an oxidant, such as m-chloroperbenzoic acid, in an inert solvent. Examples of the solvent to be used in the reaction include aliphatic halogenated hydrocarbons such as dichloromethane and chloroform, alcohols such as methanol and ethanol, acetic acid, water, and mixtures thereof. Examples of the oxidant to be used in the reaction include m-chloroperbenzoic acid and hydrogen peroxide solution. The amount of the oxidant to be used in the reaction is generally 1 to 4 moles, preferably 2.1 moles, relative to 1 mole of the present compound Iae. The reaction temperature of the reaction is generally within a range of 0° C. to room temperature. The reaction may be conducted in the presence of a catalyst. Examples of the catalyst to be used in the reaction include sodium tungstate. The SR$_F$ group, wherein R$_F$ is C$_1$-C$_6$haloalkyl, is more difficult to oxidize and so compounds of formula Iag and Iah generally require higher temperature with oxidants such as m-chloroperbenzoic acid or a hydrogen peroxide solution in the presence of a catalyst, for example sodium tungstate. Solvent and oxidant equivalent are similar to the descriptions above (conditions: see scheme 13). Those skilled in the art will appreciate that the degree and position of oxidation will depend on such factors as equivalents of oxidant and reaction temperature. Those skilled in the art will also appreciate that even if mixtures of products are formed, these can be separated by crystallization or chromatographic techniques, and the position and degree of oxidation can be determined by spectroscopic methods such as mass spectroscopy, NMR techniques and $^{13}$C-$^1$H coupling constants.

The chemistry described previously in schemes 11 to 13 to access compounds of formula I-Q$_1$, as well as relevant intermediates (see text, descriptions and preparation methods associated to schemes 11 to 13), may be applied analogously for the preparation of compounds of formula I-Q$_2$, possibly by changing the order of certain steps in a sequence and by slightly adapting reaction conditions in a manner known to a person skilled in the art.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo [5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 12 below can be prepared according to the methods described above. The examples which follow are intended to illustrate the invention and show preferred compounds of formula I.

Table 1: This table discloses the 36 compounds 1.001 to 1.036 of the formula I-1a:

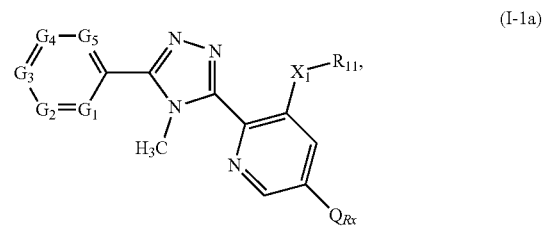

(I-1a)

wherein $X_1$ is S, and $Q_{Rx}$, $R_{11}$, $G_1$, $G_2$, $G_3$, $G_4$ and $G_5$ are as defined below:

TABLE 1

| Comp. No | $Q_{Rx}$ | $R_{11}$ | $G_1$ | $G_2$ | $G_3$ | $G_4$ | $G_5$ |
|---|---|---|---|---|---|---|---|
| 1.001 | phenyl | —$CH_2CH_3$ | N | CH | CH | $C(CF_3)$ | CH |
| 1.002 | 4-Cl-phenyl | —$CH_2CH_3$ | N | CH | CH | $C(CF_3)$ | CH |
| 1.003 | 4-$CF_3$-phenyl | —$CH_2CH_3$ | N | CH | CH | $C(CF_3)$ | CH |
| 1.004 | 3-Cl-pyridin-2-yl | —$CH_2CH_3$ | N | CH | CH | $C(CF_3)$ | CH |
| 1.005 | 5-Cl-pyridin-2-yl | —$CH_2CH_3$ | N | CH | CH | $C(CF_3)$ | CH |

TABLE 1-continued

| Comp. No | Q_Rx | R_11 | G_1 | G_2 | G_3 | G_4 | G_5 |
|---|---|---|---|---|---|---|---|
| 1.006 | 4-chloro-2-methylpyridine | —CH$_2$CH$_3$ | N | CH | CH | C(CF$_3$) | CH |
| 1.007 | 6-methyl-2-cyanopyridine | —CH$_2$CH$_3$ | N | CH | CH | C(CF$_3$) | CH |
| 1.008 | 6-methyl-3-cyanopyridine | —CH$_2$CH$_3$ | N | CH | CH | C(CF$_3$) | CH |
| 1.009 | 6-methyl-4-cyanopyridine | —CH$_2$CH$_3$ | N | CH | CH | C(CF$_3$) | CH |
| 1.010 | 2-methylpyrimidine | —CH$_2$CH$_3$ | N | CH | CH | C(CF$_3$) | CH |
| 1.011 | 2-methyl-5-chloropyrimidine | —CH$_2$CH$_3$ | N | CH | CH | C(CF$_3$) | CH |
| 1.012 | 2-methyl-5-cyanopyrimidine | —CH$_2$CH$_3$ | N | CH | CH | C(CF$_3$) | CH |
| 1.013 | 2-methyl-4-cyanopyrimidine | —CH$_2$CH$_3$ | N | CH | CH | C(CF$_3$) | CH |
| 1.014 | 1-methylpyrazole | —CH$_2$CH$_3$ | N | CH | CH | C(CF$_3$) | CH |
| 1.015 | 1-methyl-4-chloropyrazole | —CH$_2$CH$_3$ | N | CH | CH | C(CF$_3$) | CH |
| 1.016 | 1-methyl-4-cyanopyrazole | —CH$_2$CH$_3$ | N | CH | CH | C(CF$_3$) | CH |
| 1.017 | 1-methyl-4-trifluoromethylpyrazole | —CH$_2$CH$_3$ | N | CH | CH | C(CF$_3$) | CH |
| 1.018 | 1-methyl-5-chloropyrazole | —CH$_2$CH$_3$ | N | CH | CH | C(CF$_3$) | CH |
| 1.019 | 1-methyl-3-cyanopyrazole | —CH$_2$CH$_3$ | N | CH | CH | C(CF$_3$) | CH |
| 1.020 | 1-methyl-3-trifluoromethylpyrazole | —CH$_2$CH$_3$ | N | CH | CH | C(CF$_3$) | CH |
| 1.021 | 1-methyl-3-chloro-1,2,4-triazole | —CH$_2$CH$_3$ | N | CH | CH | C(CF$_3$) | CH |
| 1.022 | cyclopropyl | —CH$_2$CH$_3$ | N | CH | CH | C(CF$_3$) | CH |
| 1.023 | 1-cyanocyclopropyl | —CH$_2$CH$_3$ | N | CH | CH | C(CF$_3$) | CH |
| 1.024 | isopropenyl | —CH$_2$CH$_3$ | N | CH | CH | C(CF$_3$) | CH |
| 1.025 | 1-ethoxyvinyl | —CH$_2$CH$_3$ | N | CH | CH | C(CF$_3$) | CH |
| 1.026 | 1-methyl-4-cyanoimidazole | —CH$_2$CH$_3$ | N | CH | CH | C(CF$_3$) | CH |
| 1.027 | 3-fluoro-5-methylphenyl | —CH$_2$CH$_3$ | N | CH | CH | C(CF$_3$) | CH |
| 1.028 | 1-methyl-1,2,4-triazole | —CH$_2$CH$_3$ | N | CH | CH | C(CF$_3$) | CH |
| 1.029 | 1-methyl-3-cyano-1,2,4-triazole | —CH$_2$CH$_3$ | N | CH | CH | C(CF$_3$) | CH |
| 1.030 | cyclopropyl | —CH$_2$CH$_3$ | N | CH | N | C(CF$_3$) | CH |
| 1.031 | 1-cyanocyclopropyl | —CH$_2$CH$_3$ | N | CH | N | C(CF$_3$) | CH |
| 1.032 | 3-fluoro-5-methylphenyl | —CH$_2$CH$_3$ | N | CH | N | C(CF$_3$) | CH |
| 1.033 | 2-methylpyrimidine | —CH$_2$CH$_3$ | N | CH | N | C(CF$_3$) | CH |
| 1.034 | 1-methyl-1,2,4-triazole | —CH$_2$CH$_3$ | N | CH | N | C(CF$_3$) | CH |

TABLE 1-continued

| Comp. No | Q_{Rx} | R_{11} | G_1 | G_2 | G_3 | G_4 | G_5 |
|---|---|---|---|---|---|---|---|
| 1.035 | ![triazole-Cl] | —CH$_2$CH$_3$ | N | CH | N | C(CF$_3$) | CH |
| 1.036 | ![triazole-CN] | —CH$_2$CH$_3$ | N | CH | N | C(CF$_3$) | CH | and the N-oxides of the compounds of Table 1.

Table 2: This table discloses the 36 compounds 2.001 to 2.036 of the formula I-1a, wherein $X_1$ is SO, and $Q_{Rx}$, $R_{11}$, $G_1$, $G_2$, $G_3$, $G_4$ and $G_5$ are as defined in Table 1.

Table 3: This table discloses the 36 compounds 3.001 to 3.036 of the formula I-1a, wherein $X_1$ is SO$_2$, and $Q_{Rx}$, $R_{11}$, $G_1$, $G_2$, $G_3$, $G_4$ and $G_5$ are as defined in Table 1.

Table 4: This table discloses the 2 compounds 4.001 to 4.002 of the formula I-2a:

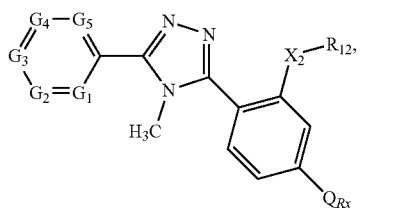

(I-2a)

wherein $X_2$ is S, and $Q_{Rx}$, $R_{12}$, $G_1$, $G_2$, $G_3$, $G_4$ and $G_5$ are as defined below:

TABLE 4

| Comp. No | Q_{Rx} | R_{12} | G_1 | G_2 | G_3 | G_4 | G_5 |
|---|---|---|---|---|---|---|---|
| 4.001 | ![phenyl-Cl] | —CH$_2$CH$_3$ | N | CH | CH | C(CF$_3$) | CH |
| 4.002 | ![pyrimidinyl] | —CH$_2$CH$_3$ | N | CH | CH | C(CF$_3$) | CH | and the N-oxides of the compounds of Table 4.

Table 5: This table discloses the 2 compounds 5.001 to 5.002 of the formula I-2a, wherein $X_1$ is SO, and $Q_{Rx}$, $R_{12}$, $G_1$, $G_2$, $G_3$, $G_4$ and $G_5$ are as defined in Table 4.

Table 6: This table discloses the 2 compounds 6.001 to 6.002 of the formula I-2a, wherein $X_1$ is SO$_2$, and $Q_{Rx}$, $R_{12}$, $G_1$, $G_2$, $G_3$, $G_4$ and $G_5$ are as defined in Table 4.

Table 7: This table discloses the 15 compounds 7.001 to 7.015 of the formula I-3a:

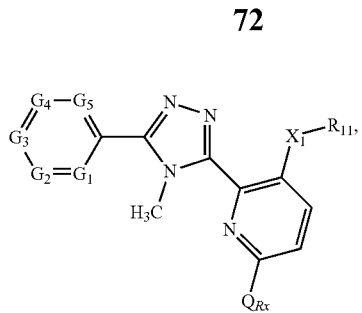

(I-3a)

wherein $X_1$ is S, and $Q_{Rx}$, $R_{11}$, $G_1$, $G_2$, $G_3$, $G_4$ and $G_5$ are as defined below:

TABLE 7

| Comp. No | Q_{Rx} | R_{11} | G_1 | G_2 | G_3 | G_4 | G_5 |
|---|---|---|---|---|---|---|---|
| 7.001 | phenyl | —CH$_2$CH$_3$ | N | CH | CH | C(CF$_3$) | CH |
| 7.002 | 4-CF$_3$-phenyl | —CH$_2$CH$_3$ | N | CH | CH | C(CF$_3$) | CH |
| 7.003 | 3-F-phenyl | —CH$_2$CH$_3$ | N | CH | CH | C(CF$_3$) | CH |
| 7.004 | triazolyl | —CH$_2$CH$_3$ | N | CH | CH | C(CF$_3$) | CH |
| 7.005 | triazolyl-Cl | —CH$_2$CH$_3$ | N | CH | CH | C(CF$_3$) | CH |
| 7.006 | triazolyl-CN | —CH$_2$CH$_3$ | N | CH | CH | C(CF$_3$) | CH |
| 7.007 | cyclopropyl | —CH$_2$CH$_3$ | N | CH | CH | C(CF$_3$) | CH |
| 7.008 | pyrimidinyl | —CH$_2$CH$_3$ | N | CH | CH | C(CF$_3$) | CH |
| 7.009 | 3-F-phenyl | —CH$_2$CH$_3$ | N | CH | N | C(CF$_3$) | CH |
| 7.010 | triazolyl | —CH$_2$CH$_3$ | N | CH | N | C(CF$_3$) | CH |
| 7.011 | triazolyl-Cl | —CH$_2$CH$_3$ | N | CH | N | C(CF$_3$) | CH |

TABLE 7-continued

| Comp. No | $Q_{Rx}$ | $R_{11}$ | $G_1$ | $G_2$ | $G_3$ | $G_4$ | $G_5$ |
|---|---|---|---|---|---|---|---|
| 7.012 | 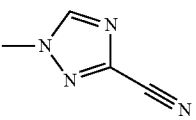 | —CH$_2$CH$_3$ | N | CH | N | C(CF$_3$) | CH |
| 7.013 | 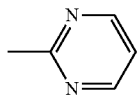 | —CH$_2$CH$_3$ | N | CH | N | C(CF$_3$) | CH |
| 7.014 | 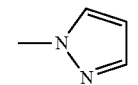 | —CH$_2$CH$_3$ | N | CH | N | C(CF$_3$) | CH |
| 7.015 | 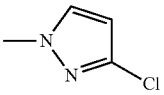 | —CH$_2$CH$_3$ | N | CH | N | C(CF$_3$) | CH | and the N-oxides of the compounds of Table 7.

Table 8: This table discloses the 15 compounds 8.001 to 8.015 of the formula I-3a, wherein $X_1$ is SO, and $Q_{Rx}$, $R_{11}$, $G_1$, $G_2$, $G_3$, $G_4$ and $G_5$ are as defined in Table 7.

Table 9: This table discloses the 15 compounds 9.001 to 9.015 of the formula I-3a, wherein $X_1$ is SO$_2$, and $Q_{Rx}$, $R_{11}$, $G_1$, $G_2$, $G_3$, $G_4$ and $G_5$ are as defined in Table 7.

Table 10: This table discloses the 2 compounds 10.001 to 10.002 of the formula I-4a:

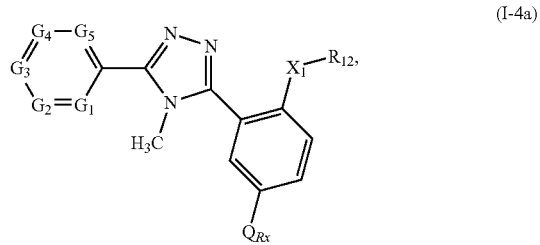

(I-4a)

wherein $X_2$ is S, and $Q_{Rx}$, $R_{12}$, $G_1$, $G_2$, $G_3$, $G_4$ and $G_5$ are as defined below:

TABLE 10

| Comp. No | $Q_{Rx}$ | $R_{12}$ | $G_1$ | $G_2$ | $G_3$ | $G_4$ | $G_5$ |
|---|---|---|---|---|---|---|---|
| 10.001 | 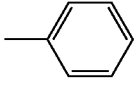 | —CH$_2$CH$_3$ | N | CH | CH | C(CF$_3$) | CH |
| 10.002 | 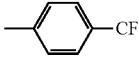 | —CH$_2$CH$_3$ | N | CH | CH | C(CF$_3$) | CH | and the N-oxides of the compounds of Table 10.

Table 11: This table discloses the 2 compounds 11.001 to 11.002 of the formula I-4a, wherein $X_2$ is SO, and $Q_{Rx}$, $R_{12}$, $G_1$, $G_2$, $G_3$, $G_4$ and $G_5$ are as defined in Table 10.

Table 12: This table discloses the 2 compounds 12.001 to 12.002 of the formula I-4a, wherein $X_2$ is SO$_2$, and $Q_{Rx}$, $R_{12}$, $G_1$, $G_2$, $G_3$, $G_4$ and $G_5$ are as defined in Table 10.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:
from the order Acarina, for example,
Acalitus spp, Aculus spp, Acaricalus spp, Aceria spp, Acarus siro, Amblyomma spp., Argas spp., Boophilus spp., Brevipalpus spp., Bryobia spp, Calipitrimerus spp., Chorioptes spp., Dermanyssus gallinae, Dermatophagoides spp, Eotetranychus spp, Eriophyes spp., Hemitarsonemus spp, Hyalomma spp., Ixodes spp., Olygonychus spp, Ornithodoros spp., Polyphagotarsone latus, Panonychus spp., Phyllocoptruta oleivora, Phytonemus spp, Polyphagotarsonemus spp, Psoroptes spp., Rhipicephalus spp., Rhizoglyphus spp., Sarcoptes spp., Steneotarsonemus spp, Tarsonemus spp. and Tetranychus spp.;

from the order Anoplura, for example,
Haematopinus spp., Linognathus spp., Pediculus spp., Pemphigus spp. and Phylloxera spp.;

from the order Coleoptera, for example,
Agriotes spp., Amphimallon majale, Anomala orientalis, Anthonomus spp., Aphodius spp, Astylus atromaculatus, Ataenius spp, Atomaria linearis, Chaetocnema tibialis, Cerotoma spp, Conoderus spp, Cosmopolites spp., Cotinis nitida, Curculio spp., Cyclocephala spp, Dermestes spp., Diabrotica spp., Diloboderus abderus, Epilachna spp., Eremnus spp., Heteronychus arator, Hypothenemus hampei, Lagria vilosa, Leptinotarsa decemLineata, Lissorhoptrus spp., Liogenys spp, Maecolaspis spp, Maladera castanea, Megascelis spp, Melighetes aeneus, Melolontha spp., Myochrous armatus, Orycaephilus spp., Otiorhynchus spp., Phyllophaga spp., Phlyctinus spp., Popillia spp., Psylliodes spp., Rhyssomatus aubtilis, Rhizopertha spp., Scarabeidae, Sitophilus spp., Sitotroga spp., Somaticus spp, Sphenophorus spp, Sternechus subsignatus, Tenebrio spp., Tribolium spp. and Trogoderma spp.;

from the order Diptera, for example,
Aedes spp., Anopheles spp, Antherigona soccata, Bactrocea oleae, Bibio hortulanus, Bradysia spp, Calliphora erythrocephala, Ceratitis spp., Chrysomyia spp., Culex spp., Cuterebra spp., Dacus spp., Delia spp, Drosophila melanogaster, Fannia spp., Gastrophilus spp., Geomyza tripunctata, Glossina spp., Hypoderma spp., Hyppobosca spp., Liriomyza spp., Lucilia spp., Melanagromyza spp., Musca spp., Oestrus spp., Orseolia spp., Oscinella frit, Pegomyia hyoscyami, Phorbia spp., Rhagoletis spp, Rivelia quadrifasciata, Scatella spp., Sciara spp., Stomoxys spp., Tabanus spp., Tannia spp. and Tipula spp.;

from the order Hemiptera, for example,
Acanthocoris scabrator, Acrosternum spp, Adelphocoris lineolatus, Amblypelta nitida, Bathycoelia thalassina, Blissus spp, Cimex spp., Clavigralla tomentosicollis, Creontiades spp, Distantiella theobroma, Dichelops furcatus, Dysdercus spp., Edessa spp., Euchistus spp., Eurydema

*pulchrum, Eurygaster* spp., *Halyomorpha halys, Horcias nobilellus, Leptocorisa* spp., *Lygus* spp, *Margarodes* spp, *Murgantia histrionic, Neomegalotomus* spp, *Nesidiocoris tenuis, Nezara* spp., *Nysius simulans, Oebalus insularis, Piesma* spp., *Piezodorus* spp, *Rhodnius* spp., *Sahlbergella singularis, Scaptocoris castanea, Scotinophara* spp., *Thyanta* spp, *Triatoma* spp., *Vatiga illudens;*

*Acyrthosium pisum, Adalges* spp, *Agalliana ensigera, Agonoscena targionii, Aleurodicus* spp, *Aleurocanthus* spp, *Aleurolobus barodensis, Aleurothrixus floccosus, Aleyrodes brassicae, Amarasca biguttula, Amritodus atkinsoni, Aonidiella* spp., *Aphididae, Aphis* spp., *Aspidiotus* spp., *Aulacorthum solani, Bactericera cockerelli, Bemisia* spp, *Brachycaudus* spp, *Brevicoryne brassicae, Cacopsylla* spp, *Cavariella aegopodii Scop., Ceroplaster* spp., *Chrysomphalus aonidium, Chrysomphalus dictyospermi, Cicadella* spp, *Cofana spectra, Cryptomyzus* spp, *Cicadulina* spp, *Coccus hesperidum, Dalbulus maidis, Dialeurodes* spp, *Diaphorina citri, Diuraphis noxia, Dysaphis* spp, *Empoasca* spp., *Eriosoma larigerum, Erythroneura* spp., *Gascardia* spp., *Glycaspis brimblecombei, Hyadaphis pseudobrassicae, Hyalopterus* spp, *Hyperomyzus pallidus, Idioscopus clypealis, Jacobiasca lybica, Laodelphax* spp., *Lecanium corni, Lepidosaphes* spp., *Lopaphis erysimi, Lyogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri Mats, Odonaspis ruthae, Oregma lanigera Zehnter, Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;* from the order Hymenoptera, for example,

*Acromyrmex, Arge* spp, *Atta* spp., *Cephus* spp., *Diprion* spp., *Diprionidae, Gilpinia polytoma, Hoplocampa* spp., *Lasius* spp., *Monomorium pharaonis, Neodiprion* spp., *Pogonomyrmex* spp, *Slenopsis invicta, Solenopsis* spp. and *Vespa* spp.;

from the order Isoptera, for example,

*Coptotermes* spp, *Corniternes cumulans, Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina.*

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis, Anthemis* spp., *Antirrhinum* spp., *Aster* spp., *Begonia* spp. (e.g. *B. elatior, B. semperflorens, B. tubéreux*), *Bougainvillea* spp., *Brachycome* spp., *Brassica* spp. (ornamental), *Calceolaria* spp., *Capsicum annuum, Catharanthus roseus, Canna* spp., *Centaurea* spp., *Chrysanthemum* spp., *Cineraria* spp. (*C. maritime*), *Coreopsis* spp., *Crassula coccinea, Cuphea ignea, Dahlia* spp., *Delphinium* spp., *Dicentra spectabilis, Doro-*

*theantus* spp., *Eustoma grandiflorum*, *Forsythia* spp., *Fuchsia* spp., *Geranium gnaphalium*, *Gerbera* spp., *Gomphrena globosa*, *Heliotropium* spp., *Helianthus* spp., *Hibiscus* spp., *Hortensia* spp., *Hydrangea* spp., *Hypoestes phyllostachya*, *Impatiens* spp. (*I. Walleriana*), *Iresines* spp., *Kalanchoe* spp., *Lantana camara*, *Lavatera trimestris*, *Leonotis leonurus*, *Lilium* spp., *Mesembryanthemum* spp., *Mimulus* spp., *Monarda* spp., *Nemesia* spp., *Tagetes* spp., *Dianthus* spp. (*carnation*), *Canna* spp., *Oxalis* spp., *Bellis* spp., *Pelargonium* spp. (*P. peltatum, P. Zonale*), *Viola* spp. (*pansy*), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola*, *Schizanthus wisetonensis*, *Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus officinalis, Beta vulgarus, Brassica* spp. (*B. Oleracea, B. Pekinensis, B. rapa*), *Capsicum annuum, Cicer arietinum, Cichorium endivia, Cichorum* spp. (*C. intybus, C. endivia*), *Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica, Solanum melongena, Spinacea oleracea, Valerianella* spp. (*V. locusta, V. eriocarpa*) and *Vicia faba*.

Preferred ornamental species include African violet, *Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia*, rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); *Cepaea* (*C. hortensis, C. Nemoralis*); ochlodina; *Deroceras* (*D. agrestis, D. empiricorum, D. laeve, D. reticulatum*); *Discus* (*D. rotundatus*); *Euomphalia*; *Galba* (*G. trunculata*); *Helicelia* (*H. itala, H. obvia*); Helicidae *Helicigona arbustorum*); *Helicodiscus*; *Helix* (*H. aperta*); *Limax* (*L. cinereoniger, L. flavus, L. marginatus, L. maximus, L. tenellus*); *Lymnaea*; *Milax* (*M. gagates, M. marginatus, M. sowerbyi*); Opeas; *Pomacea* (*P. canaticulata*); Vallonia and Zanitoides.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810). Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricin N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defense (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, |

TABLE B-continued

Examples of native woodborers of economic importance.

| Family | Species | Host or Crop Infested |
|---|---|---|
| | | Lilac, Mountain-mahogany, Pear, Cherry, Plum, Peach, Apple, Elm, Basswood, Sweetgum |
| | Neoptychodes trilineatus | Fig, Alder, Mulberry, Willow, Netleaf hackberry |
| | Oberea ocellata | Sumac, Apple, Peach, Plum, Pear, Currant, Blackberry |
| | Oberea tripunctata | Dogwood, Viburnum, Elm, Sourwood, Blueberry, Rhododendron, Azalea, Laurel, Poplar, Willow, Mulberry |
| | Oncideres cingulata | Hickory, Pecan, Persimmon, Elm, Sourwood, Basswood, Honeylocust, Dogwood, Eucalyptus, Oak, Hackberry, Maple, Fruit trees |
| | Saperda calcarata | Poplar |
| | Strophiona nitens | Chestnut, Oak, Hickory, Walnut, Beech, Maple |
| Scolytidae | Corthylus columbianus | Maple, Oak, Yellow-poplar, Beech, Boxelder, Sycamore, Birch, Basswood, Chestnut, Elm |
| | Dendroctonus frontalis | Pine |
| | Dryocoetes betulae | Birch, Sweetgum, Wild cherry, Beech, Pear |
| | Monarthrum fasciatum | Oak, Maple, Birch, Chestnut, Sweetgum, Blackgum, Poplar, Hickory, Mimosa, Apple, Peach, Pine |
| | Phloeotribus liminaris | Peach, Cherry, Plum, Black cherry, Elm, Mulberry, Mountain-ash |
| | Pseudopityophthorus pruinosus | Oak, American beech, Black cherry, Chickasaw plum, Chestnut, Maple, Hickory, Hornbeam, Hophornbeam |
| Sesiidae | Paranthrene simulans | Oak, American chestnut |
| | Sannina uroceriformis | Persimmon |
| | Synanthedon exitiosa | Peach, Plum, Nectarine, Cherry, Apricot, Almond, Black cherry |
| | Synanthedon pictipes | Peach, Plum, Cherry, Beach, Black Cherry |
| | Synanthedon rubrofascia | Tupelo |
| | Synanthedon scitula | Dogwood, Pecan, Hickory, Oak, Chestnut, Beech, Birch, Black cherry, Elm, Mountain-ash, Viburnum, Willow, Apple, Loquat, Ninebark, Bayberry |
| | Vitacea polistiformis | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as Cyclocephala spp. (e.g. masked chafer, C. lurida), Rhizotrogus spp. (e.g. European chafer, R. majalis), Cotinus spp. (e.g. Green June beetle, C. nitida), Popillia spp. (e.g. Japanese beetle, P. japonica), Phyllophaga spp. (e.g. May/June beetle), Ataenius spp. (e.g. Black turfgrass ataenius, A. spretulus), Maladera spp. (e.g. Asiatic garden beetle, M. castanea) and spp.), ground pearls (Margarodes spp.), mole crickets (tawny, southern, and short-winged; Scapteriscus spp., Gryllotalpa africana) and leatherjackets (European crane fly, Tipula spp.).

The present invention may also be used to control insect pests of turfgrass that are thatch dwelling, including armyworms (such as fall armyworm Spodoptera frugiperda, and common armyworm Pseudaletia unipuncta), cutworms, billbugs (Sphenophorus spp., such as S. venatus verstitus and S. parvulus), and sod webworms (such as Crambus spp. and the tropical sod webworm, Herpetogramma phaeopteralis).

The present invention may also be used to control insect pests of turfgrass that live above the ground and feed on the turfgrass leaves, including chinch bugs (such as southern chinch bugs, Blissus insularis), Bermudagrass mite (Eriophyes cynodoniensis), rhodesgrass mealybug (Antonina graminis), two-lined spittlebug (Propsapia bicincta), leafhoppers, cutworms (Noctuidae family), and greenbugs. The present invention may also be used to control other pests of turfgrass such as red imported fire ants (Solenopsis invicta) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: Haematopinus spp., Linognathus spp., Pediculus spp. and Phtirus spp., Solenopotes spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis*, *Periplaneta americana*, *Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergatesspp.*, *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus*, *Chlorophorus pilosis*, *Anobium punctatum*, *Xestobium rufovillosum*, *Ptilinuspecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthesrugicollis*, *Xyleborus* spec., *Tryptodendron* spec., *Apate monachus*, *Bostrychus capucins*, *Heterobostrychus brunneus*, *Sinoxylon* spec. and *Dinoderus minutus*, and also hymenopterans such as *Sirex juvencus*, *Urocerus gigas*, *Urocerus gigas taignus* and *Urocerus augur*, and termites such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis* and *Coptotermes formosanus*, and bristletails such as *Lepisma saccharina*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophillite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, 10$^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 I/ha, especially from 10 to 1000 I/ha.

Preferred formulations can have the following compositions (weight %):
Emulsifiable Concentrates:
  active ingredient: 1 to 95%, preferably 60 to 90%
  surface-active agent: 1 to 30%, preferably 5 to 20%
  liquid carrier: 1 to 80%, preferable 1 to 35%
Dusts:
  active ingredient: 0.1 to 10%, preferably 0.1 to 5%
  solid carrier: 99.9 to 90%, preferably 99.9 to 99%
Suspension Concentrates:
  active ingredient: 5 to 75%, preferably 10 to 50%
  water: 94 to 24%, preferably 88 to 30%
  surface-active agent: 1 to 40%, preferably 2 to 30%
Wettable Powders:
  active ingredient: 0.5 to 90%, preferably 1 to 80%
  surface-active agent: 0.5 to 20%, preferably 1 to 15%
  solid carrier: 5 to 95%, preferably 15 to 90%
Granules:
  active ingredient: 0.1 to 30%, preferably 0.1 to 15%
  solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent.

The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

"Mp" means melting point in ° C. Free radicals represent methyl groups. $^1$H NMR measurements were recorded on a Brucker 400 MHz spectrometer, chemical shifts are given in ppm relevant to a TMS standard. Spectra measured in deuterated solvents as indicated. Common abbreviations: aq=aqueous, min=minute, h=hour, sat=saturated, $R_f$=retention time, mCPBA=meta-chloroperoxybenzoic acid, MeOH=methanol, EtOH=ethanol, NaHCO$_3$=sodium hydrogen carbonate, Na$_2$CO$_3$=sodium carbonate, HCl=hydrogen chloride, CH$_2$Cl$_2$=dichloromethane, Et$_3$N=triethylamine, DMF=N,N-dimethylformamide. Either one of the LCMS and/or GCMS methods below was used to characterize the compounds. The characteristic LCMS values obtained for each compound were the retention time ("Rt", recorded in minutes) and the measured molecular ion (M+H)$^+$.

LCMS and GCMS Methods:

Method 1:

Spectra were recorded on a Mass Spectrometer from Waters (ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: 0 min 0% B, 100% A; 1.2-1.5 min 100% B; Flow (ml/min) 0.85.

Method 2:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH; gradient: 0 min 0% B, 100% A; 2.7-3.0 min 100% B; Flow (ml/min) 0.85.

Method 3:

GCMS analyses were performed on a Thermo Electron instrument where a TRACE GC ULTRA gas chromatograph (equipped with a Zebron Phenomenex ZB-5 ms 15 m, diam: 0.25 mm, 0.25 µm column; $H_2$ flow 1.2 mL/min; temp injector: 250° C.; temp detector: 220° C.; method: start at 70° C., then 25° C./min until 320° C., hold 2 min at 320° C.) was linked to a DSQ mass spectrometer characterizing the compounds by electron ionisation (EI).

Example P1

Preparation of 5-(4-chlorophenyl)-3-ethylsulfonyl-2-[4-methyl-5-[4-(trifluoromethyl)-2-pyridyl]-1,2,4-triazol-3-yl]pyridine (Compound P2)

Step A-1: Preparation of methyl 5-bromo-3-chloro-pyridine-2-carboxylate

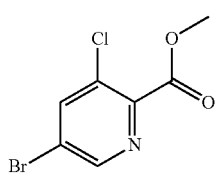

To a slightly cloudy solution of 5-bromo-3-chloro-pyridine-2-carboxylic acid (60 g, 183.2 mmol) in dichloromethane (700 ml) was added dropwise N,N-dimethylformamide (1 ml) and oxalylchloride (24.9 ml, 286.9 mmol). The cloudy solution was stirred for 3 hours at ambient temperature. The resulting yellow solution was cooled to 10° C. and methanol (30.8 ml, 761.3 mmol) was added dropwise to the mixture, keeping the temperature between 15° and 20° C. The solution was stirred overnight at ambient temperature. After neutralisation with an aqueous saturated solution of sodium hydrogen carbonate, the organic layer was washed with brine, dried over sodium sulfate, filtrated and evaporated to give methyl 5-bromo-3-chloro-pyridine-2-carboxylate (55 g) as a yellow solid, which was used without further purification. LCMS (method 2): 250/252/254 (M+H)$^+$, retention time 1.12 min.

Step A-2: Preparation of methyl 3-chloro-5-(4-chlorophenyl)pyridine-2-carboxylate

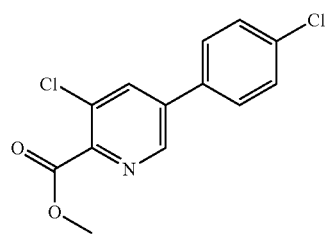 [SMILES: COC(=O)c1ncc(-c2ccc(Cl)cc2)cc1Cl]

A solution of methyl 5-bromo-3-chloro-pyridine-2-carboxylate (17.33 g, 69.2 mmol), 4-chlorophenyl-boronic acid (11.36 g, 72.7 mmol), sodium carbonate (14.7 g, 138.4 mmol) in a mixture of 1,2-dimethoxyethane (500 ml) and water (50 ml) was flushed with argon. Tetrakis(triphenylphosphine) palladium (4.0 g, 3.5 mmol) was added and the mixture was stirred at 90° C. for 7 hours. More catalyst was added (0.5 g, 0.4 mmol) and the mixture was stirred another 2 hours at 90° C. After cooling, the reaction mixture was diluted with water and ethyl acetate. The water phase was separated and washed twice with ethyl acetate. The combined organic phases were dried over magnesium sulfate and evaporated under vacuum. The residue was submitted to flash chromatography to give methyl 3-chloro-5-(4-chlorophenyl)pyridine-2-carboxylate (10.5 g). LCMS (method 2): 282/284 (M+H)$^+$, retention time 1.63 min.

Step A-3: Preparation of 5-(4-chlorophenyl)-3-ethylsulfanyl-pyridine-2-carboxylic Acid

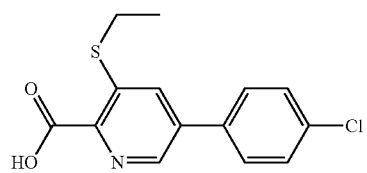

To a solution of methyl 3-chloro-5-(4-chlorophenyl)pyridine-2-carboxylate (2.0 g, 7.1 mmol) in 15 ml N,N-dimethylformamide, sodium ethanethiolate (3.3 g, 35 mmol) was added. The temperature rose to 40° C. and the reaction mixture was stirred 1 hour at room temperature. The solution was diluted with tert-butyl methyl ether and was extracted with ice water. The aqueous phase was separated and neutralized with acetic acid and extracted with tert-butyl methyl ether and ethyl acetate. The combined organic layers were dried over magnesium sulfate and evaporated under vacuum to give 5-(4-chlorophenyl)-3-ethylsulfanyl-pyridine-2-carboxylic acid (2.0 g) which was used without further purification. LCMS (method 2): 294/296 (M+H)$^+$, retention time 1.42 min.

Step A-4: Preparation of methyl 5-(4-chlorophenyl)-3-ethylsulfanyl-pyridine-2-carboxylate

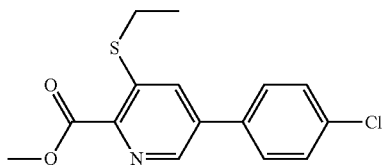 [SMILES: CCSc1cc(-c2ccc(Cl)cc2)cnc1C(=O)OC]

To a solution of 5-(4-chlorophenyl)-3-ethylsulfanyl-pyridine-2-carboxylic acid (220 mg, 0.749 mmol) in methanol (5 ml) was added sulfuric acid (3 drops) and the mixture stirred at reflux overnight. After cooling, the reaction mixture was diluted with iced water and extracted with dichloromethane (5×). The combined organic layers were dried over sodium sulfate and concentrated under reduced pressure. The residue was submitted to flash column chromatography on silica (cyclohexane/ethyl acetate 1:1) to afford methyl 5-(4-chlorophenyl)-3-ethylsulfanyl-pyridine-2-carboxylate (184 mg) as a solid, mp 103-105° C. LCMS (method 2): 308/310 (M+H)$^+$, retention time 1.70 min.

Step A-5: Preparation of 5-(4-chlorophenyl)-3-ethylsulfanyl-pyridine-2-carbohydrazide

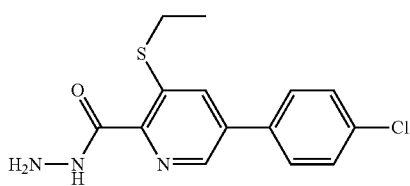 [SMILES: CCSc1cc(-c2ccc(Cl)cc2)cnc1C(=O)NN]

To a solution of methyl 5-(4-chlorophenyl)-3-ethylsulfanyl-pyridine-2-carboxylate (184 mg, 0.598 mmol) in methanol (2 ml) was added hydrazine monohydrate (0.0382 ml, 0.777 mmol) and the mixture stirred at reflux for 3.5 hours. After cooling, the reaction mixture was concentrated under reduced pressure, the residue dissolved in dichloromethane, dried over sodium sulfate and evaporated to dryness to afford 5-(4-chlorophenyl)-3-ethylsulfanyl-pyridine-2-carbohydrazide (145 mg) as a solid, mp 124-126° C. LCMS (method 1): 308/310 (M+H)$^+$, retention time 0.91 min. This material was used without further purification.

Step B-1: Preparation of N,N'-dimethyl-4-(trifluoromethyl)pyridine-2-carboxamidine

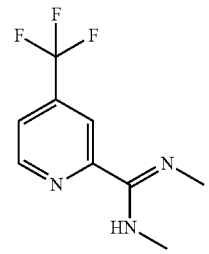

To a solution of 4-(trifluoromethyl)pyridine-2-carbonitrile (1.7 g, 9.88 mmol) in methanol (18 ml) was added sodium methoxide (25 wt % in MeOH) (2.1 g, 9.9 mmol, 2.3 ml) and the mixture stirred at room temperature for 3 hours. The reaction mixture was concentrated to dryness, the residue suspended in methylamine (33 wt % in EtOH) (25 ml, 200.9 mmol) to which was added methylamine hydrochloride (6.7 g, 99.2 mmol). The reaction mixture was heated in a closed high pressure vial at 90° C. overnight. After cooling, the mixture was concentrated and the residue treated with dichloromethane, filtered and the filtrate evaporated under reduced pressure. This material was dissolved in diethyl ether, treated with a 2M hydrochloric acid solution in diethyl ether under cooling, stirred at 5-10° C. for 20 minutes, then diluted with water. The layers were separated and the organic phase washed twice with water. The combined aqueous phases were basified to pH 12 by addition of an aqueous 30% sodium hydroxide solution under cooling, and the product thoroughly extracted with diethyl ether (4×). The combined organic layers were dried over sodium sulfate and concentrated under reduced pressure to afford N,N'-dimethyl-4-(trifluoromethyl)pyridine-2-carboxamidine as an oil (0.70 g), which was used without further purification. LCMS (method 1): 218 (M+H)$^+$, retention time 0.28 min. $^{19}$F-NMR (MeOD, ppm) −66.4.

Step C-1: Preparation of 5-(4-chlorophenyl)-3-ethylsulfanyl-2-[4-methyl-5-[4-(trifluoromethyl)-2-pyridyl]-1,2,4-triazol-3-yl]pyridine (Compound P1)

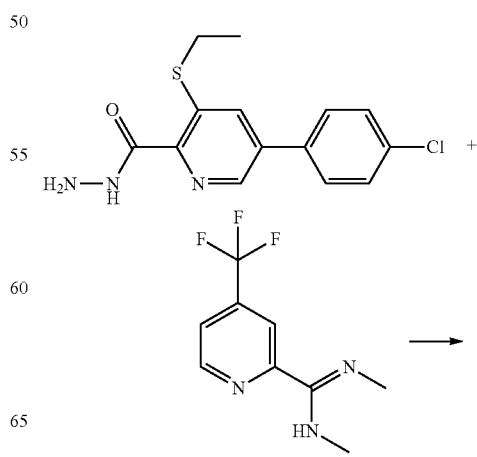

-continued

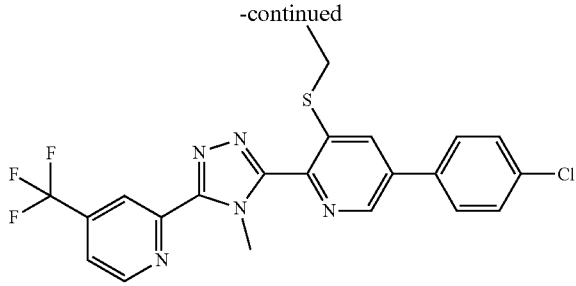

A solution of 5-(4-chlorophenyl)-3-ethylsulfanyl-pyridine-2-carbohydrazide (135 mg, 0.439 mmol) and N,N'-dimethyl-4-(trifluoromethyl)pyridine-2-carboxamidine (95.3 mg, 0.439 mmol) in methanol (3 ml) was heated at reflux temperature overnight. After cooling, the reaction mixture was concentrated under reduced pressure, the residue dissolved in dichloromethane, dried over sodium sulfate and evaporated to dryness. The residue was purified over silica by flash column chromatography (cyclohexane/ethyl acetate 3:1) to afford 5-(4-chlorophenyl)-3-ethylsulfanyl-2-[4-methyl-5-[4-(trifluoromethyl)-2-pyridyl]-1,2,4-triazol-3-yl]pyridine (compound P1) as a solid (96 mg), mp 147-149° C. LCMS (method 2): 476/478 (M+H)+, retention time 1.97 min. $^1$H-NMR (CDCl$_3$, ppm) 1.36 (3H), 3.03 (2H), 4.18 (3H), 7.51 (2H), 7.58 (3H), 7.89 (1H), 8.70 (1H), 8.73 (1H), 8.87 (1H).

Step C-2: Preparation of 5-(4-chlorophenyl)-3-ethylsulfonyl-2-[4-methyl-5-[4-(trifluoromethyl)-2-pyridyl]-1,2,4-triazol-3-yl]pyridine (Title Compound P2)

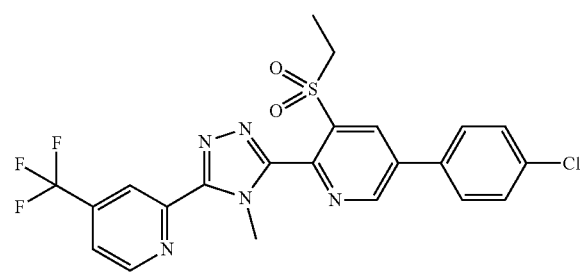 [SMILES: CCS(=O)(=O)c1cc(-c2ccc(Cl)cc2)cnc1-c1nnc(-c2cc(C(F)(F)F)ccn2)n1C]

To a solution of 5-(4-chlorophenyl)-3-ethylsulfanyl-2-[4-methyl-5-[4-(trifluoromethyl)-2-pyridyl]-1,2,4-triazol-3-yl] pyridine (65 mg, 0.137 mmol) in dichloromethane (2 ml) at 10° C. was added mCPBA (75 wt % in water) (66 mg, 0.287 mmol, 75%) in one portion and the mixture was stirred at 10° C. for 2 hours. The reaction mixture was diluted with tert-butyl methyl ether, washed successively with sat. aqueous sodium hydrogen carbonate (4×), a sat. aqueous sodium sodium bisulfite solution (4×) and brine, dried over sodium sulfate and concentrated under reduced pressure. The residue was purified over silica by flash column chromatography (cyclohexane/ethyl acetate 3:1) to afford 5-(4-chlorophenyl)-3-ethylsulfonyl-2-[4-methyl-5-[4-(trifluoromethyl)-2-pyridyl]-1,2,4-triazol-3-yl]pyridine (title compound P2) as a solid (32 mg), mp 234-235° C. LCMS (method 2): 508/510 (M+H)+, retention time 1.81 min. $^1$H-NMR (CDCl$_3$, ppm) 1.40 (3H), 3.86 (2H), 4.10 (3H), 7.56 (2H), 7.60 (1H), 7.67 (2H), 8.66 (1H), 8.72 (1H), 8.87 (1H), 9.18 (1H).

Example P2

Preparation of 3-ethylsulfonyl-2-[4-methyl-5-[4-(trifluoromethyl)-2-pyridyl]-1,2,4-triazol-3-yl]-5-pyrazol-1-yl-pyridine (Compound P4)

Step A-1: Preparation of 5-bromo-3-chloro-pyridine-2-carbohydrazide

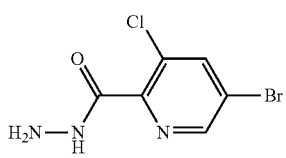

Obtained from methyl 5-bromo-3-chloro-pyridine-2-carboxylate (34 g, 135.7 mmol) and hydrazine hydrate (8.75 ml, 176.5 mmol) in methanol (350 ml) according to procedure Example P1, step A-5. The mixture was stirred at reflux temperature for 4 hours. The solid residue obtained after workup was suspended in diethyl ether, filtered, the solid washed with cold diethyl ether and dried in vacuo to afford 5-bromo-3-chloro-pyridine-2-carbohydrazide (32.1 g) as a solid, mp 146-148° C. LCMS (method 2): 250/252/254 (M+H)+; retention time: 0.47 min. $^1$H-NMR (DMSO-d$_6$, ppm) 4.59 (br s, 2H), 8.45 (s, 1H), 8.68 (s, 1H), 9.77 (br s, 1H).

Step B-1: Preparation of 5-bromo-3-chloro-2-[4-methyl-5-[4-(trifluoromethyl)-2-pyridyl]-1,2,4-triazol-3-yl]pyridine

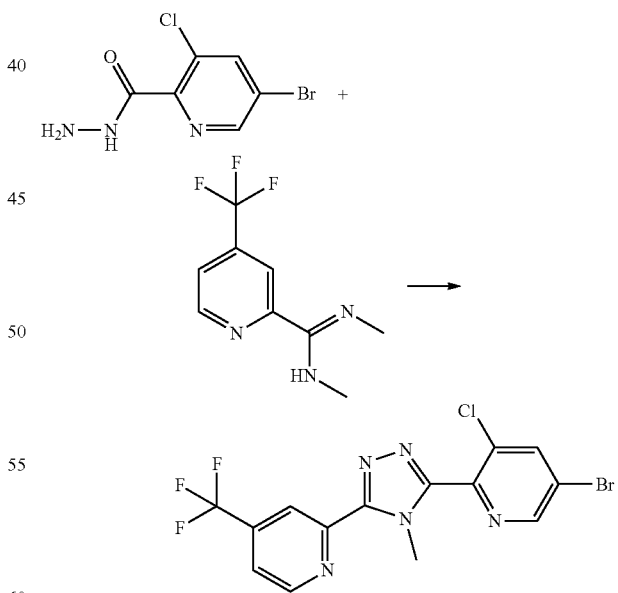

Obtained from 5-bromo-3-chloro-pyridine-2-carbohydrazide (554 mg, 2.21 mmol) and N,N'-dimethyl-4-(trifluoromethyl)pyridine-2-carboxamidine (480 mg, 2.21 mmol) in methanol (4 ml) according to procedure Example P1, step C-1. The mixture was stirred at reflux overnight. Flash chromatography purification (cyclohexane/ethyl acetate 4:1)

afforded 5-bromo-3-chloro-2-[4-methyl-5-[4-(trifluoromethyl)-2-pyridyl]-1,2,4-triazol-3-yl]pyridine (560 mg) as a solid, mp 152-154° C. LCMS (method 2): 418/420/422 (M+H)⁺; retention time: 1.53 min. ¹H-NMR (CDCl₃, ppm) 4.10 (s, 3H), 7.60 (d, 1H), 8.13 (d, 1H), 8.70 (s, 1H), 8.75 (d, 1H), 8.87 (d, 1H).

Step B-2: Preparation of 3-chloro-2-[4-methyl-5-[4-(trifluoromethyl)-2-pyridyl]-1,2,4-triazol-3-yl]-5-pyrazol-1-yl-pyridine

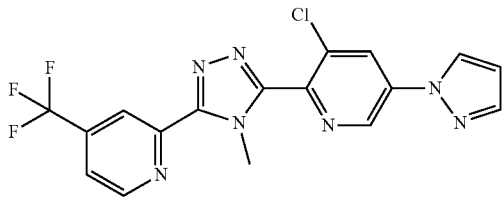 [SMILES: Cn1c(-c2cc(C(F)(F)F)ccn2)nnc1-c1ncc(-n2cccn2)cc1Cl]

To a solution of 5-bromo-3-chloro-2-[4-methyl-5-[4-(trifluoromethyl)-2-pyridyl]-1,2,4-triazol-3-yl]pyridine (250 mg, 0.597 mmol) and 1H-pyrazole (44.7 mg, 0.657 mmol) in N,N-dimethylformamide (2 ml) under argon was added copper(I) iodide (5.7 mg, 0.030 mmol), N,N'-dimethylethylenediamine (5.3 mg, 6.36 µl, 0.060 mmol) and potassium carbonate (16.5 mg, 0.119 mmol). The mixture was stirred at 100° C. for 4 hours. After cooling, the reaction mixture was diluted with ethyl acetate and filtered over diatomaceous earth (Hyflo). The filtrate was washed with water (3×), dried over sodium sulfate and concentrated in vacuo. The residue was purified over silica by flash column chromatography (cyclohexane/ethyl acetate 4:1) to afford 3-chloro-2-[4-methyl-5-[4-(trifluoro-methyl)-2-pyridyl]-1,2,4-triazol-3-yl]-5-pyrazol-1-yl-pyridine as a solid (123 mg), mp 160-162° C. LCMS (method 2): 406/408 (M+H)⁺; retention time: 1.43 min. ¹H-NMR (CDCl₃, ppm) 4.12 (s, 3H), 6.61 (t, 1H), 7.60 (d, 1H), 7.85 (d, 1H), 8.08 (d, 1H), 8.36 (d, 1H), 8.72 (s, 1H), 8.88 (d, 1H), 9.08 (d, 1H).

Step B-3: Preparation of 3-ethylsulfanyl-2-[4-methyl-5-[4-(trifluoromethyl)-2-pyridyl]-1,2,4-triazol-3-yl]-5-pyrazol-1-yl-pyridine (Compound P3)

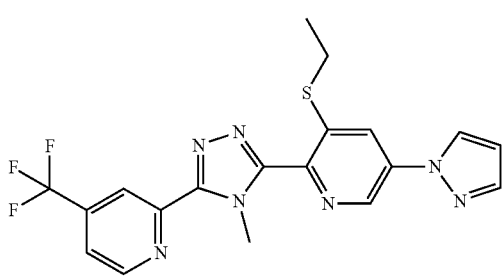 [SMILES: CCSc1cc(-n2cccn2)cnc1-c1nnc(-c2cc(C(F)(F)F)ccn2)n1C]

To a solution of 3-chloro-2-[4-methyl-5-[4-(trifluoromethyl)-2-pyridyl]-1,2,4-triazol-3-yl]-5-pyrazol-1-yl-pyridine (123 mg, 0.303 mmol) in N,N-dimethylformamide (2.5 ml) at 10° C. was added sodium ethanethiolate (38.6 mg, 0.458 mmol) in one portion. The reaction mixture was stirred at 50° C. overnight, then concentrated to dryness under reduced pressure. The residue was diluted with ethyl acetate and water, the layers separated, the organic phase washed with water (3×), dried over sodium sulfate and concentrated in vacuo. The solid residue was stirred in diethyl ether, filtered, washed with cold diethyl ether and dried in vacuo to afford 3-ethylsulfanyl-2-[4-methyl-5-[4-(trifluoromethyl)-2-pyridyl]-1,2,4-triazol-3-yl]-5-pyrazol-1-yl-pyridine (compound P3) as a solid (101 mg), mp 121-123° C. LCMS (method 2): 432 (M+H)⁺; retention time: 1.54 min. ¹H-NMR (CDCl₃, ppm) 1.39 (t, 3H), 3.06 (q, 2H), 4.16 (s, 3H), 6.59 (t, 1H), 7.58 (d, 1H), 7.83 (d, 1H), 8.07 (d, 1H), 8.19 (d, 1H), 8.72 (s, 1H), 8.83 (d, 1H), 8.87 (d, 1H).

Step B-4: Preparation of 3-ethylsulfonyl-2-[4-methyl-5-[4-(trifluoromethyl)-2-pyridyl]-1,2,4-triazol-3-yl]-5-pyrazol-1-yl-pyridine (Compound P4)

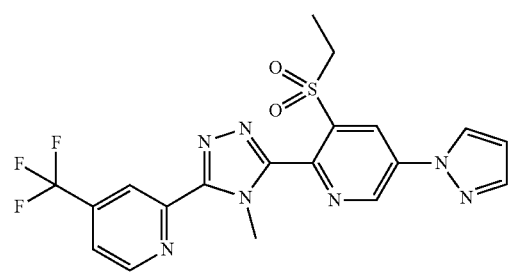 [SMILES: CCS(=O)(=O)c1cc(-n2cccn2)cnc1-c1nnc(-c2cc(C(F)(F)F)ccn2)n1C]

Obtained from 3-ethylsulfanyl-2-[4-methyl-5-[4-(trifluoromethyl)-2-pyridyl]-1,2,4-triazol-3-yl]-5-pyrazol-1-yl-pyridine (95 mg, 0.220 mmol) and mCPBA (106 mg, 0.462 mmol, 75%) in dichloromethane (2.5 ml) according to procedure Example P1, step C-2. The mixture was stirred at room temperature overnight. Flash chromatography purification (cyclohexane/ethyl acetate 3:1) afforded 3-ethylsulfonyl-2-[4-methyl-5-[4-(trifluoromethyl)-2-pyridyl]-1,2,4-triazol-3-yl]-5-pyrazol-1-yl-pyridine (title compound P4) as a solid (52 mg), mp 174-176° C. LCMS (method 2): 464 (M+H)⁺; retention time: 1.43 min. ¹H-NMR (CDCl₃, ppm) 1.41 (t, 3H), 3.88 (q, 2H), 4.08 (s, 3H), 6.65 (t, 1H), 7.60 (d, 1H), 7.89 (d, 1H), 8.15 (d, 1H), 8.71 (s, 1H), 8.77 (d, 1H), 8.87 (d, 1H), 9.47 (d, 1H).

Example P3

Preparation of 3-ethylsulfonyl-2-[4-methyl-5-[4-(trifluoromethyl)-2-pyridyl]-1,2,4-triazol-3-yl]-5-vinyl-pyridine (Compound P12)

Step A-1: Preparation of N-methyl-4-(trifluoromethyl)pyridine-2-carboxamide

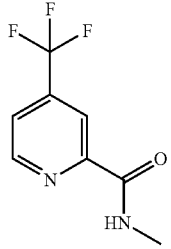

To a solution of 4-(trifluoromethyl)pyridine-2-carboxylic acid (97%, 10.0 g, 50.76 mmol) in dichloromethane (200 ml) was added dropwise N,N-dimethylformamide (0.1 ml) and oxalyl chloride (5.66 ml, 66.00 mmol). The reaction mixture was stirred at ambient temperature overnight, then concentrated to dryness in vacuo to afford 4-(trifluoromethyl)pyridine-2-carbonyl chloride (10.5 g) as a solid.

To methylamine (2M in tetrahydrofuran) (62.6 ml, 125.2 mmol) in tetrahydrofuran (40 ml) at 0-5° C. was added triethylamine (10.4 ml, 75.03 mmol), followed by a solution of 4-(trifluoromethyl)pyridine-2-carbonyl chloride (10.5 g, 50.11 mmol, preparation above) in tetrahydrofuran (60 ml) dropwise. The mixture was allowed to warm to room temperature, and stirred for 2 hours. The resulting suspension was filtered, the solid residue washed with t-butyl methyl ether (3×) and the filtrate evaporated under reduced pressure. The residue was dissolved in t-butyl methyl ether, the organic phase washed with water (3×) and brine, dried over sodium sulfate and concentrated in vacuo. The crude material was diluted with t-butyl methyl ether, treated with activated charcoal, the mixture stirred for 15 minutes and filtered. Evaporation of the filtrate in vacuo afforded N-methyl-4-(trifluoromethyl)pyridine-2-carboxamide as a solid (9.2 g), mp 60-62° C. This material was used without further purification. LCMS (method 2): 205 (M+H)$^+$; retention time: 0.86 min. $^1$H-NMR (CDCl$_3$, ppm) 3.07 (d, 3H), 7.66 (d, 1H), 8.01 (br s, 1H), 8.45 (s, 1H), 8.74 (d, 1H).

Step A-2: Preparation of N-methyl-4-(trifluoromethyl)pyridine-2-carbothioamide

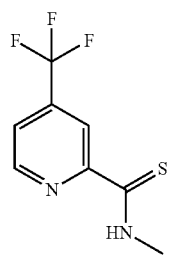

To a solution of N-methyl-4-(trifluoromethyl)pyridine-2-carboxamide (32.5 g, 159.2 mmol) in pyridine (870 ml) was added phosphorus pentasulfide (42.5 g, 95.6 mmol) and the mixture was stirred at reflux temperature for 5 hours. After cooling, the solvent was removed in vacuo, the residue diluted with water and the aqueous phase extracted with diethyl ether (3×). The combined organic layers were washed with a water/brine (1:1) solution (4×), dried over sodium sulfate and concentrated under reduced pressure to afford N-methyl-4-(trifluoromethyl)pyridine-2-carbothioamide as a solid (30.9 g), mp 69-70° C. This material was used without further purification. LCMS (method 2): 221 (M+H)$^+$; retention time: 1.42 min. $^1$H-NMR (CDCl$_3$, ppm) 3.43 (d, 3H), 7.66 (d, 1H), 8.68 (d, 1H), 8.96 (s, 1H), 10.14 (br s, 1H).

Step A-3: Preparation of ethyl N-methyl-4-(trifluoromethyl)pyridine-2-carboximidothioate

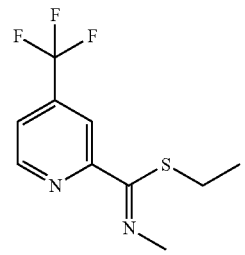 [SMILES: CCS/C(=N\C)c1cc(C(F)(F)F)ccn1]

To a solution of N-methyl-4-(trifluoromethyl)pyridine-2-carbothioamide (10.2 g, 46.32 mmol) in ethanol (200 ml) was added sodium ethoxide (21 wt % in EtOH) (15.2 g, 46.3 mmol, 17.3 ml) and the mixture was stirred at room temperature for 40 minutes. Iodoethane (14.5 g, 92.68 mmol, 7.49 ml) was added and stirring continued at room temperature overnight. The reaction mixture was concentrated in vacuo, diluted with t-butyl methyl ether, the organic phase washed successively with water (3×), a sat. aqueous sodium carbonate solution and brine, dried over sodium sulfate and evaporated under reduced pressure to afford ethyl N-methyl-4-(trifluoromethyl)pyridine-2-carboximidothioate, as a liquid (10.4 g). This material was used without further purification LCMS (method 2): 249 (M+H)$^+$; retention time: 1.20 min. $^1$H-NMR (CDCl$_3$, ppm, major isomer) 1.15 (t, 3H), 2.87 (q, 2H), 3.53 (s, 3H), 7.55 (d, 1H), 7.91 (s, 1H), 8.84 (d, 1H).

Step B-1: Preparation of 5-bromo-3-ethylsulfanyl-pyridine-2-carbonitrile

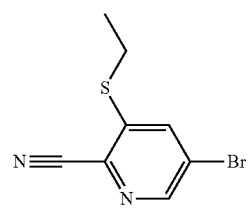

Under nitrogen atmosphere, a solution of 5-bromo-3-fluoro-pyridine-2-carbonitrile (1.005 g, 5.00 mmol) in dry N,N-dimethylformamide (15 ml) was cooled to −50° C. and to this was added dropwise a freshly prepared solution of sodium ethanethiolate (0.429 g, 5.10 mmol) in dry N,N-dimethylformamide (5 ml). After stirring at −50° C. for 30 minutes, the cooling bath was removed and the mixture was allowed to warm to room temperature. Water and brine were added and the aqueous mixture was extracted with ethyl acetate. After separation, the organic layer was washed twice with brine, dried over sodium sulfate and concentrated. The crude product was purified over silica by flash column chromatography (0 to 40% gradient of ethyl acetate in heptane) to afford the title compound (0.93 g) as a solid. GCMS (method 3): 242/244 (M)$^+$, retention time 6.33 min. $^1$H-NMR (CDCl$_3$, ppm) 1.41 (3H), 3.06 (2H), 7.82 (1H), 8.49 (1H).

Alternative preparation method: Under nitrogen atmosphere, a solution of 5-bromo-3-nitro-pyridine-2-carbonitrile (45.35 g, 199 mmol) in dry N,N-dimethylformamide (500 ml) was cooled to −50° C. and to this was added dropwise a freshly prepared solution of sodium ethanethiolate (17.4 g, 207 mmol) in dry N,N-dimethylformamide (200 ml) (not a completely clear solution). After complete addition, stirring was continued at −50° C. for 30 minutes. Water and brine were added and the cooling bath was removed. The aqueous mixture was extracted with ethyl acetate. After separation, the water layer was extracted with ethyl acetate once more. The combined the organic layers were washed twice with brine, dried over sodium sulfate and concentrated. The crude product was purified over silica by flash column chromatography (0 to 25% gradient of ethyl acetate in heptane) to afford the title compound (33.9 g) as a solid. LCMS (method 1): 243/245 (M+H)$^+$; retention time: 0.95 min.

Step B-2: Preparation of
5-bromo-3-ethylsulfanyl-pyridine-2-carboxylic Acid

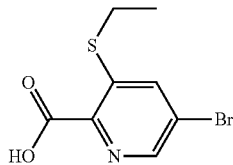

A solution of 5-bromo-3-ethylsulfanyl-pyridine-2-carbonitrile (43 g, 170 mmol, 1.0 eq.) in 800 ml aqueous hydrogen chloride HCl 32% was heated to 60° C. overnight. Dioxane (100 ml) was added and the mixture was further stirred at 60° C. for 48 h. The reaction mixture was cooled to 0-5° C., treated with an aqueous sodium hydroxide solution (NaOH 30%) until pH11 and washed with 2×200 ml tert-butyl methyl ether. The water phase was acidified with HCl 10% back to pH4, the resulting solid was filtrated, washed with water and dried in vacuo. LCMS (method 1): 262, 264 (M+H)$^+$; retention time: 0.77 min. $^1$H NMR (400 MHz, CDCl$_3$) δ ppm: 8.50 (s, 1H); 8.06 (s, 1H); 3.03 (q, 2H); 1.24 (t, 3H).

Step B-3: Preparation of methyl
5-bromo-3-ethylsulfanyl-pyridine-2-carboxylate

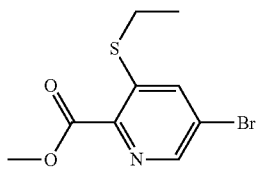

To a suspension of 5-bromo-3-ethylsulfanyl-pyridine-2-carboxylic acid (15.0 g, 57.23 mmol) in methanol (350 ml) was added sulfuric acid (0.5 ml) and the mixture stirred at reflux overnight. After cooling, the solution was concentrated under reduced pressure. The residue was triturated with diethyl ether (200 ml), the suspension filtered, the solid washed with cold diethyl ether and dried in vacuo to afford methyl 5-bromo-3-ethylsulfanyl-pyridine-2-carboxylate (13.9 g) as a solid, mp 72-74° C. LCMS (method 1): 276/278 (M+H)$^+$, retention time 0.98 min. $^1$H-NMR (CDCl$_3$, ppm) 1.42 (3H), 2.94 (2H), 4.00 (3H), 7.78 (1H), 8.46 (1H).

Step B-4: Preparation of
5-bromo-3-ethylsulfanyl-pyridine-2-carbohydrazide

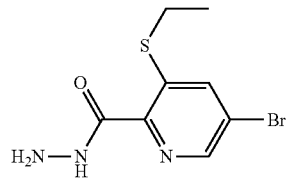

To a solution of methyl 5-bromo-3-ethylsulfanyl-pyridine-2-carboxylate (19.8 g, 71.70 mmol) in methanol (300 ml) was added hydrazine monohydrate (4.62 ml, 93.2 mmol) and the mixture stirred at reflux for 4 hours. After cooling, the reaction mixture was concentrated under reduced pressure, the residue suspended in diethyl ether, filtered and the solid washed with cold diethyl ether and dried in vacuo to afford 5-bromo-3-ethylsulfanyl-pyridine-2-carbohydrazide (17.2 g) as a solid, mp 136-138° C. LCMS (method 1): 276/278 (M+H)$^+$, retention time 0.75 min. $^1$H-NMR (CDCl$_3$, ppm) 1.42 (3H), 2.91 (2H), 4.02 (2H), 7.75 (1H), 8.28 (1H), 8.82 (1H).

Step C-1: Preparation of 5-bromo-3-ethylsulfanyl-2-
[4-methyl-5-[4-(trifluoromethyl)-2-pyridyl]-1,2,4-
triazol-3-yl]pyridine

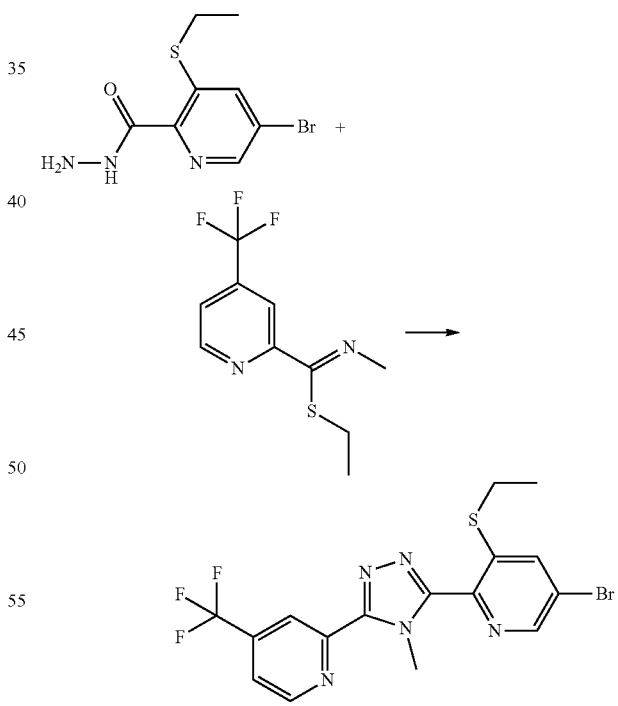

A solution of 5-bromo-3-ethylsulfanyl-pyridine-2-carbohydrazide (556 mg, 2.014 mmol) and ethyl N-methyl-4-(trifluoromethyl)pyridine-2-carboximidothioate (500 mg, 2.014 mmol) in ethanol (5 ml) was heated in the microwave at 150° C. for 30 minutes. After cooling, the reaction mixture was concentrated under reduced pressure and the residue purified over silica by flash column chromatography (0-25% ethyl acetate gradient in cyclohexane) to afford 5-bromo-3-ethylsulfanyl-2-[4-methyl-5-[4-(trifluoro-methyl)-2-pyridyl]-1,2,4-triazol-3-yl]pyridine as a solid (700 mg), mp 122-123° C. LCMS (method 1): 444/446 (M+H)$^+$, retention time 1.04 min. $^1$H-NMR (CDCl$_3$, ppm) 1.36 (3H), 2.97 (2H), 4.14 (3H), 7.58 (1H), 7.86 (1H), 8.55 (1H), 8.70 (1H), 8.87 (1H).

Alternative preparation method: To a solution of ethyl N-methyl-4-(trifluoromethyl)pyridine-2-carboximidothioate (3.0 g, estimated 90%, 10.88 mmol) in pyridine (12 ml) which was purged with argon for 10 minutes was added 5-bromo-3-ethylsulfanyl-pyridine-2-carbohydrazide (3.0 g, 10.88 mmol). The mixture was heated in the microwave at 180° C. for 40 minutes. After cooling, the reaction mixture was poured into ice-water, stirred for 10 minutes, the suspension filtered and the solid washed with cold water. This solid was dissolved in dichloromethane, the solution dried over sodium sulfate and concentrated to dryness under reduced pressure to afford 5-bromo-3-ethylsulfanyl-2-[4-methyl-5-[4-(trifluoro-methyl)-2-pyridyl]-1,2,4-triazol-3-yl]pyridine as a solid (4.3 g), which was used without further purification.

Step C-2: Preparation of 5-bromo-3-ethylsulfonyl-2-[4-methyl-5-[4-(trifluoromethyl)-2-pyridyl]-1,2,4-triazol-3-yl]pyridine

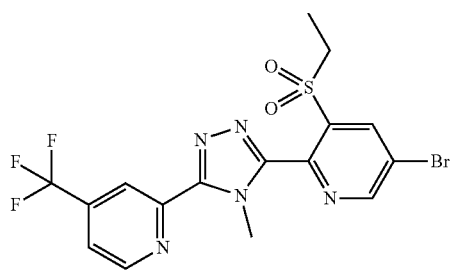 [SMILES: CCS(=O)(=O)c1cc(Br)cnc1-c1nnc(-c2cc(C(F)(F)F)ccn2)n1C]

To a solution of 5-bromo-3-ethylsulfanyl-2-[4-methyl-5-[4-(trifluoromethyl)-2-pyridyl]-1,2,4-triazol-3-yl]pyridine (4.0 g, 9.00 mmol) in dichloromethane (50 ml) at 10° C. was added mCPBA (75 wt % in water) (4.25 g, 18.46 mmol, 75%) in four portions and the mixture was stirred at 5° C. for 2 hours, then at room temperature overnight. The reaction mixture was diluted with tert-butyl methyl ether, washed successively with a sat. aqueous sodium sodium bisulfite solution (2×), sat. aqueous sodium hydrogen carbonate (4×) and brine, dried over sodium sulfate and concentrated under reduced pressure. The residue was triturated with diethyl ether, the suspension filtered, the solid washed with cold diethyl ether and dried in vacuo to afford 5-bromo-3-ethylsulfonyl-2-[4-methyl-5-[4-(trifluoromethyl)-2-pyridyl]-1,2,4-triazol-3-yl]pyridine as a solid (3.6 g), mp 173-175° C. LCMS (method 1): 476/478 (M+H)$^+$, retention time 1.03 min. $^1$H-NMR (CDCl$_3$, ppm) 1.39 (3H), 3.85 (2H), 4.07 (3H), 7.59 (1H), 8.66 (1H), 8.69 (1H), 8.87 (1H), 9.06 (1H).

Step C-3: Preparation of 3-ethylsulfonyl-2-[4-methyl-5-[4-(trifluoromethyl)-2-pyridyl]-1,2,4-triazol-3-yl]-5-vinyl-pyridine (Compound P12)

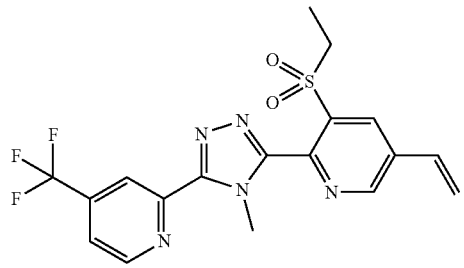 [SMILES: C=Cc1cnc(-c2nnc(-c3cc(C(F)(F)F)ccn3)n2C)c(S(=O)(=O)CC)c1]

Each of two microwave vials were charged with 5-bromo-3-ethylsulfonyl-2-[4-methyl-5-[4-(trifluoro-methyl)-2-pyridyl]-1,2,4-triazol-3-yl]pyridine (500 mg, 1.050 mmol), dibutoxy(vinyl)borane (0.477 ml, 2.10 mmol) and an aqueous 2M sodium carbonate solution (1.57 ml, 2.0M, 3.14 mmol) in acetonitrile (12 ml). Each mixture was purged with argon for 5 minutes, then chloro(2-dicyclohexylphosphino-2',4', 6'-triisopropyl-1,1'-biphenyl)[2-(2'-amino-1,1'-biphenyl)]palladium(II) (82 mg, 0.105 mmol) was added, the vials were capped and stirred in the microwave at 120° C. for 10 minutes. Both reactions were pooled for workup: after dilution with sat. aqueous sodium hydrogen carbonate, the mixture was extracted twice with dichloromethane, the combined organic layers dried over sodium sulfate and concentrated. The residue was purified over silica by flash column chromatography (0-70% ethyl acetate gradient in cyclohexane) to afford 3-ethylsulfonyl-2-[4-methyl-5-[4-(trifluoromethyl)-2-pyridyl]-1,2,4-triazol-3-yl]-5-vinyl-pyridine (title compound P12) as a solid (615 mg), mp 67-70° C. LCMS (method 1): 424 (M+H)$^+$, retention time 0.97 min. $^1$H-NMR (CDCl$_3$, ppm) 1.38 (3H), 3.82 (2H), 4.06 (3H), 5.70 (d, 1H), 6.12 (d, 1H), 6.86 (dd, 1H), 7.59 (1H), 8.50 (1H), 8.70 (1H), 8.86 (1H), 8.97 (1H).

Example P4

Preparation of 5-(6-chloro-2-pyridyl)-3-ethylsulfonyl-2-[4-methyl-5-[4-(trifluoromethyl)-2-pyridyl]-1,2,4-triazol-3-yl]pyridine (Compound P24)

Step 1: Preparation of 3-ethylsulfonyl-2-[4-methyl-5-[4-(trifluoromethyl)-2-pyridyl]-1,2,4-triazol-3-yl]-5-(4,4,5,5-tetramethyl-1,3,2-dioxaborolan-2-yl)pyridine (Compound Z9)

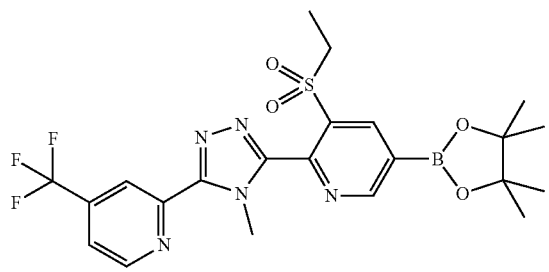 [SMILES: CCS(=O)(=O)c1cc(B2OC(C)(C)C(C)(C)O2)cnc1-c1nnc(-c2cc(C(F)(F)F)ccn2)n1C]

A mixture of 5-bromo-3-ethylsulfonyl-2-[4-methyl-5-[4-(trifluoromethyl)-2-pyridyl]-1,2,4-triazol-3-yl]pyridine (1.50 g, 3.15 mmol), potassium acetate (0.805 g, 7.87 mmol) and 4,4,5,5-tetramethyl-2-(4,4,5,5-tetramethyl-1,3,2-dioxaborolan-2-yl)-1,3,2-dioxaborolane (1.06 g, 4.09 mmol) in dioxane (10 ml) was purged with argon for 10 minutes. 1,1'-Bis(diphenylphosphino)ferrocene-palladium(II) dichloride dichloromethane complex (1:1; PdCl$_2$(dppf).CH$_2$Cl$_2$) (129.9 mg, 0.158 mmol) was then added, and the mixture was stirred in the microwave at 110° C. for 30 minutes. The reaction mixture was diluted with water (50 ml) and extracted with ethyl acetate (5×). The combined organic phases were dried over sodium sulfate and concentrated under reduced pressure. The residue was triturated with diethyl ether, the suspension filtered, the solid washed with cold diethyl ether and dried in vacuo to afford 3-ethylsulfonyl-2-[4-methyl-5-[4-(trifluoromethyl)-2-pyridyl]-1,2,4-triazol-3-yl]-5-(4,4,5,5-tetramethyl-1,3,2-dioxaborolan-2-yl)pyridine as a solid (1.12 g), mp 234-236° C. LCMS (method 1): 442 (M+H)$^+$, retention time 0.83 min [consistent with the corresponding boronic acid of formula C$_{16}$H$_{15}$BF$_3$N$_5$O$_4$S, MW: 441.19]. $^1$H-NMR (CDCl$_3$, ppm) 1.38 (3H), 1.40 (12H), 3.79 (2H), 4.05 (3H), 7.58 (1H), 8.70 (1H), 8.86 (2H), 9.27 (1H).

Step 2 : Preparation of 5-(6-chloro-2-pyridyl)-3-ethylsulfonyl-2-[4-methyl-5-[4-(trifluoromethyl)-2-pyridyl]-1,2,4-triazol-3-yl]pyridine (Compound P24)

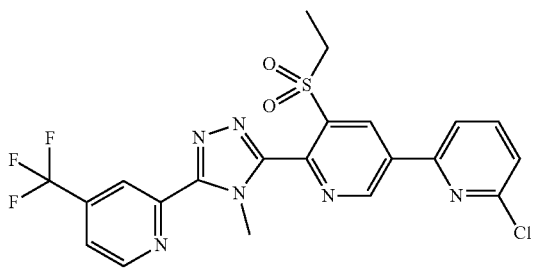 [SMILES: CCS(=O)(=O)c1cc(-c2cccc(Cl)n2)cnc1-c1nnc(-c2cc(C(F)(F)F)ccn2)n1C]

A mixture of 3-ethylsulfonyl-2-[4-methyl-5-[4-(trifluoromethyl)-2-pyridyl]-1,2,4-triazol-3-yl]-5-(4,4,5,5-tetramethyl-1,3,2-dioxaborolan-2-yl)pyridine (200 mg, 0.382 mmol), 2-bromo-6-chloro-pyridine (184 mg, 0.955 mmol) and an aqueous 2M sodium carbonate solution (0.573 ml, 2.0M, 1.15 mmol) in dioxane (2 ml) was purged with argon for 10 minutes. Tetrakis(triphenylphosphine)palladium(0) (22.3 mg, 0.019 mmol) was then added, and the mixture was stirred in the microwave at 85° C. for 40 minutes. The reaction mixture was diluted with tert-butyl methyl ether, filtered over diatomaceous earth (Hyflo), the filtrate dried over sodium sulfate and concentrated to dryness under reduced pressure.

The residue was purified over silica by flash column chromatography (0-30% ethyl acetate gradient in cyclohexane) to afford 5-(6-chloro-2-pyridyl)-3-ethylsulfonyl-2-[4-methyl-5-[4-(trifluoromethyl)-2-pyridyl]-1,2,4-triazol-3-yl]pyridine (title compound P24) as a solid (120 mg), mp 172-174° C. LCMS (method 1): 509/511 (M+H)$^+$, retention time 1.10 min. $^1$H-NMR (CDCl$_3$, ppm) 1.42 (3H), 3.89 (2H), 4.10 (3H), 7.46 (1H), 7.59 (1H), 7.84-7.90 (2H), 8.71 (1H), 8.87 (1H), 9.05 (1H), 9.63 (1H).

Example P5

Preparation of 5-cyclopropyl-3-ethylsulfonyl-2-[4-methyl-5-[4-(trifluoromethyl)-2-pyridyl]-1,2,4-triazol-3-yl]pyridine (Compound P29)

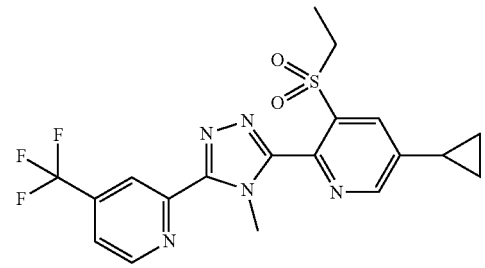 [SMILES: CCS(=O)(=O)c1cc(C2CC2)cnc1-c1nnc(-c2cc(C(F)(F)F)ccn2)n1C]

A mixture of 5-bromo-3-ethylsulfonyl-2-[4-methyl-5-[4-(trifluoromethyl)-2-pyridyl]-1,2,4-triazol-3-yl]pyridine (250 mg, 0.525 mmol), cyclopropylboronic acid (162 mg, 1.89 mmol) and tripotassium phosphate (689 mg, 3.15 mmol) in toluene/water (2 ml/2 ml) was purged with argon for 10 minutes. Tetrakis(triphenylphosphine)palladium(0) (61.3 mg, 0.053 mmol) was then added, and the mixture was stirred in the microwave at 130° C. for a total of 12 hours. The reaction mixture was concentrated, the residue diluted with tert-butyl methyl ether, the organic phase washed twice with water, dried over sodium sulfate and evaporated to dryness. The residue was purified over silica by flash column chromatography (0-35% ethyl acetate gradient in cyclohexane) to afford 5-cyclopropyl-3-ethylsulfonyl-2-[4-methyl-5-[4-(trifluoromethyl)-2-pyridyl]-1,2,4-triazol-3-yl]pyridine (title compound P29) as a solid (90 mg). LCMS (method 2): 438 (M+H)$^+$, retention time 1.53 min. $^1$H-NMR (CDCl$_3$, ppm) 0.95 (2H), 1.25 (2H), 1.35 (3H), 2.12 (1H), 3.76 (2H), 4.02 (3H), 7.57 (1H), 8.06 (1H), 8.69 (1H), 8.76 (1H), 8.85 (1H).

Example P6

Preparation of 2-[5-ethylsulfonyl-6-[4-methyl-5-[4-(trifluoromethyl)-2-pyridyl]-1,2,4-triazol-3-yl]-3-pyridyl]pyrimidine (Compound P9)

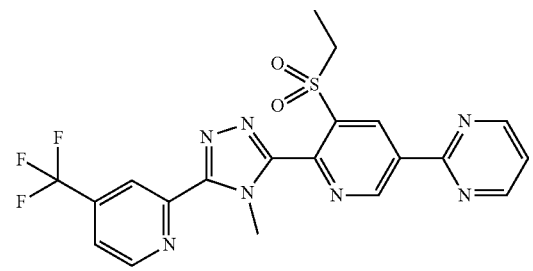 [SMILES: CCS(=O)(=O)c1cc(-c2ncccn2)cnc1-c1nnc(-c2cc(C(F)(F)F)ccn2)n1C]

A mixture of 3-ethylsulfonyl-2-[4-methyl-5-[4-(trifluoromethyl)-2-pyridyl]-1,2,4-triazol-3-yl]-5-(4,4,5,5-tetramethyl-1,3,2-dioxaborolan-2-yl)pyridine (200 mg, 0.382 mmol), 2-bromopyrimidine (151.9 mg, 0.956 mmol) and an aqueous 2M sodium carbonate solution (0.573 ml, 2.0M, 1.15 mmol) in dioxane (2 ml) was purged with argon for 10 minutes. Tetrakis(triphenylphosphine)palladium(0) (22.3 mg, 0.019 mmol) was then added, and the mixture was stirred in the microwave at 85° C. for 40 minutes. The reaction mixture was diluted with water and extracted with ethyl acetate (4×), the combined organic phases were washed with water and brine, dried over sodium sulfate and concentrated under reduced pressure. The residue was purified over silica by flash column chromatography (cyclohexane/ethyl acetate 3:1) to afford 2-[5-ethylsulfonyl-6-[4-methyl-5-[4-(trifluoromethyl)-2-pyridyl]-1,2,4-triazol-3-yl]-3-pyridyl]pyrimidine (title compound P9) as a solid (117.6 mg), mp 191-193° C. LCMS (method 2): 476 (M+H)$^+$, retention time 1.38 min. $^1$H-NMR (CDCl$_3$, ppm) 1.43 (3H), 3.87 (2H), 4.11 (3H), 7.39 (1H), 7.59 (1H), 8.72 (1H), 8.87 (1H), 8.93 (2H), 9.52 (1H), 10.00 (1H).

Example P7

Preparation of 1-[5-ethylsulfonyl-6-[4-methyl-5-[4-(trifluoromethyl)-2-pyridyl]-1,2,4-triazol-3-yl]-3-pyridyl]pyrazole-4-carbonitrile (Compound P14)

Step 1: Preparation of 1-[5-ethylsulfanyl-6-[4-methyl-5-[4-(trifluoromethyl)-2-pyridyl]-1,2,4-triazol-3-yl]-3-pyridyl]pyrazole-4-carbonitrile (Compound P30)

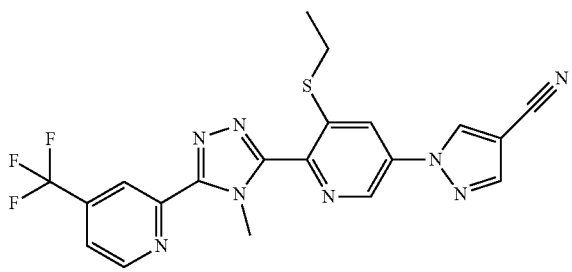 [SMILES: CCSc1cc(-n2cc(C#N)cn2)cnc1-c1nnc(-c2cc(C(F)(F)F)ccn2)n1C]

To a solution of 5-bromo-3-ethylsulfanyl-2-[4-methyl-5-[4-(trifluoromethyl)-2-pyridyl]-1,2,4-triazol-3-yl]pyridine (300 mg, 0.675 mmol) and 1H-pyrazole-4-carbonitrile (69.15 mg, 0.743 mmol) in N,N-dimethylformamide (3.4 ml) under argon was added copper(I) iodide (6.4 mg, 0.034 mmol), N,N'-dimethylethylenediamine (6.0 mg, 7.26 µl, 0.068 mmol) and potassium carbonate (18.66 mg, 0.135 mmol). The mixture was stirred at reflux for 4 hours. Same quantities of N,N'-dimethylethylenediamine, copper(I) iodide and potassium carbonate were added, and stirring continued at 120° C. overnight. After cooling, the reaction mixture was filtered and concentrated in vacuo. The residue was purified over silica by flash column chromatography (0-80% ethyl acetate gradient in cyclohexane) to afford 1-[5-ethylsulfanyl-6-[4-methyl-5-[4-(trifluoromethyl)-2-pyridyl]-1,2,4-triazol-3-yl]-3-pyridyl]pyrazole-4-carbonitrile (compound P30) as a solid (125 mg). LCMS (method 1): 457 (M+H)$^+$, retention time 1.04 min.

Step 2: Preparation of 1-[5-ethylsulfonyl-6-[4-methyl-5-[4-(trifluoromethyl)-2-pyridyl]-1,2,4-triazol-3-yl]-3-pyridyl]pyrazole-4-carbonitrile (Title Compound P14)

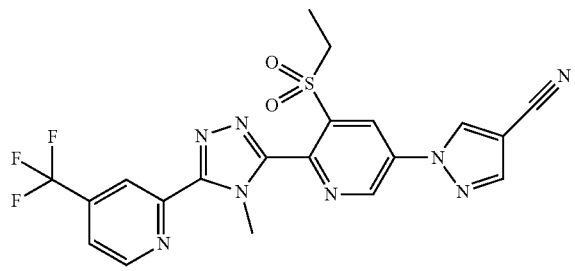 [SMILES: CCS(=O)(=O)c1cc(-n2cc(C#N)cn2)cnc1-c1nnc(-c2cc(C(F)(F)F)ccn2)n1C]

To a solution of 1-[5-ethylsulfanyl-6-[4-methyl-5-[4-(trifluoromethyl)-2-pyridyl]-1,2,4-triazol-3-yl]-3-pyridyl]pyrazole-4-carbonitrile (125 mg, 0.274 mmol) in dichloromethane (5 ml) at 0° C. was added mCPBA (70 wt % in water) (162 mg, 0.657 mmol, 70%) in one portion and the mixture was stirred at room temperature for 2 hours. The reaction mixture was diluted with dichloromethane, washed successively with a 10% aqueous sodium bisulfite solution (3×), a 1M aqueous sodium hydroxide solution and brine, dried over magnesium sulfate and concentrated under reduced pressure. The residue was purified over silica by flash column chromatography (0-20% ethyl acetate gradient in cyclohexane) to afford 1-[5-ethylsulfonyl-6-[4-methyl-5-[4-(trifluoromethyl)-2-pyridyl]-1,2,4-triazol-3-yl]-3-pyridyl]pyrazole-4-carbonitrile (title compound P14) as a solid. LCMS (method 1): 489 (M+H)$^+$, retention time 0.97 min. $^1$H-NMR (CDCl$_3$, ppm) 1.42 (3H), 3.93 (2H), 4.11 (3H), 7.62 (1H), 8.15 (1H), 8.60 (1H), 8.71 (1H), 8.82 (1H), 8.88 (1H), 9.45 (1H).

Example P8

Preparation of 1-[5-ethylsulfonyl-6-[4-methyl-5-[4-(trifluoromethyl)-2-pyridyl]-1,2,4-triazol-3-yl]-3-pyridyl]cyclopropanecarbonitrile (Compound P17)

Step 1: Preparation of 2-[5-ethylsulfonyl-6-[4-methyl-5-[4-(trifluoromethyl)-2-pyridyl]-1,2,4-triazol-3-yl]-3-pyridyl]acetonitrile (Compound Z10)

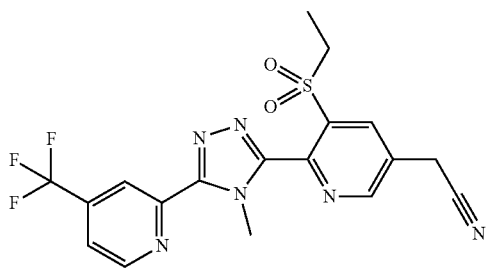 [SMILES: CCS(=O)(=O)c1cc(CC#N)cnc1-c1nnc(-c2cc(C(F)(F)F)ccn2)n1C]

A solution of 5-bromo-3-ethylsulfonyl-2-[4-methyl-5-[4-(trifluoromethyl)-2-pyridyl]-1,2,4-triazol-3-yl]pyridine (500 mg, 1.05 mmol) in DMF (2.1 ml) was placed in a 5 ml microwave vial. Under argon, trimethylsilyl acetonitrile (0.24 g, 0.29 ml, 2.1 mmol), difluorozinc (0.066 g, 0.63 mmol), XANTPHOS (0.025 g, 0.042 mmol) and Pd₂(dba)₃ (0.020 g, 0.021 mmol) were added, the vial was capped, and heated at 140° C. for one hour in the microwave. LC/MS after this time showed reaction completion. The reaction mixture was diluted with ethyl acetate, filtered over diatomaceous earth (Hyflo), the filtrate washed with water and brine. The organic layer was dried over sodium sulfate, filtered and concentrated in vacuo to give the crude product. Purification over a silica gel cartridge (Rf200; 0-75% ethyl acetate gradient in cyclohexane) gave the title compound as a beige solid (240 mg), mp 216-221° C. LCMS (method 1): 437 (M+H)⁺, retention time 0.88 min. ¹H-NMR (CDCl₃, ppm) 1.39 (t, J=7.34 Hz, 3H), 3.86 (q, J=7.34 Hz, 2H), 4.02 (s, 2H), 4.08 (s, 3H), 7.60 (m, 1H), 8.51 (d, J=2.20 Hz, 1H), 8.70 (s, 1H), 8.87 (d, J=5.13 Hz, 1H), 9.03 (d, J=2.20 Hz, 1H).

Similarly, 2-[5-ethylsulfonyl-6-[4-methyl-5-[6-(trifluoromethyl)pyrimidin-4-yl]-1,2,4-triazol-3-yl]-3-pyridyl]acetonitrile (compound Z11, solid, mp 203-204° C.) may be obtained from 4-[5-(5-bromo-3-ethylsulfonyl-2-pyridyl)-4-methyl-1,2,4-triazol-3-yl]-6-(trifluoromethyl)pyrimidine and trimethylsilyl acetonitrile according to the protocol described above. LCMS (method 1): 438 (M+H)⁺, retention time: 0.85 min. ¹H NMR (CDCl₃, ppm) 1.39 (t, J=7.34 Hz, 3H), 3.81 (q, J=7.34 Hz, 2H), 4.03 (s, 2H), 4.12 (s, 3H), 8.51 (d, J=2.20 Hz, 1H), 8.78 (d, J=1.10 Hz, 1H), 9.04 (d, J=2.20 Hz, 1H), 9.47 (m, 1H).

Step 2: Preparation of 1-[5-ethylsulfonyl-6-[4-methyl-5-[4-(trifluoromethyl)-2-pyridyl]-1,2,4-triazol-3-yl]-3-pyridyl]cyclopropanecarbonitrile (Compound P17)

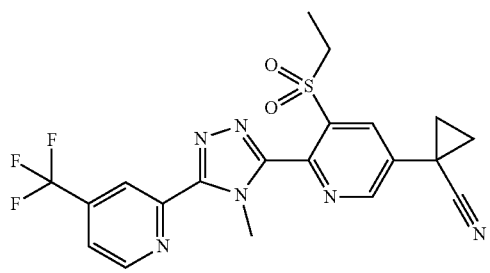 [SMILES: CCS(=O)(=O)c1cc(C2(C#N)CC2)cnc1-c1nnc(-c2cc(C(F)(F)F)ccn2)n1C]

A solution of 2-[5-ethylsulfonyl-6-[4-methyl-5-[4-(trifluoromethyl)-2-pyridyl]-1,2,4-triazol-3-yl]-3-pyridyl]acetonitrile (0.10 g, 0.23 mmol) in acetonitrile (3 ml) was treated with cesium carbonate (0.22 g, 0.69 mmol), and then with 1,2-dibromoethane (0.088 g, 0.04 ml, 0.46 mmol). The brown solution was stirred at 80° C. for 6.5 hours. The reaction mixture was concentrated in vacuo, and the residue was dissolved in ethyl acetate and diluted with water. The organic layer was separated, washed with water and brine, dried over sodium sulfate, filtered and concentrated in vacuo. The crude product was purified over a silica gel cartridge (Rf200; 0-50% ethyl acetate gradient in cyclohexane) to give the title product P17 as an off-white solid (50 mg), mp 197-198° C. LCMS (method 1): 463 (M+H)⁺, retention time 0.94 min. ¹H-NMR (CDCl₃, ppm) 1.37 (t, J=7.34 Hz, 3H), 1.67 (m, 2H), 2.03 (m, 2H), 3.85 (q, J=7.34 Hz, 2H), 4.07 (s, 3H), 7.60 (d, J=5.13 Hz, 1H), 8.24 (d, J=2.20 Hz, 1H), 8.70 (s, 1H), 8.87 (d, J=5.13 Hz, 1H), 9.07 (d, J=2.20 Hz, 1H).

Example P9

Preparation of 3-ethylsulfonyl-2-[4-methyl-5-[4-(trifluoromethyl)-2-pyridyl]-1,2,4-triazol-3-yl]-6-[4-(trifluoromethyl)phenyl]pyridine (Compound P32)

Step A-1: Preparation of methyl 6-chloro-3-ethylsulfanyl-pyridine-2-carboxylate

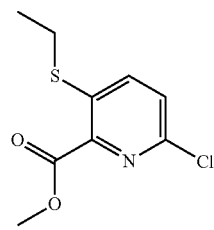

3,6-Dichloro-2-pyridinecarboxylic acid methyl ester (commercially available, 20.0 g, 97.073 mmol) was dissolved in tetrahydrofuran (200 ml) and 18-crown-6-ether (some crystals) was added. Sodium ethanethiolate (9.073 g, 97.073 mmol) was then added in 3 portions at room temperature and the reaction was stirred for 1 hour at room temperature. The reaction mixture was poured on an aqueous saturated ammonium chloride solution (100 ml) and extracted twice with ethyl acetate (2×100 ml). The combined organic layers were washed with an aqueous saturated ammonium chloride solution (2×50 ml) and water (3×100 ml), dried over sodium sulfate, filtered and evaporated under vacuum. The crude was purified by combi flash chromatography (220 g column; gradient cyclohexane+0-10% ethyl acetate) to give the title compound (14.5 g) as a solid, mp 122-124° C. LCMS (method 1): 232/234 (M+H)⁺, retention time 0.94 min. ¹H NMR (400 MHz, CDCl₃) δ ppm: 1.42 (t, 3H), 2.96 (q, 2H), 4.02 (s, 3H), 7.45 (d, 1H), 7.70 (d, 1H).

Step A-2: Preparation of methyl 3-ethylsulfanyl-6-[4-(trifluoromethyl)phenyl]pyridine-2-carboxylate

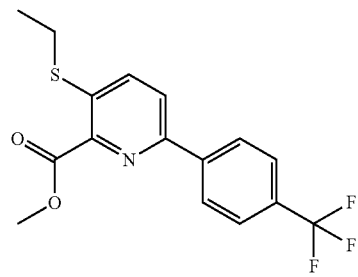 [SMILES: CCSc1ccc(-c2ccc(C(F)(F)F)cc2)nc1C(=O)OC]

A solution of methyl 6-chloro-3-ethylsulfanyl-pyridine-2-carboxylate (0.3 g, 1.29 mmol) in 1,4-dioxane (7.5 ml) was treated with [4-(trifluoromethyl)phenyl]boronic acid (0.32 g, 1.68 mmol) and anhydrous potassium carbonate (0.537 g, 3.88 mmol), and the mixture purged with argon for 10 minutes. To this mixture was added tetrakis(triphenylphosphine)palladium(0) (0.149 g, 0.129 mmol) and the solution heated at 95° C. overnight. The reaction mixture was quenched with water at room temperature and ethyl acetate was added. The aqueous layer was extracted 3 times with ethyl acetate. The combined organic layer was washed with an aqueous saturated NaHCO₃ solution and brine, dried over sodium sulfate, filtered and evaporated under vacuum at 45° C. The crude product was dissolved in dichloromethane and adsorbed on TEFLON BULK SORBENTS. The crude was purified by Combi flash chromatography (24 g column; gradient cyclohexane+0-50% ethyl acetate) to give the title compound (280 mg) as a white solid, mp 67-69° C. LCMS (method 1): 342 (M+H)⁺, retention time 1.21 min. ¹H-NMR (CDCl₃, ppm) 1.41 (t, J=7.34 Hz, 3H), 2.99 (q, J=7.34 Hz, 2H), 4.03 (s, 3H), 7.72 (d, J=8.07 Hz, 2H), 7.80 (m, 2H), 8.13 (d, J=8.07 Hz, 2H).

Step A-3: Preparation of 3-ethylsulfanyl-6-[4-(trifluoromethyl)phenyl]pyridine-2-carbohydrazide

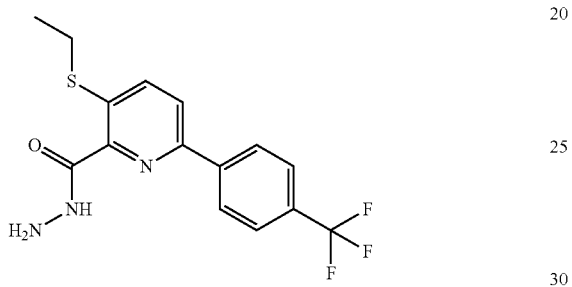

Obtained from methyl 3-ethylsulfanyl-6-[4-(trifluoromethyl)phenyl]pyridine-2-carboxylate (500 mg, 1.44 mmol) and hydrazine hydrate (0.091 ml, 1.87 mmol) in methanol (10 ml) according to procedure Example P1, step A-5. The mixture was stirred at reflux temperature for 11 hours. After cooling, the suspension was diluted with diethyl ether, filtered, the solid washed with cold diethyl ether and dried in vacuo to afford 3-ethylsulfanyl-6-[4-(trifluoromethyl) phenyl]pyridine-2-carbohydrazide (380 mg) as a solid, mp 154-155° C. LCMS (method 1): 342 (M+H)⁺; retention time: 1.02 min. ¹H-NMR (CDCl₃, ppm) 1.45 (t, J=7.34 Hz, 3H), 2.98 (q, J=7.34 Hz, 2H), 4.08 (br s, 2H), 7.74 (d, J=8.11 Hz, 2H), 7.79 (m, 2H), 8.07 (d, J=8.11 Hz, 2H), 9.00 (br s, 1H).

Step B-1: Preparation of 3-ethylsulfanyl-2-[4-methyl-5-[4-(trifluoromethyl)-2-pyridyl]-1,2,4-triazol-3-yl]-6-[4-(trifluoromethyl)phenyl]pyridine (Compound P31)

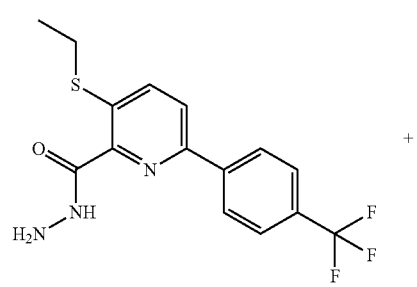

+

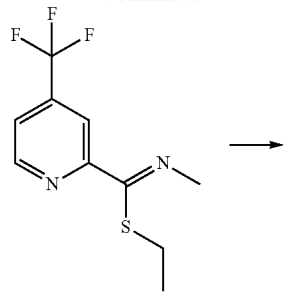

→

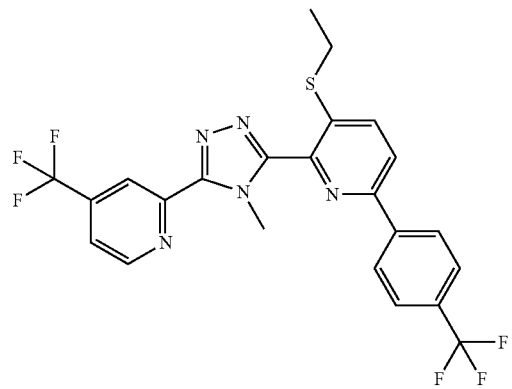

Obtained from 3-ethylsulfanyl-6-[4-(trifluoromethyl)phenyl]pyridine-2-carbohydrazide (371 mg, 1.09 mmol) and ethyl N-methyl-4-(trifluoromethyl)pyridine-2-carboximidothioate (270 mg, 1.09 mmol) in pyridine (2 ml) according to procedure Example P3, step C-1. The mixture was heated in the microwave at 180° C. for 40 minutes. After cooling, the reaction mixture was concentrated in vacuo. Flash chromatography purification (gradient 0-30% ethyl acetate in cyclohexane) afforded 3-ethylsulfanyl-2-[4-methyl-5-[4-(trifluoromethyl)-2-pyridyl]-1,2,4-triazol-3-yl]-6-[4-(trifluoromethyl)phenyl]-pyridine (compound P31) as a solid (260 mg), mp 174-175° C. LCMS (method 1): 510 (M+H)⁺; retention time: 1.25 min. ¹H-NMR (CDCl₃, ppm) 1.37 (t, J=7.34 Hz, 3H), 3.02 (d, J=7.34 Hz, 2H), 4.22 (s, 3H), 7.59 (dd, J=5.10, 1.10 Hz, 1H), 7.73 (d, J=8.07 Hz, 2H), 7.87 (m, 2H), 8.16 (d, J=8.07 Hz, 2H), 8.73 (m, 1H), 8.88 (d, J=5.10 Hz, 1H).

Step B-2: Preparation of 3-ethylsulfonyl-2-[4-methyl-5-[4-(trifluoromethyl)-2-pyridyl]-1,2,4-triazol-3-yl]-6-[4-(trifluoromethyl)phenyl]pyridine (Compound P32)

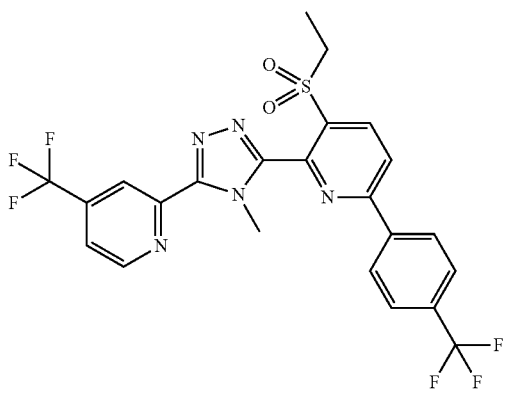 [SMILES: CCS(=O)(=O)c1ccc(-c2ccc(C(F)(F)F)cc2)nc1-c1nnc(-c2cc(C(F)(F)F)ccn2)n1C]

Obtained from 3-ethylsulfanyl-2-[4-methyl-5-[4-(trifluoromethyl)-2-pyridyl]-1,2,4-triazol-3-yl]-6-[4-(trifluoromethyl)phenyl]pyridine (190 mg, 0.373 mmol) and mCPBA (172 mg, 0.750 mmol, 75%) in dichloromethane (10 ml) according to procedure Example P1, step C-2. The mixture was stirred at room temperature overnight. Flash chromatography purification (gradient 0-25% ethyl acetate in cyclohexane) afforded 3-ethylsulfonyl-2-[4-methyl-5-[4-(trifluoromethyl)-2-pyridyl]-1,2,4-triazol-3-yl]-6-[4-(trifluoromethyl)phenyl]pyridine (title compound P32) as a solid (130 mg). LCMS (method 1): 542 (M+H)$^+$; retention time: 1.17 min. $^1$H-NMR (CDCl$_3$, ppm) 1.40 (t, J=7.34 Hz, 3H), 3.85 (q, J=7.34 Hz, 2H), 4.12 (s, 3H), 7.60 (dd, J=5.10, 1.28 Hz, 1H), 7.79 (d, J=8.44 Hz, 2H), 8.13 (d, J=8.44 Hz, 1H), 8.24 (d, J=8.44 Hz, 2H), 8.61 (d, J=8.44 Hz, 1H), 8.73 (m, 1H), 8.88 (d, J=5.10 Hz, 1H).

Example P10

Preparation of 3-ethylsulfonyl-2-[4-methyl-5-[4-(trifluoromethyl)-2-pyridyl]-1,2,4-triazol-3-yl]-5-(trifluoromethylsulfanyl)pyridine (Compound P34)

Step 1: Preparation of 3-ethylsulfanyl-2-[4-methyl-5-[4-(trifluoromethyl)-2-pyridyl]-1,2,4-triazol-3-yl]-5-(trifluoromethylsulfanyl)pyridine (Compound P33)

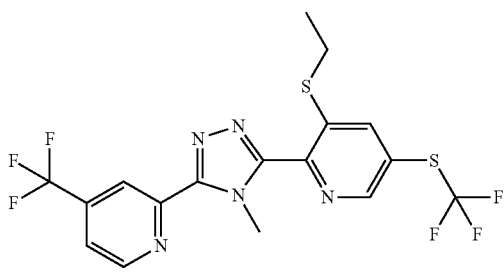 [SMILES: CCSc1cc(SC(F)(F)F)cnc1-c1nnc(-c2cc(C(F)(F)F)ccn2)n1C]

A 20 ml microwave vial was charged with a solution of 5-bromo-3-ethylsulfanyl-2-[4-methyl-5-[4-(trifluoromethyl)-2-pyridyl]-1,2,4-triazol-3-yl]pyridine (1.0 g, 2.251 mmol) and (bpy)CuSCF$_3$ (2.328 g, 7.257 mmol; CAS 1413732-47-4) in acetonitrile (15 ml). The mixture was flushed with argon for 10 minutes, the vial was capped, and heated at 100° C. for 20 hours. After cooling, the reaction mixture was diluted with t-butyl methyl ether and filtered over diatomaceous earth (Hyflo), the filtrate dried over sodium sulfate and concentrated in vacuo. The residue was purified over silica by flash column chromatography (cyclohexane/ethyl acetate, gradient 3:1 to 1:1) to afford 3-ethylsulfanyl-2-[4-methyl-5-[4-(trifluoromethyl)-2-pyridyl]-1,2,4-triazol-3-yl]-5-(trifluoromethylsulfanyl)pyridine (compound P33) as a solid (489 mg), mp 94-95° C. LCMS (method 1): 466 (M+H)$^+$; retention time: 1.17 min. $^1$H-NMR (CDCl$_3$, ppm) 1.37 (t, J=7.34 Hz, 3H), 3.01 (q, J=7.34 Hz, 2H), 4.21 (s, 3H), 7.59 (d, J=5.14 Hz, 1H), 7.99 (m, 1H), 8.67 (m, 1H), 8.71 (s, 1H), 8.88 (d, J=5.14 Hz, 1H).

Step 2: Preparation of 3-ethylsulfonyl-2-[4-methyl-5-[4-(trifluoromethyl)-2-pyridyl]-1,2,4-triazol-3-yl]-5-(trifluoromethylsulfanyl)pyridine (Compound P34)

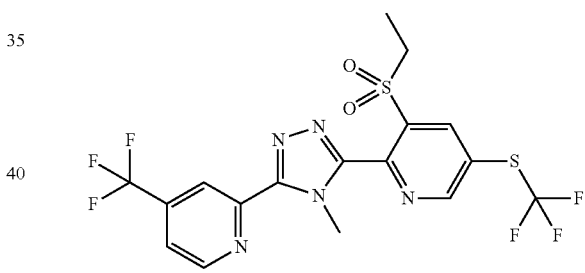

Obtained from 3-ethylsulfanyl-2-[4-methyl-5-[4-(trifluoromethyl)-2-pyridyl]-1,2,4-triazol-3-yl]-5-(trifluoromethylsulfanyl)pyridine (460 mg, 0.988 mmol) and mCPBA (451 mg, 1.987 mmol, 75%) in dichloromethane (5 ml) according to procedure Example P1, step C-2. The mixture was stirred at room temperature overnight. Flash chromatography purification (cyclohexane/ethyl acetate 2:1) afforded 3-ethylsulfonyl-2-[4-methyl-5-[4-(trifluoromethyl)-2-pyridyl]-1,2,4-triazol-3-yl]-5-(trifluoromethylsulfanyl)-pyridine (compound P34) as a solid (420 mg), mp 183-184° C. LCMS (method 1): 498 (M+H)$^+$; retention time: 1.10 min. $^1$H-NMR (CDCl$_3$, ppm) 1.40 (t, J=7.34 Hz, 3H), 3.90 (q, J=7.34 Hz, 2H), 4.12 (s, 3H), 7.61 (d, J=5.14 Hz, 1H), 8.70 (s, 1H), 8.79 (d, J=1.83 Hz, 1H), 8.88 (d, J=5.14 Hz, 1H), 9.18 (d, J=1.83 Hz, 1H).

Example P11

Preparation of 3-ethylsulfonyl-2-[4-methyl-5-[4-(trifluoromethyl)-2-pyridyl]-1,2,4-triazol-3-yl]-5-(trifluoromethylsulfonyl)pyridine (Compound P35) and 3-ethylsulfonyl-2-[4-methyl-5-[4-(trifluoromethyl)-2-pyridyl]-1,2,4-triazol-3-yl]-5-(trifluoromethylsulfinyl)pyridine (Compound P36)

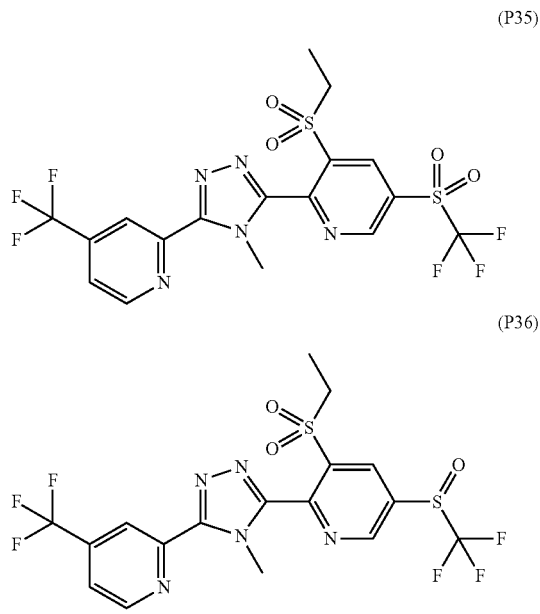

(P35)

(P36)

To a solution of 3-ethylsulfonyl-2-[4-methyl-5-[4-(trifluoromethyl)-2-pyridyl]-1,2,4-triazol-3-yl]-5-(trifluoromethylsulfanyl)pyridine (200 mg, 0.402 mmol) in dichloromethane (5 ml) at 0° C. was added mCPBA (75 wt % in water) (190 mg, 0.824 mmol, 75%) in one portion and the mixture was stirred at 0° C. for 15 minutes, room temperature for 4 hours, then at 30° C. for 24 hours. Another portion of mCPBA (18.5 mg, 0.080 mmol, 75%) was added and stirring continued at 30° C. for 24 hours. The reaction mixture was diluted with dichloromethane, washed successively with a 10% aqueous sodium bisulfite solution (2×), a saturated aqueous sodium bicarbonate solution (4×) and brine, dried over sodium sulfate and concentrated under reduced pressure. The residue was purified over silica by flash column chromatography (cyclohexane/ethyl acetate, gradient 3:1 to 1:1) to afford 3-ethylsulfonyl-2-[4-methyl-5-[4-(trifluoromethyl)-2-pyridyl]-1,2,4-triazol-3-yl]-5-(trifluoromethylsulfonyl)pyridine (compound P35) as a solid (24 mg). LCMS (method 2): 530 (M+H)$^+$; retention time: 1.78 min. $^1$H-NMR (CDCl$_3$, ppm) 1.44 (t, J=7.34 Hz, 3H), 4.03 (q, J=7.34 Hz, 2H), 4.20 (s, 3H), 7.64 (d, J=5.13 Hz, 1H), 8.71 (s, 1H), 8.91 (d, J=5.13 Hz, 1H), 9.11 (d, J=1.91 Hz, 1H), 9.51 (d, J=1.91 Hz, 1H).

Further elution then gave 3-ethylsulfonyl-2-[4-methyl-5-[4-(trifluoromethyl)-2-pyridyl]-1,2,4-triazol-3-yl]-5-(trifluoromethylsulfinyl)pyridine (compound P36) as a solid (18 mg). LCMS (method 2): 514 (M+H)$^+$; retention time: 1.60 min. $^1$H-NMR (CDCl$_3$, ppm) 1.41 (t, J=7.35 Hz, 3H), 3.95 (q, J=7.35 Hz, 2H), 4.15 (s, 3H), 7.63 (d, J=5.14 Hz, 1H), 8.71 (s, 1H), 8.91 (m, 2H), 9.32 (d, J=1.83 Hz, 1H).

Example P12

Preparation of 4-[5-[6-(3-chloro-1,2,4-triazol-1-yl)-3-ethylsulfonyl-2-pyridyl]-4-methyl-1,2,4-triazol-3-yl]-6-(trifluoromethyl)pyrimidine (Compound P48)

Step A-1: Preparation of N-methyl-6-(trifluoromethyl)pyrimidine-4-carboxamide

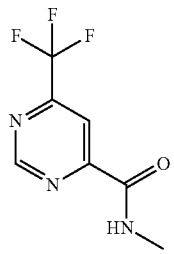

To a solution of 6-(trifluoromethyl)pyrimidine-4-carboxylic acid (24.2 g, 126.0 mmol) in dichloromethane (300 ml) at 5-10° C. was added dropwise N,N-dimethylformamide (0.1 ml) and oxalyl chloride (13.6 ml, 151.2 mmol). The reaction mixture was stirred at ambient temperature overnight, then concentrated to dryness in vacuo to afford 6-(trifluoromethyl)pyrimidine-4-carbonyl chloride (25.3 g) as a solid.

The title compound N-methyl-6-(trifluoromethyl)pyrimidine-4-carboxamide was obtained from 6-(tri-fluoromethyl)pyrimidine-4-carbonyl chloride (24 g, 114.0 mmol), methylamine (2M in tetrahydrofuran) (142.5 ml, 285.0 mmol) and triethylamine (171.0 mmol) in tetrahydrofuran (total 300 ml) according to procedure Example P3, step A-1. The mixture was stirred at 0-5° C. for one hour. The crude material obtained after aqueous workup was used without further purification (19.9 g as a solid). LCMS (method 1): 206 (M+H)$^+$; retention time: 0.70 min. $^1$H-NMR (CDCl$_3$, ppm) 3.10 (d, 3H), 7.97 (br s, 1H), 8.48 (s, 1H), 9.39 (s, 1H).

Step A-2: Preparation of N-methyl-6-(trifluoromethyl)pyrimidine-4-carbothioamide

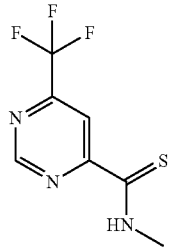

Obtained from N-methyl-6-(trifluoromethyl)pyrimidine-4-carboxamide (19.0 g, 92.6 mmol) and phosphorus pentasulfide (24.7 g, 55.6 mmol) in pyridine (200 ml) according to procedure Example P3, step A-2. The mixture was stirred at reflux temperature for 4.5 hours. The crude material obtained after aqueous workup was used without further purification (16.1 g as a solid), mp 104-106° C. LCMS (method 1): 222 (M+H)⁺; retention time: 0.95 min. ¹H-NMR (CDCl₃, ppm) 3.43 (d, 3H), 8.92 (s, 1H), 9.33 (s, 1H), 10.06 (br s, 1H).

Step A-3: Preparation of ethyl N-methyl-6-(trifluoromethyl)pyrimidine-4-carboximidothioate

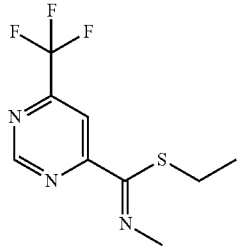 [SMILES: CCS/C(=N\C)c1cc(C(F)(F)F)ncn1]

Obtained from N-methyl-6-(trifluoromethyl)pyrimidine-4-carbothioamide (15.0 g, 67.8 mmol), sodium ethoxide (21 wt % in EtOH) (67.8 mmol, 25 ml) and iodoethane (21.15 g, 135.6 mmol, 11.6 ml) in ethanol (350 ml) according to procedure Example P3, step A-3. The mixture was stirred at room temperature overnight. The crude material obtained after aqueous workup was used without further purification (11.8 g as a liquid). LCMS (method 1): 250 (M+H)⁺; retention time: 0.96 min. ¹H-NMR (CDCl₃, ppm) 1.19 (t, 3H), 2.97 (q, 2H), 3.56 (s, 3H), 8.04 (s, 1H), 9.42 (s, 1H).

Step B-1: Preparation of 6-chloro-3-ethylsulfanyl-pyridine-2-carbohydrazide

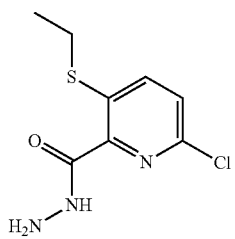

Obtained from methyl 6-chloro-3-ethylsulfanyl-pyridine-2-carboxylate (preparation described above, 10.0 g, 43.16 mmol) and hydrazine monohydrate (4.24 ml, 86.3 mmol) in methanol (100 ml) according to procedure Example P3, step B-4. The mixture was stirred at reflux for 26 hours. The residue obtained after workup was triturated in diethyl ether, filtered and dried in vacuo to afford 6-chloro-3-ethylsulfanyl-pyridine-2-carbohydrazide (6.12 g) as a solid, mp 150-151° C. LCMS (method 1): 232/234 (M+H)⁺; retention time: 0.64 min. ¹H-NMR (CDCl₃, ppm) 1.41 (t, 3H), 2.92 (q, 2H), 4.02 (d, 2H), 7.36 (d, 1H), 7.62 (d, 1H), 8.76 (br s, 1H).

Step C-1: Preparation of 4-[5-(6-chloro-3-ethylsulfanyl-2-pyridyl)-4-methyl-1,2,4-triazol-3-yl]-6-(trifluoromethyl)pyrimidine

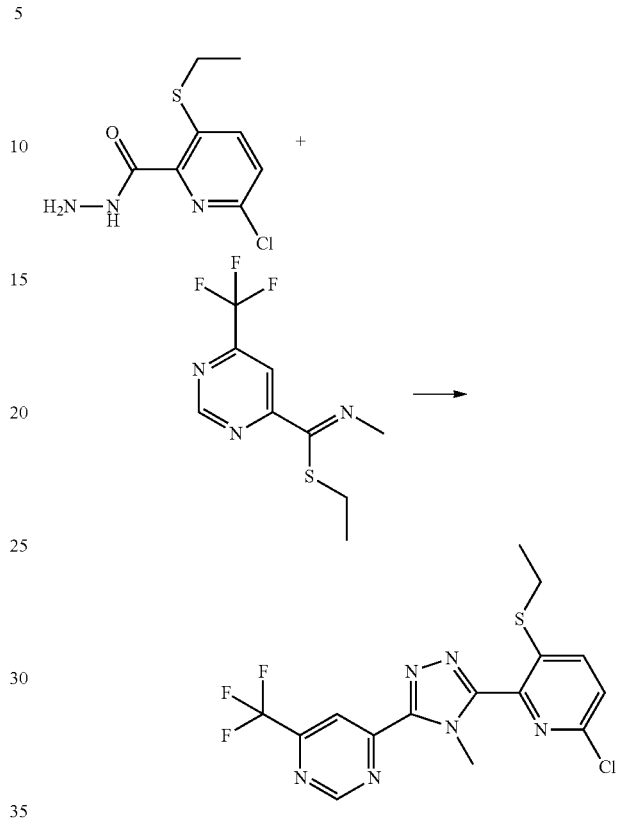

Obtained from 6-chloro-3-ethylsulfanyl-pyridine-2-carbohydrazide (4.65 g, 20.07 mmol) and ethyl N-methyl-6-(trifluoromethyl)pyrimidine-4-carboximidothioate (5.0 g, 20.06 mmol) in pyridine (50 ml) according to procedure Example P3, step C-1. The mixture was heated in the microwave at 160° C. for 60 minutes (four parallel reactions). The crude material obtained after combined workup was used without further purification (8.04 g as a solid), mp 88-90° C. LCMS (method 1): 401/403 (M+H)⁺; retention time: 1.01 min. ¹H-NMR (CDCl₃, ppm) 1.33 (t, 3H), 2.97 (q, 2H), 4.25 (s, 3H), 7.43 (d, 1H), 7.77 (d, 1H), 8.79 (s, 1H), 9.46 (s, 1H).

Step C-2: Preparation of 4-[5-(6-chloro-3-ethylsulfonyl-2-pyridyl)-4-methyl-1,2,4-triazol-3-yl]-6-(trifluoromethyl)pyrimidine

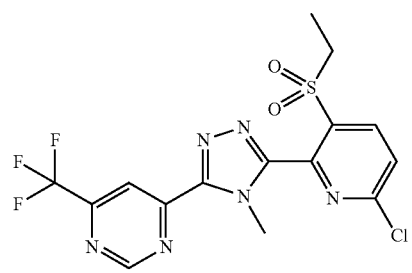 [SMILES: CCS(=O)(=O)c1ccc(Cl)nc1-c1nnc(-c2cc(C(F)(F)F)ncn2)n1C]

Obtained from 4-[5-(6-chloro-3-ethylsulfanyl-2-pyridyl)-4-methyl-1,2,4-triazol-3-yl]-6-(trifluoromethyl) pyrimidine (2.5 g, 6.24 mmol) and mCPBA (3.2 g, 13.0 mmol, 70%) in dichloromethane (30 ml) according to procedure Example P3, step C-2. The mixture was stirred at 0-5° C. for 3 hours. The residue obtained after aqueous workup was triturated with diethyl ether, the suspension filtered and the solid dried in vacuo to afford 4-[5-(6-chloro-3-ethylsulfonyl-2-pyridyl)-4-methyl-1,2,4-triazol-3-yl]-6-(trifluoromethyl)pyrimidine (2.2 g) as a solid, mp 183-185° C. LCMS (method 1): 433/435 (M+H)$^+$; retention time: 0.94 min. $^1$H-NMR (CDCl$_3$, ppm) 1.37 (t, 3H), 3.76 (q, 2H), 4.15 (s, 3H), 7.74 (d, 1H), 8.47 (d, 1H), 8.77 (s, 1H), 9.47 (s, 1H).

Step C-3: Preparation of 4-[5-[6-(3-chloro-1,2,4-triazol-1-yl)-3-ethylsulfonyl-2-pyridyl]-4-methyl-1,2,4-triazol-3-yl]-6-(trifluoromethyl)pyrimidine (Compound P48)

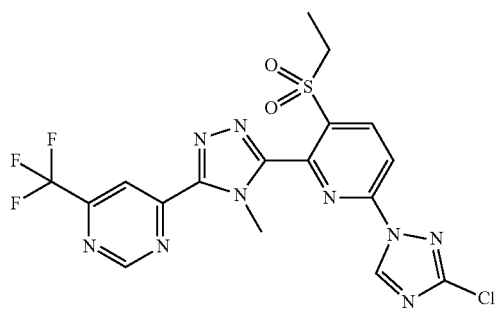 [SMILES: CCS(=O)(=O)c1ccc(-n2cnc(Cl)n2)nc1-c1nnc(-c2cc(C(F)(F)F)ncn2)n1C]

A solution of 4-[5-(6-chloro-3-ethylsulfonyl-2-pyridyl)-4-methyl-1,2,4-triazol-3-yl]-6-(trifluoromethyl) pyrimidine (300 mg, 0.693 mmol) and 3-chloro-1H-1,2,4-triazole (107.6 mg, 1.04 mmol) in pyridine (3 ml) under argon was heated in the microwave at 120° C. for 30 minutes. After cooling, the reaction mixture was poured onto iced water (20 ml), the suspension filtered and the solid washed with cold water. This residue was dissolved in dichloromethane, dried over sodium sulfate, filtered and concentrated to dryness to afford the title compound 4-[5-[6-(3-chloro-1,2,4-triazol-1-yl)-3-ethylsulfonyl-2-pyridyl]-4-methyl-1,2,4-triazol-3-yl]-6-(trifluoromethyl)pyrimidine (compound P48) as a solid, mp 261-263° C. LCMS (method 1): 500/502 (M+H)$^+$; retention time: 0.96 min. $^1$H-NMR (CDCl$_3$, ppm) 1.38 (t, 3H), 3.72 (q, 2H), 4.14 (s, 3H), 8.25 (d, 1H), 8.73 (d, 1H), 8.79 (s, 1H), 9.07 (s, 1H), 9.48 (s, 1H).

Example P13

Preparation of 3-ethylsulfonyl-6-(3-fluorophenyl)-2-[4-methyl-5-[4-(trifluoromethyl)-2-pyridyl]-1,2,4-triazol-3-yl]pyridine (Compound P50)

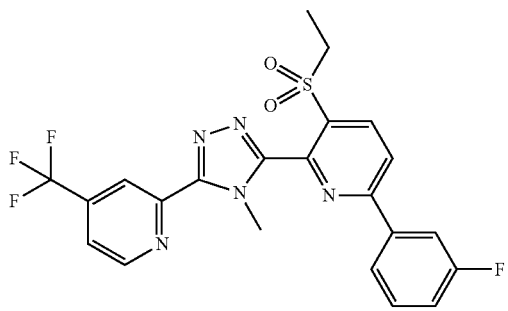 [SMILES: CCS(=O)(=O)c1ccc(-c2cccc(F)c2)nc1-c1nnc(-c2cc(C(F)(F)F)ccn2)n1C]

In a microwave vial, a mixture of 6-chloro-3-ethylsulfonyl-2-[4-methyl-5-[4-(trifluoromethyl)-2-pyridyl]-1,2,4-triazol-3-yl]pyridine (300 mg, 0.695 mmol), (3-fluorophenyl)boronic acid (150 mg, 1.042 mmol) and an aqueous 2M sodium carbonate solution (1.04 ml, 2.0M, 2.08 mmol) in 1,2-dimethoxyethane (3 ml) was purged with argon for 10 minutes. Bis(triphenylphosphine) palladium(II) dichloride (5 mg, 0.007 mmol) was then added, and the mixture was stirred in the microwave at 110° C. for 30 minutes. The reaction mixture was diluted with ethyl acetate, the organic phase washed several times with water and brine, dried over sodium sulfate and concentrated under reduced pressure. The residue was purified over silica by flash column chromatography (ethyl acetate gradient in cyclohexane) and the fractions containing product were combined and concentrated. The residue was triturated with diethyl ether, the suspension filtered and the solid dried in vacuo to afford 3-ethylsulfonyl-6-(3-fluorophenyl)-2-[4-methyl-5-[4-(trifluoromethyl)-2-pyridyl]-1,2,4-triazol-3-yl]pyridine (compound P50) as a solid (85 mg), mp 182-184° C. LCMS (method 1): 492 (M+H)$^+$, retention time 1.07 min. 1H-NMR (CDCl3, ppm) 1.40 (t, 3H), 3.86 (q, 2H), 4.11 (s, 3H), 7.24 (m, 1H), 7.43 (m, 1H), 7.49-7.62 (m, 3H), 8.67 (d, 1H), 8.71 (s, 1H), 8.88 (d, 1H), 9.19 (d, 1H).

TABLE P

| | Examples of compounds of formula (I) | | | | |
|---|---|---|---|---|---|
| | | | LCMS | | |
| Compound No. | Structures | R$_t$ (min) | [M + H]$^+$ (measured) | Method | Mp (° C.) |
| P1 | 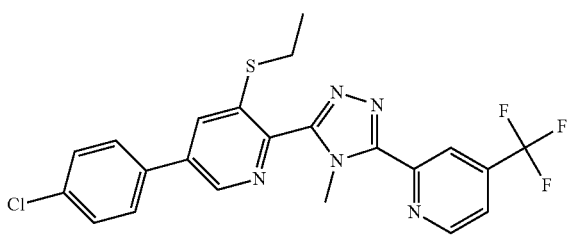 [SMILES: CCSc1cc(-c2ccc(Cl)cc2)cnc1-c1nnc(-c2cc(C(F)(F)F)ccn2)n1C] | 1.97 | 476/478 | 2 | 147-149 |

TABLE P-continued

Examples of compounds of formula (I)

| Compound No. | Structures | LCMS R_t (min) | [M + H]+ (measured) | Method | Mp (° C.) |
|---|---|---|---|---|---|
| P2 | 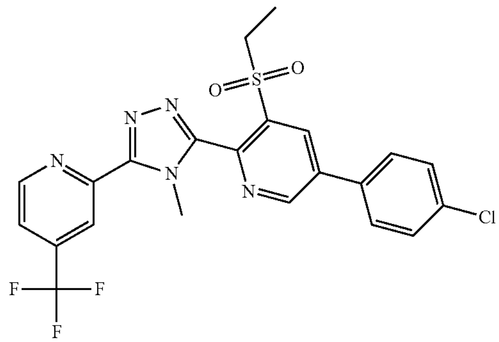 [SMILES: CCS(=O)(=O)c1cc(-c2ccc(Cl)cc2)cnc1-c1nnc(-c2cc(C(F)(F)F)ccn2)n1C] | 1.81 | 508/510 | 2 | 234-235 |
| P3 | 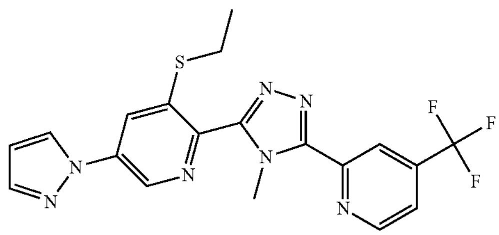 [SMILES: CCSc1cc(-n2cccn2)cnc1-c1nnc(-c2cc(C(F)(F)F)ccn2)n1C] | 1.54 | 432 | 2 | 121-123 |
| P4 | 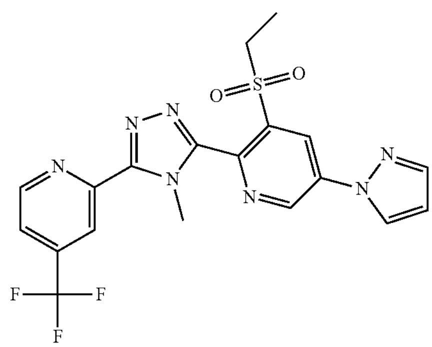 [SMILES: CCS(=O)(=O)c1cc(-n2cccn2)cnc1-c1nnc(-c2cc(C(F)(F)F)ccn2)n1C] | 1.43 | 464 | 2 | 174-176 |
| P5 | 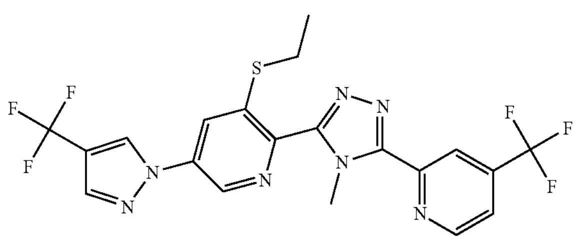 [SMILES: CCSc1cc(-n2cc(C(F)(F)F)cn2)cnc1-c1nnc(-c2cc(C(F)(F)F)ccn2)n1C] | 1.84 | 500 | 2 | |
| P6 | 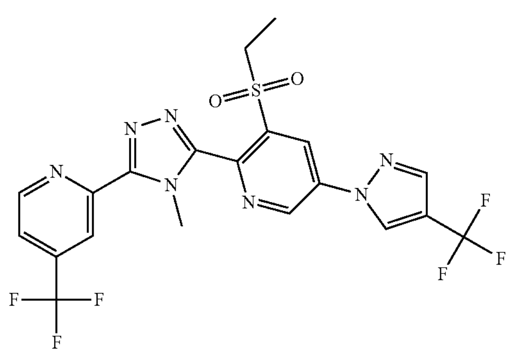 [SMILES: CCS(=O)(=O)c1cc(-n2cc(C(F)(F)F)cn2)cnc1-c1nnc(-c2cc(C(F)(F)F)ccn2)n1C] | 1.71 | 532 | 2 | 172-174 |

TABLE P-continued

Examples of compounds of formula (I)

| Compound No. | Structures | LCMS R_t (min) | [M + H]+ (measured) | Method | Mp (° C.) |
|---|---|---|---|---|---|
| P7 | | 1.59 | 498/500 | 2 | 166-168 |
| P8 | | 1.54 | 444 | 2 | 162-165 |
| P9 | | 1.38 | 476 | 2 | 191-193 |
| P10 | | 2.06 | 510 | 2 | |
| P11 | | 1.16 | 542 | 1 | 206-208 |

TABLE P-continued

Examples of compounds of formula (I)

| Compound No. | Structures | LCMS R_t (min) | [M + H]+ (measured) | Method | Mp (° C.) |
|---|---|---|---|---|---|
| P12 | 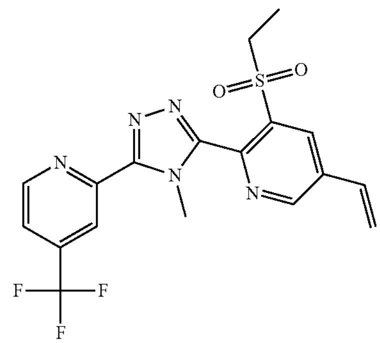 [SMILES: C=Cc1cnc(-c2nnc(-c3cc(C(F)(F)F)ccn3)n2C)c(S(=O)(=O)CC)c1] | 0.97 | 424 | 1 | 67-70 |
| P13 | 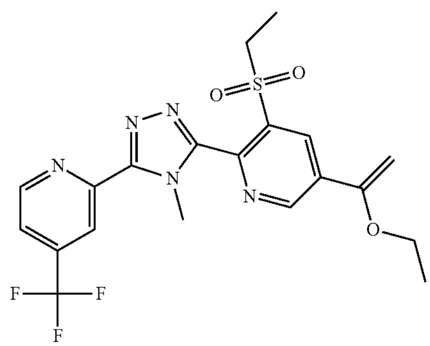 [SMILES: C=C(OCC)c1cnc(-c2nnc(-c3cc(C(F)(F)F)ccn3)n2C)c(S(=O)(=O)CC)c1] | 1.09 | 468 | 1 | |
| P14 | 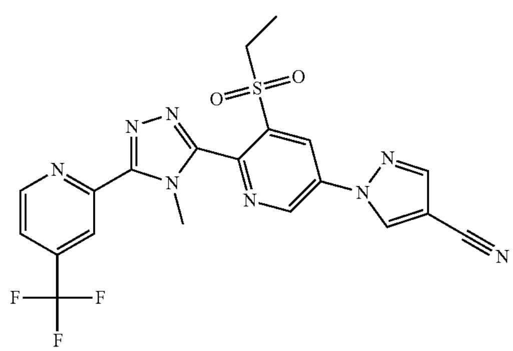 [SMILES: CCS(=O)(=O)c1cc(-n2cc(C#N)cn2)cnc1-c1nnc(-c2cc(C(F)(F)F)ccn2)n1C] | 0.97 | 489 | 1 | |
| P15 | 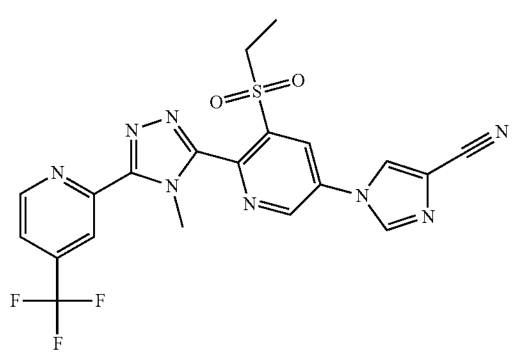 [SMILES: CCS(=O)(=O)c1cc(-n2cnc(C#N)c2)cnc1-c1nnc(-c2cc(C(F)(F)F)ccn2)n1C] | 0.90 | 489 | 1 | |

TABLE P-continued

Examples of compounds of formula (I)

| Compound No. | Structures | LCMS R_t (min) | [M + H]+ (measured) | Method | Mp (° C.) |
|---|---|---|---|---|---|
| P16 | 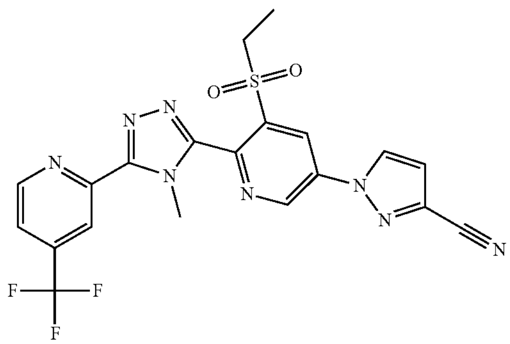 [SMILES: CCS(=O)(=O)c1cc(-n2ccc(C#N)n2)cnc1-c1nnc(-c2cc(C(F)(F)F)ccn2)n1C] | 1.02 | 489 | 1 | |
| P17 | 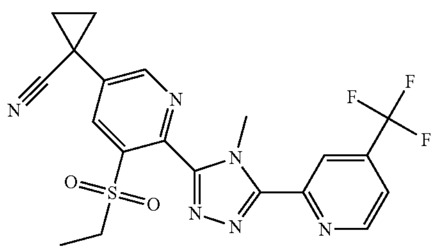 [SMILES: CCS(=O)(=O)c1cc(C2(C#N)CC2)cnc1-c1nnc(-c2cc(C(F)(F)F)ccn2)n1C] | 0.94 | 464 | 1 | 197-198 |
| P18 | 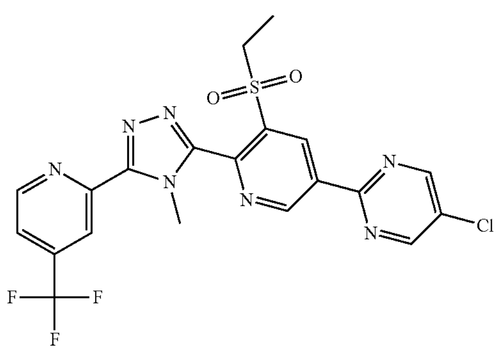 [SMILES: CCS(=O)(=O)c1cc(-c2ncc(Cl)cn2)cnc1-c1nnc(-c2cc(C(F)(F)F)ccn2)n1C] | 1.10 | 510/512 | 1 | 273-275 |
| P19 | 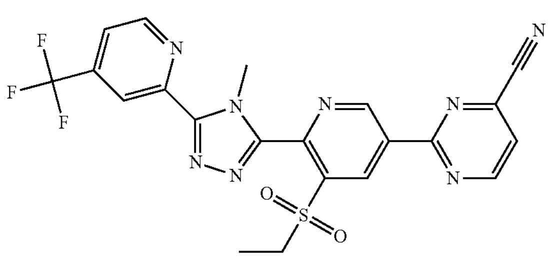 [SMILES: CCS(=O)(=O)c1cc(-c2nccc(C#N)n2)cnc1-c1nnc(-c2cc(C(F)(F)F)ccn2)n1C] | 1.03 | 501 | 1 | 268-270 |

TABLE P-continued

Examples of compounds of formula (I)

| Compound No. | Structures | LCMS R$_t$ (min) | [M + H]$^+$ (measured) | Method | Mp (° C.) |
|---|---|---|---|---|---|
| P20 | | 1.02 | 501 | 1 | 270-272 |
| P21 | | 1.04 | 500 | 1 | 158-160 |
| P22 | | 1.03 | 500 | 1 | 223-225 |
| P23 | | 0.99 | 500 | 1 | 179-181 |
| P24 | | 1.10 | 509/511 | 1 | 172-174 |

TABLE P-continued

Examples of compounds of formula (I)

| Compound No. | Structures | LCMS R$_t$ (min) | [M + H]$^+$ (measured) | Method | Mp (° C.) |
|---|---|---|---|---|---|
| P25 | | 1.11 | 509/511 | 1 | 229-231 |
| P26 | | 1.09 | 509/511 | 1 | 145-147 |
| P27 | | 0.97 | 499/501 | 1 | |
| P28 | | 1.04 | 498/500 | 1 | |

TABLE P-continued

Examples of compounds of formula (I)

| Compound No. | Structures | LCMS R$_t$ (min) | [M + H]$^+$ (measured) | Method | Mp (° C.) |
|---|---|---|---|---|---|
| P29 | | 1.53 | 438 | 2 | solid |
| P30 | | 1.04 | 457 | 1 | solid |
| P31 | | 1.25 | 510 | 1 | 174-175 |
| P32 | | 1.17 | 542 | 1 | solid |
| P33 | | 1.17 | 466 | 1 | 94-95 |
| P34 | | 1.10 | 498 | 1 | 183-184 |

TABLE P-continued

Examples of compounds of formula (I)

| Compound No. | Structures | LCMS R_t (min) | [M + H]+ (measured) | Method | Mp (° C.) |
|---|---|---|---|---|---|
| P35 | 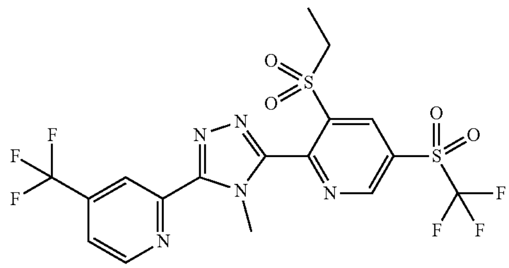 [SMILES: CCS(=O)(=O)c1cc(S(=O)(=O)C(F)(F)F)cnc1-c1nnc(-c2cc(C(F)(F)F)ccn2)n1C] | 1.78 | 530 | 2 | solid |
| P36 | 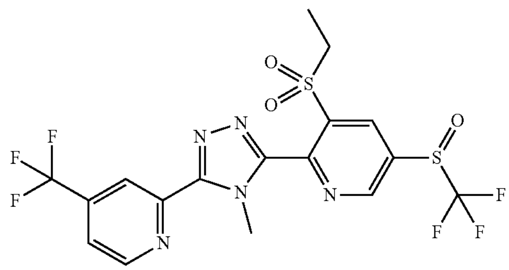 [SMILES: CCS(=O)(=O)c1cc(S(=O)C(F)(F)F)cnc1-c1nnc(-c2cc(C(F)(F)F)ccn2)n1C] | 1.60 | 514 | 2 | solid |
| P37 | 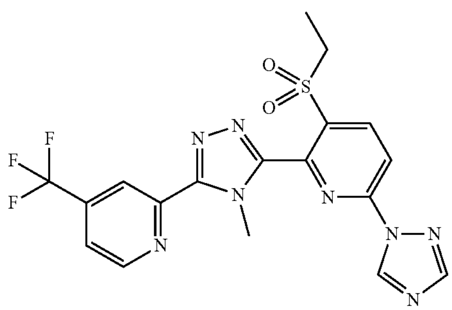 [SMILES: CCS(=O)(=O)c1ccc(-n2cncn2)nc1-c1nnc(-c2cc(C(F)(F)F)ccn2)n1C] | 0.89 | 465 | 1 | 133-135 |
| P38 | 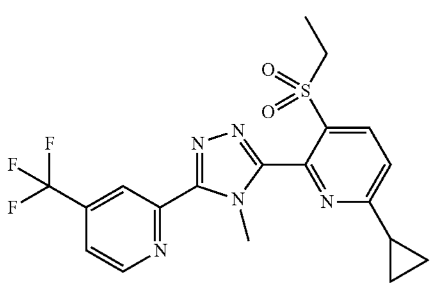 [SMILES: CCS(=O)(=O)c1ccc(C2CC2)nc1-c1nnc(-c2cc(C(F)(F)F)ccn2)n1C] | 1.01 | 438 | 1 | 179-181 |
| P39 | 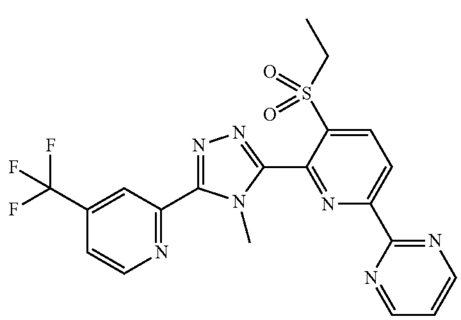 [SMILES: CCS(=O)(=O)c1ccc(-c2ncccn2)nc1-c1nnc(-c2cc(C(F)(F)F)ccn2)n1C] | 0.89 | 476 | 1 | 145-147 |
| P40 | | 0.85 | 465 | 1 | 207-209 |
| P41 | | 0.97 | 499/501 | 1 | 136-138 |

TABLE P-continued

Examples of compounds of formula (I)

| Compound No. | Structures | LCMS R$_t$ (min) | [M + H]$^+$ (measured) | Method | Mp (° C.) |
|---|---|---|---|---|---|
| P42 | | 0.96 | 490 | 1 | 229-231 |
| P43 | | 0.94 | 490 | 1 | 235-237 |
| P44 | | 0.94 | 491 | 1 | 205-207 |
| P45 | | 0.94 | 500/502 | 1 | 233-235 |
| P46 | | 0.84 | 466 | 1 | solid |
| P47 | | 0.85 | 466 | 1 | 245-247 |
| P48 | | 0.96 | 500/502 | 1 | 261-263 |

TABLE P-continued

Examples of compounds of formula (I)

| Compound No. | Structures | LCMS $R_t$ (min) | [M + H]+ (measured) | Method | Mp (° C.) |
|---|---|---|---|---|---|
| P49 | 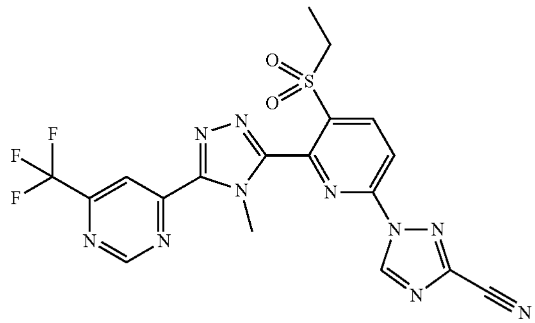 [SMILES: CCS(=O)(=O)c1ccc(-n2cnc(C#N)n2)nc1-c1nnc(-c2cc(C(F)(F)F)ncn2)n1C] | 0.95 | 491 | 1 | 242-244 |
| P50 | 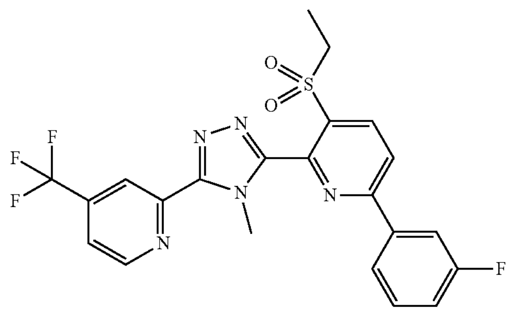 [SMILES: CCS(=O)(=O)c1ccc(-c2cccc(F)c2)nc1-c1nnc(-c2cc(C(F)(F)F)ccn2)n1C] | 1.07 | 492 | 1 | 182-184 |
| P51 | 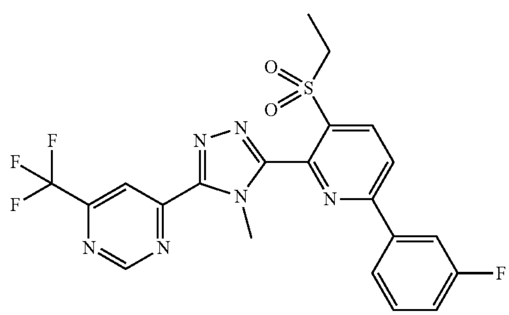 [SMILES: CCS(=O)(=O)c1ccc(-c2cccc(F)c2)nc1-c1nnc(-c2cc(C(F)(F)F)ncn2)n1C] | 1.06 | 493 | 1 | 201-203 |
| P52 | 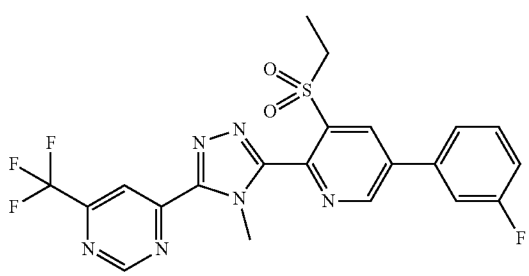 [SMILES: CCS(=O)(=O)c1cc(-c2cccc(F)c2)cnc1-c1nnc(-c2cc(C(F)(F)F)ncn2)n1C] | 1.04 | 493 | 1 | 197-199 |
| P53 | 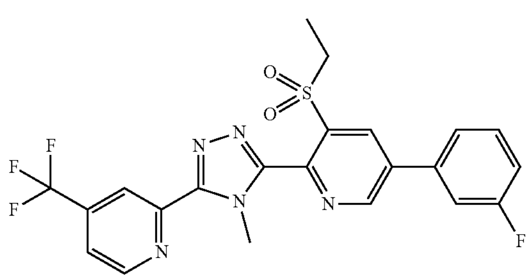 [SMILES: CCS(=O)(=O)c1cc(-c2cccc(F)c2)cnc1-c1nnc(-c2cc(C(F)(F)F)ccn2)n1C] | 1.07 | 492 | 1 | 167-169 |

TABLE P-continued
Examples of compounds of formula (I)
| Compound No. | Structures | LCMS R$_t$ (min) | [M + H]$^+$ (measured) | Method | Mp (° C.) |
|---|---|---|---|---|---|
| P54 | 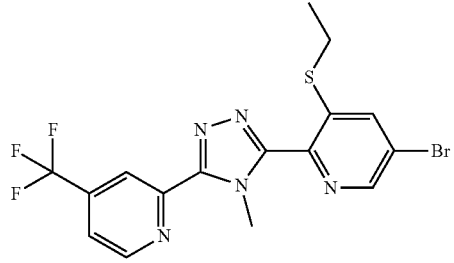 [SMILES: CCSc1cc(Br)cnc1-c1nnc(-c2cc(C(F)(F)F)ccn2)n1C] | 0.84 | 477 | 1 | solid |
| P55 | | 0.98 | 464 | 1 | solid |
| P56 | | 1.07 | 498/500 | 1 | 251-253 |
| P57 | | 0.91 | 464 | 1 | 226-228 |
| P58 | | 0.96 | 439 | 1 | 129-131 |
| P59 | | 0.94 | 477 | 1 | solid |
TABLE Z
Examples of intermediates of formula (IX), (IX-p), (XVII) and (Iab)
| Compound No. | Structures | LCMS R$_t$ (min) | [M + H]$^+$ (measured) | Method | Mp (° C.) |
|---|---|---|---|---|---|
| Z1 | 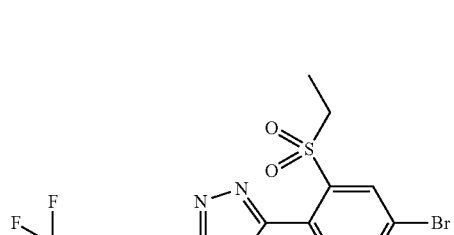 | 1.04 | 444/446 | 1 | 122-123 |
| Z2 | | 1.03 | 476/478 | 1 | 173-175 |

TABLE Z-continued

Examples of intermediates of formula (IX), (IX-p), (XVII) and (Iab)

| Compound No. | Structures | LCMS R_t (min) | [M + H]+ (measured) | Method | Mp (° C.) |
|---|---|---|---|---|---|
| Z3 | | 1.03 | 445/447 | 1 | 108-110 |
| Z4 | | 0.96 | 477/479 | 1 | solid |
| Z5 | | | | | solid |
| Z6 | | | | | 150-152 |
| Z7 | | 1.01 | 401/403 | 1 | 88-90 |

TABLE Z-continued

Examples of intermediates of formula (IX), (IX-p), (XVII) and (Iab)

| Compound No. | Structures | LCMS $R_t$ (min) | [M + H]$^+$ (measured) | Method | Mp (° C.) |
|---|---|---|---|---|---|
| Z8 | 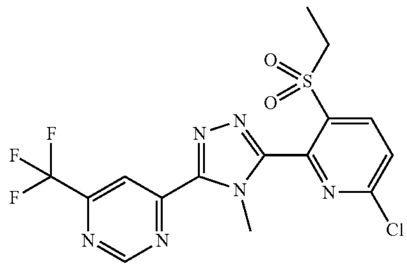 [SMILES: CCS(=O)(=O)c1ccc(Cl)nc1-c1nnc(-c2cc(C(F)(F)F)ncn2)n1C] | 0.94 | 433/435 | 1 | 183-185 |
| Z9 | Measured [M + H]$^+$ consistent with the corresponding boronic acid of formula $C_{16}H_{15}BF_3N_5O_4S$, MW: 441.19. | 0.83 | 442 | 1 | 234-236 |
| Z10 | 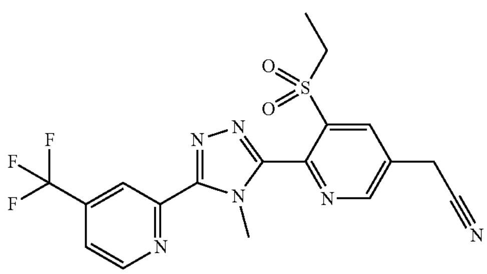 [SMILES: CCS(=O)(=O)c1cc(CC#N)cnc1-c1nnc(-c2cc(C(F)(F)F)ccn2)n1C] | 0.88 | 437 | 1 | 216-221 |
| Z11 | 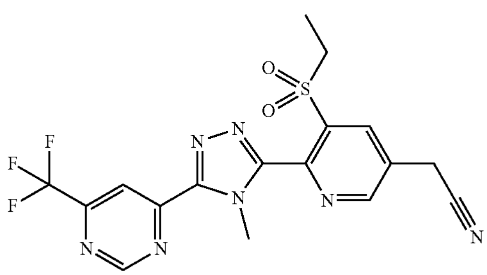 [SMILES: CCS(=O)(=O)c1cc(CC#N)cnc1-c1nnc(-c2cc(C(F)(F)F)ncn2)n1C] | 0.85 | 438 | 1 | 203-204 |

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use. Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX"

means "one compound selected from the group consisting of the compounds described in Tables 1 to 12 and Table P of the present invention"):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, bromofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy) ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxy-aminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+

TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, fluxametamide (WO 2007/026965)+TX, epsilon-metofluthrin [240494-71-7]+TX, epsilon-momfluorothrin [1065124-65-3]+TX, fluazaindolizine [1254304-22-7]+TX, chloroprallethrin [399572-87-3]+TX, fluxametamide [928783-29-3]+TX, cyhalodiamide [1262605-53-7]+TX, tioxazafen [330459-31-9]+TX, broflanilide [1207727-04-5]+TX, flufiprole [704886-18-0]+TX, cyclaniliprole [1031756-98-5]+TX, tetraniliprole [1229654-66-3]+TX, guadipyr (described in WO2010/060231)+TX, cycloxaprid (described in WO2005/077934)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, biterta-nol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzo-lar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-

60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho[2,1-b]pyrano[3,4-e]pyran-4-yl] methyl-cyclopropanecarboxylate [915972-17-7]+TX,1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide [926914-55-8]+TX; lancotrione [1486617-21-3], florpyrauxifen [943832-81-3], ipfentrifluconazole[1417782-08-1], mefentrifluconazole [1417782-03-6], quinofumelin [861647-84-9], chloroprallethrin [399572-87-3], cyhalodiamide [1262605-53-7], fluazaindolizine [1254304-22-7], fluxametamide [928783-29-3], epsilon-metofluthrin [240494-71-7], epsilon-momfluorothrin [1065124-65-3], pydiflumetofen [1228284-64-7], kappa-bifenthrin [439680-76-9], broflanilide [1207727-04-5], dicloromezotiaz [1263629-39-5], dipymetitrone [16114-35-5], pyraziflumid [942515-63-1] and kappa-tefluthrin [391634-71-2]; and microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, Adoxophyes orana granulovirus (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain I-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (Agree®)+TX, *Bacillus thuringiensis israelensis* (BMP123®)+TX, Aquabac®+TX, VectoBac®)+TX, *Bacillus thuringiensis* kurstaki (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD#32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer Beauveria®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis* tenebrionis (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guiffiermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo-miniatus*+TX, *Cryptococcus laurentii*+TX, *Cryptophlebia leucotreta* granulovirus (Cryptex®)+TX, *Cupriavidus campinensis*+TX, *Cydia pomonella* granulovirus (CYD-X®)+TX, *Cydia pomonella* granulovirus (Madex®+TX, Madex Plus®+TX, Madex Max/Carpovirusine®)+TX, *Cylindrobasidium laeve*

(Stumpout®)+TX, Cylindrocladium+TX, Debaryomyces hansenii+TX, Drechslera hawaiinensis+TX, Enterobacter cloacae+TX, Enterobacteriaceae+TX, Entomophtora virulenta (Vektor®)+TX, Epicoccum nigrum+TX, Epicoccum purpurascens+TX, Epicoccum spp.+TX, Filobasidium floriforme+TX, Fusarium acuminatum+TX, Fusarium chlamydosporum+TX, Fusarium oxysporum (Fusaclean®/Biofox C®)+TX, Fusarium proliferatum+TX, Fusarium spp.+TX, Galactomyces geotrichum+TX, Gliocladium catenulatum (Primastop®+TX, Prestop®)+TX, Gliocladium roseum+TX, Gliocladium spp. (SoilGard®)+TX, Gliocladium virens (Soilgard®)+TX, Granulovirus (Granupom®)+TX, Halobacillus halophilus+TX, Halobacillus litoralis+TX, Halobacillus trueperi+TX, Halomonas spp.+TX, Halomonas subglaciescola+TX, Halovibrio variabilis+TX, Hanseniaspora uvarum+TX, Helicoverpa armigera nucleopolyhedrovirus (Helicovex®)+TX, Helicoverpa zea nuclear polyhedrosis virus (Gemstar®)+TX, Isoflavone—formononetin (Myconate®)+TX, Kloeckera apiculata+TX, Kloeckera spp.+TX, Lagenidium giganteum (Laginex®)+TX, Lecanicillium longisporum (Vertiblast®)+TX, Lecanicillium muscarium (Vertikil®)+TX, Lymantria Dispar nucleopolyhedrosis virus (Disparvirus®)+TX, Marinococcus halophilus+TX, Meira geulakonigii+TX, Metarhizium anisopliae (Met52®)+TX, Metarhizium anisopliae (Destruxin WP®)+TX, Metschnikowia fruticola (Shemer®)+TX, Metschnikowia pulcherrima+TX, Microdochium dimerum (Antibot®)+TX, Micromonospora coerulea+TX, Microsphaeropsis ochracea+TX, Muscodor albus 620 (Muscudor®)+TX, Muscodor roseus strain A3-5+TX, Mycorrhizae spp. (AMykor®+TX, Root Maximizer®)+TX, Myrothecium verrucaria strain AARC-0255 (DiTera®)+TX, BROS PLUS®+TX, Ophiostoma piliferum strain D97 (Sylvanex®)+TX, Paecilomyces farinosus+TX, Paecilomyces fumosoroseus (PFR-97®+TX, PreFeRal®)+TX, Paecilomyces linacinus (Biostat WP®)+TX, Paecilomyces lilacinus strain 251 (MeloCon WG®)+TX, Paenibacillus polymyxa+TX, Pantoea agglomerans (BlightBan C9-1®)+TX, Pantoea spp.+TX, Pasteuria spp. (Econem®)+TX, Pasteuria nishizawae+TX, Penicillium aurantiogriseum+TX, Penicillium billai (Jumpstart®+TX, TagTeam®)+TX, Penicillium brevicompactum+TX, Penicillium frequentans+TX, Penicillium griseofulvum+TX, Penicillium purpurogenum+TX, Penicillium spp.+TX, Penicillium viridicatum+TX, Phlebiopsis gigantean (Rotstop®)+TX, phosphate solubilizing bacteria (Phosphomeal®)+TX, Phytophthora cryptogea+TX, Phytophthora palmivora (Devine®)+TX, Pichia anomala+TX, Pichia guilermondii+TX, Pichia membranaefaciens+TX, Pichia onychis+TX, Pichia stipites+TX, Pseudomonas aeruginosa+TX, Pseudomonas aureofasciens (Spot-Less Biofungicide®)+TX, Pseudomonas cepacia+TX, Pseudomonas chlororaphis (AtEze®)+TX, Pseudomonas corrugate+TX, Pseudomonas fluorescens strain A506 (BlightBan A506®)+TX, Pseudomonas putida+TX, Pseudomonas reactans+TX, Pseudomonas spp.+TX, Pseudomonas syringae (Bio-Save®)+TX, Pseudomonas viridiflava+TX, Pseudomons fluorescens (Zequanox®)+TX, Pseudozyma flocculosa strain PF-A22 UL (Sporodex L®)+TX, Puccinia canaliculata+TX, Puccinia thlaspeos (Wood Warrior®)+TX, Pythium paroecandrum+TX, Pythium oligandrum (Polygandron®+TX, Polyversum®)+TX, Pythium periplocum+TX, Rhanella aquatilis+TX, Rhanella spp.+TX, Rhizobia (Dormal®+TX, Vault®)+TX, Rhizoctonia+TX, Rhodococcus globerulus strain AQ719+TX, Rhodosporidium diobovatum+TX, Rhodosporidium toruloides+TX, Rhodotorula spp.+TX, Rhodotorula glutinis+TX, Rhodotorula graminis+TX, Rhodotorula mucilagnosa+TX, Rhodotorula rubra+TX, Saccharomyces cerevisiae+TX, Salinococcus roseus+TX, Sclerotinia minor+TX, Sclerotinia minor (SARRITOR®)+TX, Scytalidium spp.+TX, Scytalidium uredinicola+TX, Spodoptera exigua nuclear polyhedrosis virus (Spod-X®+TX, Spexit®)+TX, Serratia marcescens+TX, Serratia plymuthica+TX, Serratia spp.+TX, Sordaria fimicola+TX, Spodoptera littoralis nucleopolyhedrovirus (Littovir®)+TX, Sporobolomyces roseus+TX, Stenotrophomonas maltophilia+TX, Streptomyces ahygroscopicus+TX, Streptomyces albaduncus+TX, Streptomyces exfoliates+TX, Streptomyces galbus+TX, Streptomyces griseoplanus+TX, Streptomyces griseoviridis (Mycostop®)+TX, Streptomyces lydicus (Actinovate®)+TX, Streptomyces lydicus WYEC-108 (ActinoGrow®)+TX, Streptomyces violaceus+TX, Tilletiopsis minor+TX, Tilletiopsis spp.+TX, Trichoderma asperellum (T34 Biocontrol®)+TX, Trichoderma gamsii (Tenet®)+TX, Trichoderma atroviride (Plantmate®)+TX, Trichoderma hamatum TH 382+TX, Trichoderma harzianum rifai (Mycostar®)+TX, Trichoderma harzianum T-22 (Trianum-P®+TX, PlantShield HC®+TX, RootShield®+TX, Trianum-G®)+TX, Trichoderma harzianum T-39 (Trichodex®)+TX, Trichoderma inhamatum+TX, Trichoderma koningii+TX, Trichoderma spp. LC 52 (Sentinel®)+TX, Trichoderma lignorum+TX, Trichoderma longibrachiatum+TX, Trichoderma polysporum (Binab T®)+TX, Trichoderma taxi+TX, Trichoderma virens+TX, Trichoderma virens (formerly Gliocladium virens GL-21) (SoilGuard®)+TX, Trichoderma viride+TX, Trichoderma viride strain ICC 080 (Remedier®)+TX, Trichosporon pullulans+TX, Trichosporon spp.+TX, Trichothecium spp.+TX, Trichothecium roseum+TX, Typhula phacorrhiza strain 94670+TX, Typhula phacorrhiza strain 94671+TX, Ulocladium atrum+TX, Ulocladium oudemansii (Botry-Zen®)+TX, Ustilago maydis+TX, various bacteria and supplementary micronutrients (Natural II®)+TX, various fungi (Millennium Microbes®)+TX, Verticillium chlamydosporium+TX, Verticillium lecanii (Mycotal®+TX, Vertalec®)+TX, Vip3Aa20 (VIPtera®)+TX, Virgibacillus marismortui+TX, Xanthomonas campestris pv. Poae (Camperico®)+TX, Xenorhabdus bovienii+TX, Xenorhabdus nematophilus; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, Chenopodium ambrosioides near ambrosioides (Requiem®)+TX, Chrysanthemum extract (Crisant®)+TX, extract of neem oil (Trilogy®)+TX, essentials oils of Labiatae (Botania®)+TX, extracts of clove rosemary peppermint and thyme oil (Garden insect Killer®)+TX, Glycinebetaine (Greenstim®)+TX, garlic+TX, lemongrass oil (GreenMatch®)+TX, neem oil+TX, Nepeta cataria (Catnip oil)+TX, Nepeta catarina+TX, nicotine+TX, oregano oil (MossBuster®)+TX, Pedaliaceae oil (Nematon®)+TX, pyrethrum+TX, Quillaja saponaria (NemaQ®)+TX, Reynoutria sachalinensis (Regalia®+TX, Sakalia®)+TX, rotenone (Eco Roten®)+TX, Rutaceae plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame peppermint thyme and cinnamon extracts (EF 300®)+TX, mixture of clove rosemary and peppermint extract (EF 400®)+TX, mixture of clove peppermint garlic oil and mint (Soil Shot®)+TX, kaolin (Screen®)+TX, storage glucam of brown algae (Laminarin®); and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC-LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, (E+TX,Z+TX,Z)-3+TX,8+TX,11 Tetradecatrienyl acetate+TX, (Z+TX,Z+TX,E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: *Aphelinus abdominalis*+TX, *Aphidius ervi* (Aphelinus-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius califomicus* (Amblyline®+TX, Spical®)+TX, *Amblyseius cucumeris* (Thripex®+TX, Bugline Cucumeris®)+TX, *Amblyseius fallacis* (Fallacis®)+TX, *Amblyseius swirskii* (Bugline Swirskii®+TX, Swirskii-Mite®)+TX, *Amblyseius womersleyi* (WomerMite®)+TX, *Amitus hesperidum*+TX, *Anagrus atomus*+TX, *Anagrus fusciventris*+TX, *Anagrus kamali*+TX, *Anagrus loecki*+TX, *Anagrus pseudococci* (Citripar®)+TX, *Anicetus benefices*+TX, *Anisopteromalus calandrae*+TX, *Anthocoris nemoralis* (Anthocoris-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (Delphastus®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (Encarsia Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus califormicus*+TX, *Eretmocerus eremicus* (Ercal®+TX, Eretline E®)+TX, *Eretmocerus eremicus* (Bemimix®)+TX, *Eretmocerus hayati*+TX, *Eretmocerus mundus* (Bemipar®+TX, Eretline M®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack+TX, Nematop®)+TX, *Heterorhabditis megidis* (Nemasys+TX, BioNem+TX, Exhibitline Hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline M®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopfi* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus califomicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline I®)+TX, *Orius laevigatus* (Thripor-L®+TX, Oriline I®)+TX, *Orius majusculus* (Oriline M®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline P®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, Steinernema-System®+TX, NemAttack®+TX, Nemaplus®+TX, Exhibitline Sf®+TX, Scia-Rid®+TX, Entonem®)+TX, *Steinernema kraussei* (Nemasys L®+TX, BioNem L®+TX, Exhibitline Srb®)+TX, *Steinernema riobrave* (BioVector®+TX, BioVektor®)+TX, *Steinernema scapterisci* (Nematac S®)+TX, *Steinernema* spp.+TX, Steinernematid spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine B®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Callego®)+TX, Copper Octanoate (Cueva®)+TX, Delta traps (Trapline D®)+TX, *Erwinia amylovora* (Harpin) (ProAct®+TX, Ni-HIBIT Gold CST®)+TX, Ferri-phosphate (Ferramol®)+TX, Funnel traps (Trapline Y®)+TX, Gallex®+TX, Growers Secret®+TX, Homo-brassonolide+TX, Iron Phosphate (Lilly Miller Worry Free Ferramol Slug & Snail Bait®)+TX, MCP hail trap (Trapline F®)+TX, *Microctonus hyperodae*+TX, *Mycoleptodiscus terrestris* (Des-X®)+TX, BioGain®+TX, Aminomite®+TX, Zenox®+TX, Pheromone trap (Thripline Ams®)+TX, potassium bicarbonate (MilStop®)+TX, potassium salts of fatty acids (Sanova®)+TX, potassium silicate solution (SD-Matrix®)+TX, potassium iodide+potassium-thiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+B®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from Tables 1 to 12 and Table P with active ingredients described above comprises a compound selected from Tables 1 to 12 and Table P and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables 1 to 12 and Table P and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1 to 12 and Table P and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

BIOLOGICAL EXAMPLES

Example B1

Activity Against *Spodoptera littoralis* (Egyptian Cotton Leaf Worm)

Cotton leaf discs were placed on agar in 24-well microtiter plates and sprayed with aqueous test solutions prepared from 10,000 ppm DMSO stock solutions. After drying the leaf discs were infested with five L1 larvae. The samples were assessed for mortality, anti-feedant effect, and growth inhibition in comparison to untreated samples 3 days after infestation. Control of *Spodoptera littoralis* by a test sample is when at least one of mortality, anti-feedant effect, and growth inhibition is higher than the untreated sample.

The following compounds resulted in at least 80% control at an application rate of 200 ppm: P1, P2, P4, P6, P7, P9, P11, P13, P14, P16, P17, P18, P19, P20, P21, P22, P23, P24, P25, P26, P27, P28, P29, P32, P35, P37, P38, P39, P41, P42, P40, P44, P45, P48, P50, P52 and P53.

Example B2

Activity Against *Spodoptera littoralis* (Egyptian Cotton Leaf Worm)

Test compounds were applied by pipette from 10,000 ppm DMSO stock solutions into 24-well plates and mixed with agar. Lettuce seeds were placed on the agar and the multi well plate was closed by another plate which contains also agar. After 7 days the roots have absorbed the compound and the lettuce has grown into the lid plate. The lettuce leafs were now cut off into the lid plate. *Spodoptera* eggs were pipetted through a plastic stencil on a humid gel blotting paper and the plate closed with it. The samples were assessed for mortality, anti-feedant effect and growth inhibition in comparison to untreated samples 6 days after infestation.

The following compounds gave an effect of at least 80% in at least one of the three categories (mortality, anti-feedancy, or growth inhibition) at a test rate of 12.5 ppm: P6, P7, P9, P14, P16, P17, P20, P21, P22, P23, P25, P26, P27, P28, P29, P39, P41, P40, P48, P50 and P52.

Example B3

Activity Against *Plutella xylostella* (Diamond Back Moth)

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm: P6, P7, P8, P9, P11, P13, P14, P16, P17, P20, P21, P22, P23, P24, P25, P26, P27, P28, P29, P32, P35, P37, P38, P39, P41, P40, P45, P48, P50, P52, P53 and P54.

Example B4

Activity Against *Diabrotica* Balteata (Corn Root Worm)

Maize sprouts, placed on an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm: P1, P2, P5, P6, P7, P8, P9, P11, P13, P14, P16, P17, P18, P19, P20, P21, P22, P23, P24, P25, P26, P27, P28, P29, P32, P34, P35, P36, P37, P38, P39, P41, P40, P45, P46, P47, P48, P50, P52, P53 and P54.

Example B5

Activity Against *Myzus persicae* (Green Peach Aphid)

Sunflower leaf discs were placed on agar in a 24-well microtiter plate and sprayed with aqueous test solutions prepared from 10,000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm: P4, P6, P7, P9, P11, P12, P13, P14, P16, P17, P20, P21, P22, P23, P26, P27, P28, P29, P34, P37, P39, P41, P40, P43, P45, P46, P47, P48, P50, P52 and P54.

Example B6

Activity Against *Myzus persicae* (Green Peach Aphid)

Roots of pea seedlings infested with an aphid population of mixed ages were placed directly in the aqueous test solutions prepared from 10,000 DMSO stock solutions. The samples were assessed for mortality 6 days after placing seedlings in test solutions.

The following compounds resulted in at least 80% mortality at a test rate of 24 ppm: P9, P12, P14, P15, P17, P23, P27, P29, P36, P37, P39, P41, P40, P43, P44, P45, P46, P47 and P54.

Example B7

Activity Against *Frankliniella occidentalis* (Western Flower *Thrips*)

Sunflower leaf discs were placed on agar in 24-well microtiter plates and sprayed with aqueous test solutions prepared from 10,000 DMSO stock solutions. After drying the leaf discs were infested with a *Frankliniella* population of mixed ages. The samples were assessed for mortality 7 days after infestation.

The following compounds resulted in at least 80% mortality at an application rate of 200 ppm: P3, P6, P7, P8, P9, P13, P14, P17, P21, P22, P23, P26, P27, P28, P41, P40, P45, P46, P48, P50, P52 and P54.

Example B8

Activity Against *Bemisia tabaci* (Cotton White Fly)

Cotton leaf discs were placed on agar in 24-well microtiter plates and sprayed with aqueous test solutions prepared from 10,000 ppm DMSO stock solutions. After drying the leaf discs were infested with adult white flies. The samples were checked for mortality 6 days after incubation.

The following compounds resulted in at least 80% mortality at an application rate of 200 ppm: P6, P14, P17, P27 P32, P37, P40, P45 and P48.

Example B9

Activity Against *Euschistus heros* (Neotropical Brown Stink Bug)

Soybean leaf on agar in 24-well microtiter plates were sprayed with aqueous test solutions prepared from 10,000 ppm DMSO stock solutions. After drying the leaf were infested with N-2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm: P3, P4, P6, P7, P9, P11, P14, P17, P20, P21, P22, P23, P24, P25, P26, P27, P28, P37, P39, P41, P40, P45, P47, P48, P50, P52 and P54.

Example B10

Activity Against *Tetranychus urticae* (Two-Spotted Spider Mite)

Bean leaf discs on agar in 24-well microtiter plates were sprayed with aqueous test solutions prepared from 10,000 ppm DMSO stock solutions. After drying the leaf discs were infested with a mite population of mixed ages. The samples were assessed for mortality on mixed population (mobile stages) 8 days after infestation.

The following compound resulted in at least 80% mortality at an application rate of 200 ppm: P19.

Example B11

Activity Against *Aedes aegypti* (Yellow Fever Mosquito)

Test solutions, at an application rate of 200 ppm in ethanol, were applied to 12-well tissue culture plates. Once the deposits were dry, five, two to five days old adult female *Aedes aegypti* were added to each well, and sustained with a 10% sucrose solution in a cotton wool plug. Assessment of knockdown was made one hour after introduction, and mortality was assessed at 24 and 48 hours after introduction.

The following compounds gave at least 80% control of *Aedes aegypti* after 48 h and/or 24 h: P7, P17, P22, P26, P27, P39 and P40.

Example B12

Activity Against *Thrips tabaci* (Onion *Thrips*)

Sunflower leaf discs were placed on agar in 24-well microtiter plates and sprayed with aqueous test solutions prepared from 10,000 ppm DMSO stock solutions. After drying the leaf discs were infested with a *thrips* population of mixed ages. The samples were assessed for mortality 6 days after infestation.

The following compounds resulted in at least 80% mortality at an application rate of 200 ppm: P6, P7, P13, P14, P15, P17, P22, P23, P25, P26, P27, P29, P32, P41, P42, P40 and P45.

Example B13

Activity Against *Anopheles stephensi* (Indian Malaria Mosquito)

Test solutions, at an application rate of 200 ppm in ethanol, were applied to 12-well tissue culture plates. Once the deposits were dry, five, two to five day old adult female *Anopheles stephensi* were added to each well, and sustained with a 10% sucrose solution in a cotton wool plug. Assessment of knockdown was made one hour after introduction, and mortality was assessed at 24 and 48 hours after introduction.

The following compounds gave at least 80% control of *Anopheles stephensi* after 48 h and/or 24 h: P17, P22, P26, P27 and P39.

The invention claimed is:
1. A compound of formula I

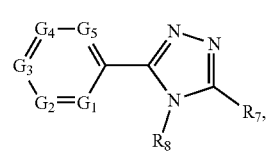

wherein
G$_1$ is nitrogen or CR$_2$;
G$_2$ is nitrogen or CR$_3$;
G$_3$ is nitrogen or CR$_4$;
G$_4$ is nitrogen or CR$_5$;
G$_5$ is nitrogen or CR$_6$, with the proviso that not more than 2 nitrogens as G may follow consecutively;
R$_2$, R$_3$, R$_4$, R$_5$ or R$_6$ are, independently from each other, hydrogen, halogen, C$_1$-C$_4$haloalkyl, C$_1$-C$_4$haloalkyl substituted by one or two hydroxy, C$_1$-C$_4$haloalkyl substituted by one or two methoxy, C$_1$-C$_4$haloalkyl substituted by one or two cyano; or
R$_2$, R$_3$, R$_4$, R$_5$ or R$_6$ are, independently from each other, C$_1$-C$_4$haloalkylsulfanyl, C$_1$-C$_4$haloalkylsulfinyl, C$_1$-C$_4$haloalkylsulfonyl, C$_1$-C$_4$haloalkoxy, SF$_5$, phenylcarbonylthio, cyano, mercapto, C$_1$-C$_4$alkoxycarbonyl, C$_1$-C$_4$alkylcarbonyl or —C(O)C$_1$-C$_4$haloalkyl; or
R$_2$, R$_3$, R$_4$, R$_5$ or R$_6$ are, independently from each other, C$_3$-C$_6$cycloalkyl which can be mono- or polysubstituted by substituents selected from the group consisting of halogen, cyano and C$_1$-C$_4$alkyl;
or two adjacent R$_i$, wherein R$_i$ is selected from R$_2$, R$_3$, R$_4$, R$_5$ and R$_6$, taken together may form a fragment —OCH$_2$O— or —OCF$_2$O—,
R$_8$ is hydrogen, C$_1$-C$_4$alkyl or C$_1$-C$_4$haloalkyl;
R$_7$ is a radical selected from the group consisting of formula Q1 and Q2

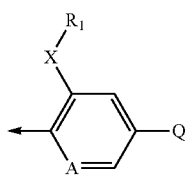
Q$_1$

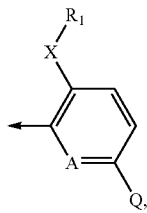
Q$_2$ wherein the arrow denotes the point of attachment to the triazole ring;
and wherein A represents CH or N;
Q is phenyl which can be mono- or polysubstituted by substituents selected from the group consisting of halogen, cyano, C$_1$-C$_4$alkyl, C$_1$-C$_4$haloalkyl, C$_1$-C$_4$haloalkoxy, C$_1$-C$_4$alkoxy, C$_1$-C$_4$haloalkylsulfanyl, C$_1$-C$_4$haloalkylsulfinyl, C$_1$-C$_4$haloalkylsulfonyl and —C(O)C$_1$-C$_4$haloalkyl; or
Q is a five- to ten-membered monocyclic or fused bicyclic ring system linked via a carbon atom to the ring which contains the group A, said ring system can be aromatic, partially saturated or fully saturated and contains 1 to 4 hetero atoms selected from the group consisting of nitrogen, oxygen and sulfur, it not being possible for each ring system to contain more than 2 oxygen atoms and more than 2 sulfur atoms, said five-to ten-membered ring system can be mono- to polysubstituted by substituents independently selected from the group consisting of halogen, cyano, C$_1$-C$_4$alkyl, C$_1$-C$_4$haloalkyl, C$_1$-C$_4$haloalkoxy, C$_1$-C$_4$alkoxy, C$_1$-C$_4$alkylsulfanyl, C$_1$-C$_4$alkylsulfinyl, C$_1$-C$_4$alkylsulfonyl, —C(O)C$_1$-C$_4$alkyl, C$_1$-C$_4$haloalkylsulfanyl, C$_1$-C$_4$haloalkylsulfinyl, C$_1$-C$_4$haloalkylsulfonyl and —C(O)C$_1$-C$_4$haloalkyl; or
Q is a five- to six-membered, aromatic, partially saturated or fully saturated ring system linked via a nitrogen atom to the ring which contains the group A, said ring system can be mono- or polysubstituted by substituents selected from the group consisting of halogen, cyano, C$_1$-C$_4$alkyl, C$_1$-C$_4$haloalkyl, C$_1$-C$_4$haloalkoxy, C$_1$-C$_4$alkoxy, C$_1$-C$_4$alkylsulfanyl, C$_1$-C$_4$alkylsulfinyl, C$_1$-C$_4$alkylsulfonyl, —C(O)C$_1$-C$_4$alkyl, C$_1$-C$_4$haloalkylsulfanyl, C$_1$-C$_4$haloalkylsulfinyl, C$_1$-C$_4$haloalkylsulfonyl and —C(O)C$_1$-C$_4$haloalkyl; and said ring system contains 1, 2 or 3 heteroatoms selected from the group consisting of nitrogen, oxygen and sulfur, where said ring system may not contain more than one oxygen atom and not more than one sulfur atom; or
Q is C$_3$-C$_6$cycloalkyl, or C$_3$-C$_6$cycloalkyl mono- or polysubstituted by substituents selected from the group consisting of halogen, cyano, C$_1$-C$_4$alkyl, C$_1$-C$_4$haloalkyl, C$_3$-C$_6$cycloalkyl and phenyl, wherein said phenyl can be mono- or polysubstituted by substituents selected from the group consisting of halogen, cyano, C$_1$-C$_4$alkyl, C$_1$-C$_4$haloalkyl, C$_1$-C$_4$haloalkoxy, C$_1$-C$_4$alkoxy, C$_1$-C$_4$haloalkylsulfanyl, C$_1$-C$_4$haloalkylsulfinyl, C$_1$-C$_4$haloalkylsulfonyl and —C(O)C$_1$-C$_4$haloalkyl; or
Q is C$_2$-C$_6$alkenyl, or C$_2$-C$_6$alkenyl mono- or polysubstituted by substituents selected from the group consisting of halogen, cyano, C$_1$-C$_4$alkyl, C$_1$-C$_4$haloalkyl, C$_1$-C$_4$alkoxy, C$_3$-C$_6$cycloalkyl and phenyl, wherein said phenyl can be mono- or polysubstituted by substituents selected from the group consisting of halogen, cyano, C$_1$-C$_4$alkyl, C$_1$-C$_4$haloalkyl, C$_1$-C$_4$haloalkoxy, C$_1$-C$_4$alkoxy, C$_1$-C$_4$haloalkylsulfanyl, C$_1$-C$_4$haloalkylsulfinyl, C$_1$-C$_4$haloalkylsulfonyl and —C(O)C$_1$-C$_4$haloalkyl; or
Q is C$_2$-C$_6$alkynyl, or C$_2$-C$_6$alkynyl mono- or polysubstituted by substituents selected from the group consisting of halogen, cyano, C$_1$-C$_4$alkyl, C$_1$-C$_4$haloalkyl, C$_3$-C$_6$cycloalkyl, tri(C$_1$-C$_4$alkyl)silyl and phenyl, wherein said phenyl can be mono- or polysubstituted by substituents selected from the group consisting of halogen, cyano, C$_1$-C$_4$alkyl, C$_1$-C$_4$haloalkyl, C$_1$-C$_4$haloalkoxy, C$_1$-C$_4$alkoxy, C$_1$-C$_4$haloalkylsulfanyl, C$_1$-C$_4$haloalkylsulfinyl, C$_1$-C$_4$haloalkylsulfonyl and —C(O)C$_1$-C$_4$haloalkyl; or
Q is C$_1$-C$_6$haloalkylsulfanyl, C$_1$-C$_6$haloalkylsulfinyl, C$_1$-C$_6$haloalkylsulfonyl, C$_1$-C$_6$haloalkoxy, —C(O)C$_1$-C$_4$haloalkyl, C$_1$-C$_6$alkylsulfanyl, C$_1$-C$_6$alkylsulfinyl, or C$_1$-C$_6$alkylsulfonyl;
X is S, SO or SO$_2$; and
R$_1$ is C$_1$-C$_4$alkyl, C$_1$-C$_4$haloalkyl, C$_3$-C$_6$cycloalkyl, C$_3$-C$_6$cycloalkyl-C$_1$-C$_4$alkyl; or
R$_1$ is C$_3$-C$_6$cycloalkyl mono- or polysubstituted by substituents selected from the group consisting of halogen, cyano and C$_1$-C$_4$alkyl; or
R$_1$ is C$_3$-C$_6$cycloalkyl-C$_1$-C$_4$alkyl mono- or polysubstituted by substituents selected from the group consisting of halogen, cyano and C$_1$-C$_4$alkyl; or $R_1$ is $C_2$-$C_6$alkenyl, $C_2$-$C_6$haloalkenyl or $C_2$-$C_6$alkynyl;

and agrochemically acceptable salts, stereoisomers, enantiomers, tautomers and N-oxides of the compounds of formula I.

2. A compound of formula I according to claim 1, wherein Q is selected from the group consisting of the following heterocyclic groups:

pyrrolyl; pyrazolyl; isoxazolyl; furanyl; thienyl; imidazolyl; oxazolyl; thiazolyl;

isothiazolyl; triazolyl; oxadiazolyl; thiadiazolyl; tetrazolyl; furyl; pyridyl;

pyrimidyl; pyrazinyl; pyridazinyl; triazinyl, pyranyl; quinazolinyl;

isoquinolinyl; indolizinyl; isobenzofuranylnaphthyridinyl; quinoxalinyl;

cinnolinyl; phthalazinyl; benzothiazolyl; benzoxazolyl; benzotriazolyl;

indazolyl; indolyl; (1H-pyrrol-1-yl)-; (1H-pyrrol-2-yl)-; (1H-pyrrol-3-yl)-; (1H-pyrazol-1-yl)-; (1H-pyrazol-3-yl)-; (3H-pyrazol-3-yl)-; (1H-pyrazol-4-yl)-; (3-isoxazolyl)-; (5-isoxazolyl)-; (2-furanyl)-; (3-furanyl)-; (2-thienyl)-; (3-thienyl)-; (1H-imidazol-2-yl)-; (1H-imidazol-4-yl)-; (1H-imidazol-5-yl)-; (2-oxazol-2-yl)-; (oxazol-4-yl)-; (oxazol-5-yl)-; (thiazol-2-yl)-; (thiazol-4-yl)-; (thiazol-5-yl)-; (isothiazol-3-yl)-; (isothiazol-5-yl)-; (1H-1,2,3-triazol-1-yl)-; (1H-1,2,4-triazol-3-yl)-; (4H-1,2,4-triazol-4-yl)-; (1H-1,2,4-triazol-1-yl)-; (1,2,3-oxadiazol-2-yl)-; (1,2,4-oxadiazol-3-yl)-; (1,2,4-oxadiazol-4-yl)-; (1,2,4-oxadiazol-5-yl)-; (1,2,3-thiadiazol-2-yl)-; (1,2,4-thiadiazol-3-yl)-; (1,2,4-thiadiazol-4-yl)-; (1,3,4-thiadiazol-5-yl)-; (1H-tetrazol-1-yl)-; (1H-tetrazol-5-yl)-; (2H-tetrazol-5-yl)-; (2-pyridyl)-; (3-pyridyl)-; (4-pyridyl)-; (2-pyrimidinyl)-; (4-pyrimidinyl)-; (5-pyrimidinyl)-; (2-pyrazinyl)-; (3-pyridazinyl)-; (4-pyridazinyl)-; (1,3,5-triazin-2-yl)-; (1,2,4-triazin-5-yl)-; (1,2,4-triazin-6-yl)-; (1,2,4-triazin-3-yl)-; (furazan-3-yl)-; (2-quinolinyl)-; (3-quinolinyl)-; (4-quinolinyl)-; (5-quinolinyl)-; (6-quinolinyl)-; (3-isoquinolnyl)-; (4-isoquinolnyl)-; (2-quinozolinyl)-; (2-quinoxalinyl)-; (5-quinoxalinyl)-; (pyrido[2,3-b]pyrazin-7-yl)-; (benzoxazol-5-yl)-; (benzothiazol-5-yl)-; (benzo[b]thien-2-yl) and (benzo[1,2,5]oxadiazol-5-yl)-; indolinyl and tetrahydroquinolynyl.

3. A compound of formula I according to claim 1, wherein Q is selected from the group consisting of J-0 to J-51:

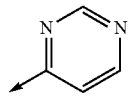
J-0

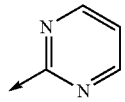
J-1

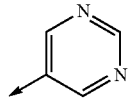
J-2

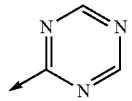
J-3

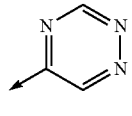
J-4

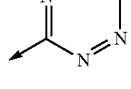
J-5

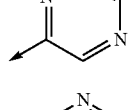
J-6

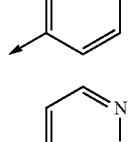
J-7

-continued

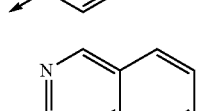
J-8

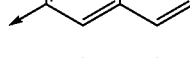
J-9

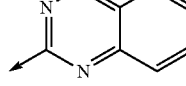
J-10

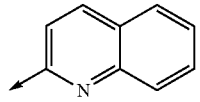
J-11

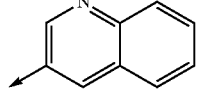
J-12

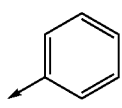
J-13

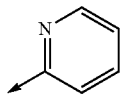
J-14

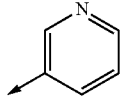
J-15

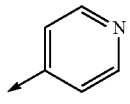
J-16

J-17

175
-continued
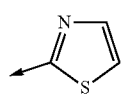
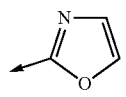
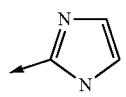
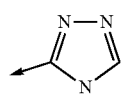
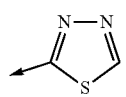
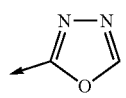
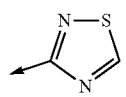
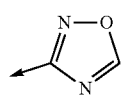
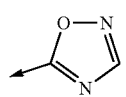
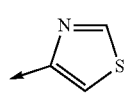
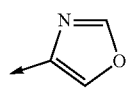
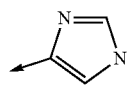
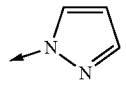
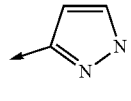
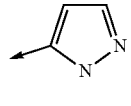
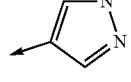
176
-continued
J-18
J-19
J-20
J-21
J-22
J-23
J-24
J-25
J-26
J-27
J-28
J-29
J-30
J-31
J-32
J-33
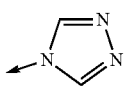
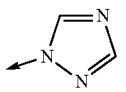
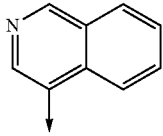
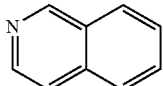
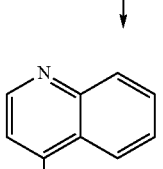
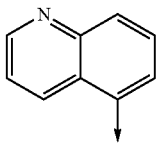
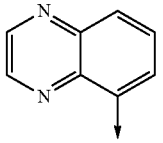
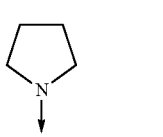
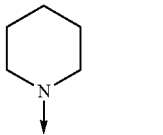
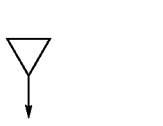
J-34
J-35
J-36
J-37
J-38
J-39
J-40
J-41
J-42
J-43
J-44

-continued

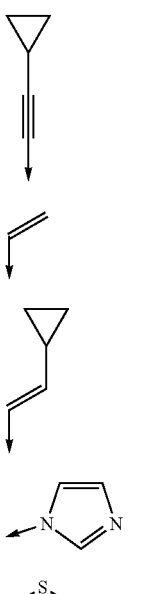

J-45

J-46

J-47

J-48

J-49

J-50

J-51 wherein each group J-0 to J-48 is mono-, di- or trisubstituted with Rx, wherein each Rx is, independently selected from hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$$C_4$haloalkylsulfanyl, $C_1$-$C_4$haloalkylsulfinyl, $C_1$-$C_4$haloalkylsulfonyl and —C(O)$C_1$-$C_4$haloalkyl.

4. A compound of formula I according to claim 1, represented by the compounds of formula I-1

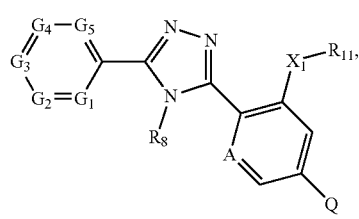
(I-1)

wherein

A, Q, $G_1$, $G_2$, $G_3$, $G_4$, and $G_5$ are as defined under formula I in claim 1;

$X_1$ is S, SO or $SO_2$;

$R_{11}$ is methyl, ethyl, n-propyl, i-propyl or cyclopropylmethyl; and $R_8$ is as defined under formula I in claim 1.

5. A compound of formula I according to claim 1 represented by the compounds of formula I-2

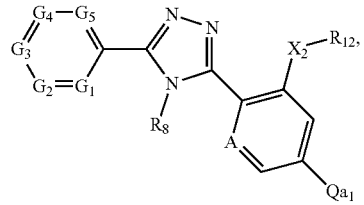
(I-2)

wherein

A, $G_1$, $G_2$, $G_3$, $G_4$, and $G_5$ are as defined under formula I in claim 1;

$X_2$ is S, SO or $SO_2$;

$R_{12}$ is methyl, ethyl, n-propyl, i-propyl or cyclopropylmethyl;

$R_8$ is as defined above under formula I in claim 1; and $Qa_1$ is selected from the group consisting of

J-0

J-1

J-5

J-30

J-35

J-43

J-46

J-48

J-49

J-50 and

J-51 wherein each group J-0 to J-48 is mono-, di- or trisubstituted with Rx, wherein each Rx is, independently selected from hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

6. A compound of formula I according to claim 1, represented by the compounds of formula I-3

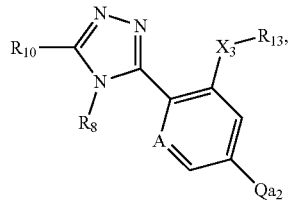
(I-3)

wherein

A is N or CH;

$R_{10}$ is pyridyl or pyrimidyl mono- or polysubstituted by $C_1$-$C_4$haloalkyl;

$X_3$ is S or $SO_2$;

$Qa_2$ is selected from the group consisting of

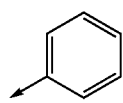 J-0

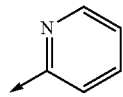 J-1

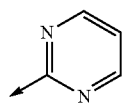 J-5

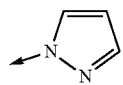 J-30

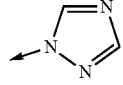 J-35

 J-43

 J-46

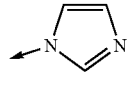 J-48

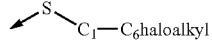 J-49

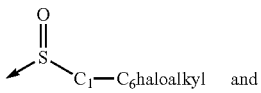 J-50 and

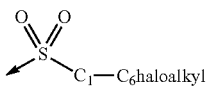 J-51 wherein each group J-0 to J-48 is mono-, di- or trisubstituted with Rx, wherein each Rx is, independently selected from hydrogen, halogen, cyano, $C_1$-$C_4$haloalkyl and $C_1$-$C_4$alkoxy;

$R_{13}$ is $C_1$-$C_4$alkyl; and $R_8$ is $C_1$-$C_4$alkyl.

7. A compound of formula I according to claim 1, represented by the compounds of formula I-4

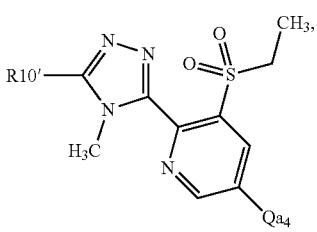
(I-4)

wherein $R_{10}'$ is pyridyl or pyrimidyl monosubstituted by $C_1$-$C_4$haloalkyl; and $Qa_4$ is selected from the group consisting of

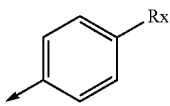 J-0a

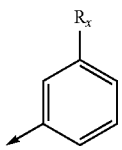 J-0b

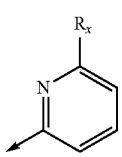 J-1a

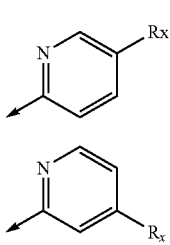 J-1b

J-1c

-continued
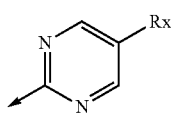 J-5a
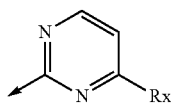 J-5b
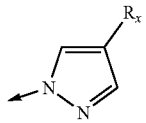 J-30a
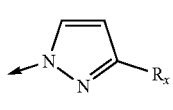 J-30b
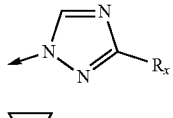 J-35a
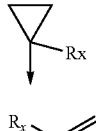 J-43a
 J-46a
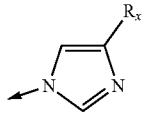 J-48a
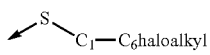 J-49
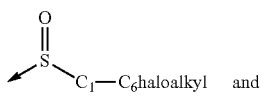 J-50 and
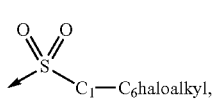 J-51
wherein each Rx is independently selected from hydrogen, halogen, cyano, $C_1$-$C_4$haloalkyl and $C_1$-$C_4$alkoxy.
8. A compound of formula I according to claim 1, represented by the compounds of formula I-5
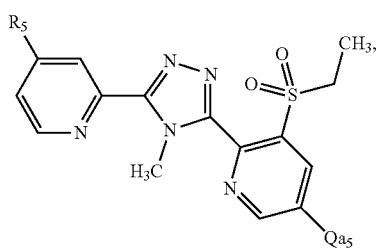 (I-5)
wherein
$R_5$ is $C_1$-$C_4$haloalkyl; and
$Qa_5$ is selected from the group consisting of
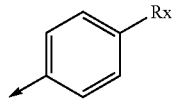 J-0a
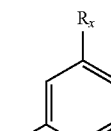 J-0b
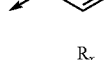 J-1a
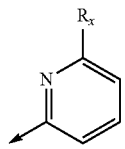 J-1b
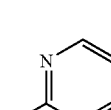 J-1c
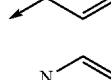 J-5a
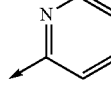 J-5b
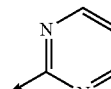 J-30a
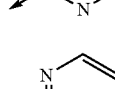 J-30b
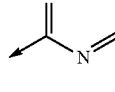 J-35a
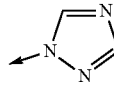 J-43a
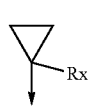 J-46a

-continued

[J-48a: imidazole with Rx]

$\overset{S}{\diagup}$—$C_1$–$C_6$haloalkyl  (J-49)

$\overset{O}{\underset{\parallel}{S}}$—$C_1$–$C_6$haloalkyl and  (J-50)

$\overset{O\ \ O}{\underset{\parallel\ \ \parallel}{S}}$—$C_1$–$C_6$haloalkyl,  (J-51)

wherein each Rx is, independently selected from hydrogen, halogen, cyano, $C_1$-$C_4$haloalkyl and $C_1$-$C_4$alkoxy.

9. A compound of formula I according to claim 1, represented by the compounds of formula I-6

(I-6)

[Structure with $R_5$, pyrimidine, triazole, $CH_3$, $SO_2$–ethyl, pyridine with $Qa_6$, $H_3C$]

wherein
$R_6$ is $C_1$-$C_4$haloalkyl; and
$Qa_6$ is selected from the group consisting of

[J-0a: phenyl-Rx para]

[J-0b: phenyl-Rx meta]

[J-5a: pyrimidine-Rx]

[J-5b: pyrimidine-Rx]

[J-35a: triazole-Rx]

[J-43a: cyclopropyl-Rx]

wherein each Rx is, independently selected from hydrogen, halogen and cyano.

10. A compound of formula I according to claim 1, represented by the compounds of formula I-1p (I-1p)

[Structure with $G_4$-$G_5$, $G_3$, $G_2$=$G_1$, triazole, $X_1$-$R_{11}$, $R_8$, A, Q]

wherein
A, Q, $G_1$, $G_2$, $G_3$, $G_4$, and $G_5$ are as defined under formula I in claim 1;
$X_1$ is S, SO or $SO_2$;
$R_{11}$ is methyl, ethyl, n-propyl, i-propyl or cyclopropylmethyl; and
$R_8$ is as defined under formula I in claim 1.

11. A compound of formula I according to claim 1 represented by the compounds of formula I-2p (I-2p)

[Structure with $G_4$-$G_5$, $G_3$, $G_2$=$G_1$, triazole, $X_2$-$R_{12}$, $R_8$, A, Q]

wherein
A, Q, $G_1$, $G_2$, $G_3$, $G_4$, and $G_5$ are as defined under formula I in claim 1;
$X_2$ is S, SO or $SO_2$;
$R_{12}$ is methyl, ethyl, n-propyl, i-propyl or cyclopropylmethyl;
$R_8$ is as defined above under formula I in claim 1; and
Q is selected from the group consisting of

[J-0: phenyl]

[J-5: pyrimidine]

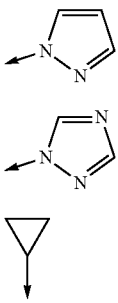

wherein each group J-0 to J-43 is mono-, di- or trisubstituted with Rx, wherein each Rx is, independently selected from hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl.

12. A pesticidal composition, which comprises at least one compound of formula I according to claim 1 or, where appropriate, a tautomer thereof, in each case in free form or in agrochemically utilizable salt form, as active ingredient and at least one auxiliary.

13. A method for controlling pests, which comprises applying a composition according to claim 12 to the pests or their environment with the exception of a method for treatment of the human or animal body by surgery or therapy and diagnostic methods practised on the human or animal body.

14. A method for the protection of plant propagation material from the attack by pests, which comprises treating the propagation material or the site, where the propagation material is planted, with a composition according to claim 12.

15. A compound of formula (Iab)

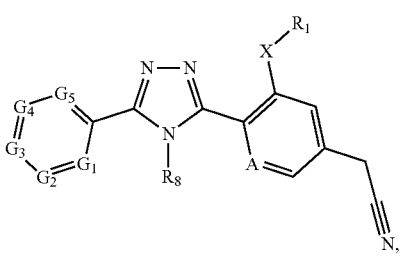

(Iab)

wherein
$G_1$ is nitrogen or $CR_2$;
$G_2$ is nitrogen or $CR_3$;
$G_3$ is nitrogen or $CR_4$;
$G_4$ is nitrogen or $CR_5$;
$G_5$ is nitrogen or $CR_6$, with the proviso that not more than 2 nitrogens as G may follow consecutively;
$R_2$, $R_3$, $R_4$, $R_5$ or $R_6$ are, independently from each other, hydrogen, halogen, $C_1$-$C_4$haloalkyl, $C_1$-$C_4$haloalkyl substituted by one or two hydroxy, $C_1$-$C_4$haloalkyl substituted by one or two methoxy, $C_1$-$C_4$haloalkyl substituted by one or two cyano; or
$R_2$, $R_3$, $R_4$, $R_5$ or $R_6$ are, independently from each other, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $SF_5$, phenylcarbonylthio, cyano, mercapto, $C_1$-$C_4$alkoxycarbonyl, $C_1$-$C_4$alkylcarbonyl or —C(O)$C_1$-$C_4$haloalkyl; or $R_2$, $R_3$, $R_4$, $R_5$ or $R_6$ are, independently from each other, $C_3$-$C_6$cycloalkyl which can be mono- or polysubstituted by substituents selected from the group consisting of halogen, cyano and $C_1$-$C_4$alkyl;

or two adjacent $R_i$, wherein $R_i$ is selected from $R_2$, $R_3$, $R_4$, $R_5$ and $R_6$, taken together may form a fragment —OCH$_2$O— or —OCF$_2$O—, $R_8$ is hydrogen, $C_1$-$C_4$alkyl or $C_1$-$C_4$haloalkyl;
A represents CH or N;
X is S, SO or SO$_2$; and
$R_1$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl; or
$R_1$ is $C_3$-$C_6$cycloalkyl mono- or polysubstituted by substituents selected from the group consisting of halogen, cyano and $C_1$-$C_4$alkyl; or
$R_1$ is $C_3$-$C_6$cycloalkyl-$C_1$-$C_4$alkyl mono- or polysubstituted by substituents selected from the group consisting of halogen, cyano and $C_1$-$C_4$alkyl; or
$R_1$ is $C_2$-$C_6$alkenyl, $C_2$-$C_6$haloalkenyl or $C_2$-$C_6$alkynyl.

16. A compounds of formula XVII-Int

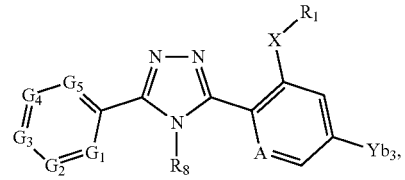

(XVII-Int)

wherein
$G_1$ is nitrogen or $CR_2$;
$G_2$ is nitrogen or $CR_3$;
$G_3$ is nitrogen or $CR_4$;
$G_4$ is nitrogen or $CR_5$;
$G_5$ is nitrogen or $CR_6$, with the proviso that not more than 2 nitrogens as G may follow consecutively;
$R_2$, $R_3$, $R_4$, $R_5$ or $R_6$ are, independently from each other, hydrogen, halogen, $C_1$-$C_4$haloalkyl, $C_1$-$C_4$haloalkyl substituted by one or two hydroxy, $C_1$-$C_4$haloalkyl substituted by one or two methoxy, $C_1$-$C_4$haloalkyl substituted by one or two cyano; or
$R_2$, $R_3$, $R_4$, $R_5$ or $R_6$ are, independently from each other, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $SF_5$, phenylcarbonylthio, cyano, mercapto, $C_1$-$C_4$alkoxycarbonyl, $C_1$-$C_4$alkylcarbonyl or—C(O)$C_1$-$C_4$haloalkyl; or
$R_2$, $R_3$, $R_4$, $R_5$ or $R_6$ are, independently from each other, $C_3$-$C_6$cycloalkyl which can be mono- or polysubstituted by substituents selected from the group consisting of halogen, cyano and $C_1$-$C_4$alkyl;
or two adjacent $R_i$, wherein $R_i$ is selected from $R_2$, $R_3$, $R_4$, $R_5$ and $R_6$, taken together may form a fragment —OCH$_2$O— or —OCF$_2$O—,
$R_8$ is hydrogen, $C_1$-$C_4$alkyl or $C_1$-$C_4$haloalkyl;
A represents CH or N;
X is S, SO or SO$_2$; and
$R_1$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl; or
$R_1$ is $C_3$-$C_6$cycloalkyl mono- or polysubstituted by substituents selected from the group consisting of halogen, cyano and $C_1$-$C_4$alkyl; or $R_1$ is $C_3$-$C_6$cycloalkyl-$C_1$-$C_4$alkyl mono- or polysubstituted by substituents selected from the group consisting of halogen, cyano and $C_1$-$C_4$alkyl; or
$R_1$ is $C_2$-$C_6$alkenyl, $C_2$-$C_6$haloalkenyl or $C_2$-$C_6$alkynyl;
$Yb_3$ is —B(OH)$_2$, —B(OR$_{b2}$)$_2$, in which $R_{b2}$ is a $C_1$-$C_6$alkyl or $Yb_3$ is
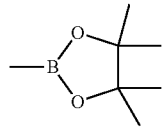
(a 4,4,5,5-tetramethyl-1,3,2-dioxaborolane group).
* * * * *